US012371460B2

(12) United States Patent
Imperiali et al.

(10) Patent No.: US 12,371,460 B2
(45) Date of Patent: *Jul. 29, 2025

(54) GLYCAN-BINDING PROTEINS AND RELATED COMPOSITIONS AND METHODS

(71) Applicant: Massachusetts Institute of Technology, Cambridge, MA (US)

(72) Inventors: Barbara Imperiali, Cambridge, MA (US); Cristina Zamora, Medford, MA (US); Elizabeth Ward, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 117 days.

This patent is subject to a terminal disclaimer.

(21) Appl. No.: 18/160,144

(22) Filed: Jan. 26, 2023

(65) Prior Publication Data

US 2024/0101620 A1    Mar. 28, 2024

Related U.S. Application Data

(63) Continuation of application No. 16/818,827, filed on Mar. 13, 2020, now Pat. No. 11,597,751.

(60) Provisional application No. 62/848,891, filed on May 16, 2019.

(51) Int. Cl.
*C07K 14/47* (2006.01)
(52) U.S. Cl.
CPC .................................. *C07K 14/47* (2013.01)
(58) Field of Classification Search
None
See application file for complete search history.

(56) References Cited

U.S. PATENT DOCUMENTS

| 9,422,548 | B2 | 8/2016 | Pecorari et al. |
| 11,597,751 | B2 | 3/2023 | Imperiali et al. |
| 2010/0159527 | A1 | 6/2010 | Martin et al. |
| 2012/0258460 | A1 | 10/2012 | Cheng et al. |
| 2014/0322825 | A1 | 10/2014 | Pancer et al. |
| 2016/0143990 | A1 | 5/2016 | Kitten |
| 2019/0113512 | A1 | 4/2019 | Sikes Johnson et al. |

FOREIGN PATENT DOCUMENTS

WO    WO 2007/011891 A2    1/2007

OTHER PUBLICATIONS

Invitation to Pay Additional Fees for PCT/US2020/022732 mailed Jun. 15, 2020.
International Search Report and Written Opinion for PCT/US2020/022732 mailed Aug. 13, 2020.
Banno et al. Development of a sugar-binding residue prediction system from protein sequences using support vector machine. Comput Biol Chem. 2017;66:36-43. doi: 10.1016/j.compbiolchem. 2016.10.009.
Barre et al., Mannose-binding plant lectins: different structural scaffolds for a common sugar-recognition process. *Biochimie*. 2001;83(7):645-651. doi:10.1016/s0300-9084(01)01315-3. Abstract only.
Baumann et al., DNA-binding surface of the Sso7d protein from Sulfolobus solfataricus. J Mol Biol. 1995;247(5):840-846. doi:10. 1006/jmbi.1995.0184.
Chua et al., Galectin-10, a potential biomarker of eosinophilic airway inflammation. PLoS One. 2012;7(8):e42549. doi: 10.1371/journal.pone.0042549. Epub Aug. 6, 2012. PMID: 22880030; PMCID: PMC3412795.
Flint et al. Ligand-mediated dimerization of a carbohydrate-binding molecule reveals a novel mechanism for protein-carbohydrate recognition. J Mol Biol. 2004;337(2):417-426. doi: 10.1016/j.jmb.2003. 12.081.
Gao et al., Unique Binding Specificities of Proteins toward Isomeric Asparagine-Linked Glycans. Cell Chem Biol. Apr. 18, 2019;26(4):535-547.e4. doi: 10.1016/j.chembiol.2019.01.002. Epub Feb. 7, 2019.
Gera et al., Highly stable binding proteins derived from the hyperthermophilic Sso7d scaffold. J Mol Biol. 2011;409(4):601-616. doi:10.1016/j.jmb.2011.04.020.
Gilbert et al., Editorial overview: Carbohydrate-protein interactions and glycosylation: integrating structural biology, informatics and systems modelling to understand glycan structure and glycan-protein interactions. Curr Opin Struct Biol. Oct. 2016;40:v-viii. doi: 10.1016/j.sbi.2016.11.009. Epub Nov. 27, 2016. PMID: 27899244.
Hong et al. Sugar-binding proteins from fish: selection of high affinity "lambodies" that recognize biomedically relevant glycans. ACS Chem Biol. 2013;8(1):152-160. doi:10.1021/cb300399s.
Kebriaei et al., Droplet Frequency Sensor: A new modality for sensitive, label-free, inline biochemical detection. IEEE. Transducers. 2017;642-645.
Lammerts Van Bueren et al., Carbohydrate-binding modules. CAZypedia. 2018.
Luo et al. Recognition of the Thomsen-Friedenreich pancarcinoma carbohydrate antigen by a lamprey variable lymphocyte receptor. J Biol Chem. 2013;288(32):23597-23606. doi:10.1074/jbc.M113. 480467.
Ng et al., Structural analysis of monosaccharide recognition by rat liver mannose-binding protein. J Biol Chem. 1996;271(2):663-674. doi:10.1074/jbc.271.2.663.

(Continued)

*Primary Examiner* — Anand U Desai
(74) *Attorney, Agent, or Firm* — Wolf, Greenfield & Sacks, P.C.

(57) ABSTRACT

Glycan-binding proteins, and compositions thereof, are generally described, including methods of making and using such proteins. The proteins may include scaffolds based on easily evolvable DNA-binding proteins, with binding sites able to specifically bind to mono- or disaccharides, such as monosaccharide-binding determinants, disaccharide-binding determinants, more complex carbohydrates, etc. In certain aspects, a protein may be generated starting from a small DNA-binding protein, such as Sso7d. Such glycan-binding proteins may have numerous applications, including in enzyme-linked immunosorbent assays (ELISAs), glycan characterization, cell selection, flow cytometry, histology, imaging, arrays, affinity purification, enzyme-linked visualization, binding to a target for pharmaceutical purposes, etc.

20 Claims, 18 Drawing Sheets
Specification includes a Sequence Listing.

(56) References Cited

OTHER PUBLICATIONS

Proft, Sortase-mediated protein ligation: an emerging biotechnology tool for protein modification and immobilisation. Biotechnol Lett. 2010;32(1):1-10. doi:10.1007/s10529-009-0116-0.

Song et al., Novel fluorescent glycan microarray strategy reveals ligands for galectins. Chem Biol. Jan. 30, 2009;16(1):36-47. doi: 10.1016/j.chembiol.2008.11.004. PMID: 19171304; PMCID: PMC2662446.

Stanley, Galectin-1 Pulls the Strings on VEGFR2. Cell. 2014;156(4):625-626. doi:10.1016/j.cell.2014.01.059.

Toscano et al., Dissecting the pathophysiologic role of endogenous lectins: glycan-binding proteins with cytokine-like activity? Cytokine Growth Factor Rev. Feb.-Apr. 2007;18(1-2):57-71. doi: 10.1016/j.cytogfr.2007.01.006. Epub Feb. 22, 2007. PMID: 17321195.

Traxlmayr et al. Strong Enrichment of Aromatic Residues in Binding Sites from a Charge-neutralized Hyperthermostable Sso7d Scaffold Library. J Biol Chem. 2016;291(43):22496-22508. doi:10.1074/jbc.M116.741314.

Wong et al. An intermolecular binding mechanism involving multiple LysM domains mediates carbohydrate recognition by an endopeptidase. Acta Crystallogr D Biol Crystallogr. 2015;71(Pt 3):592-605. doi:10.1107/S139900471402793X.

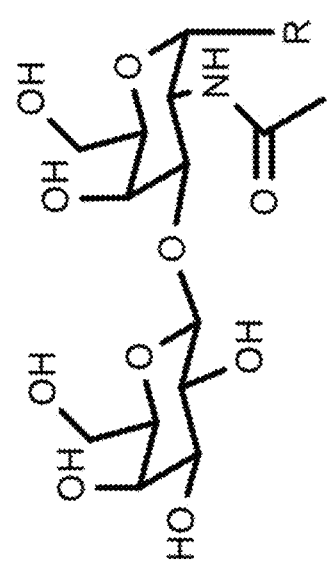
FIG. 2A Galβ1-3GalNAcα (TF)
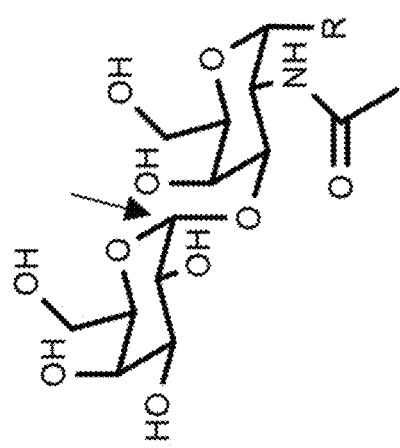
FIG. 2B Galα1-3GalNAcα
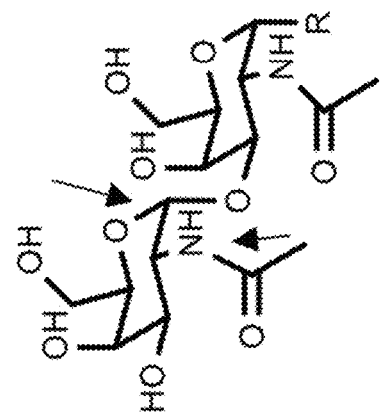
FIG. 2C GalNAcα1-3GalNAcα

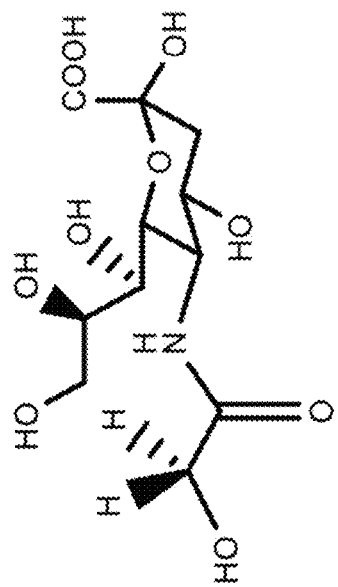
FIG. 3B Neu5Gc
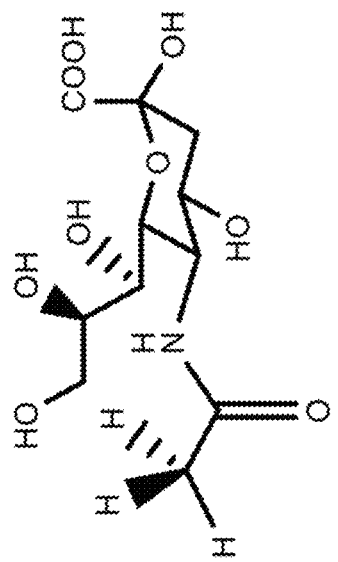
FIG. 3A Neu5Ac (sialic acid)

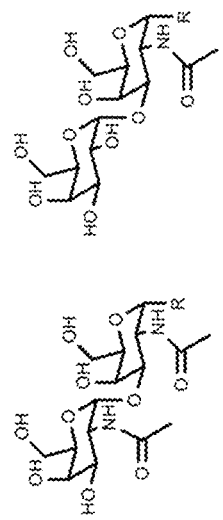
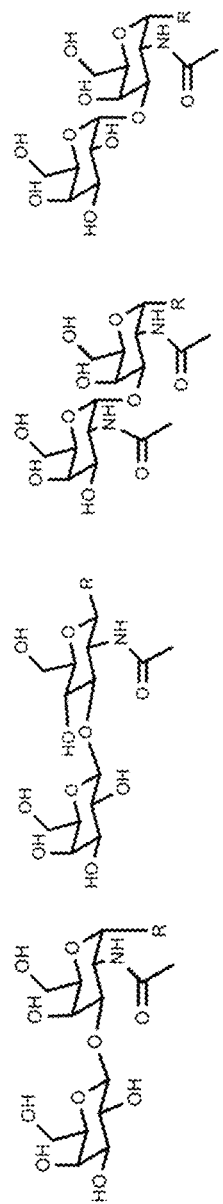
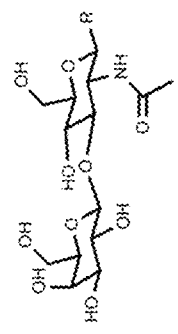
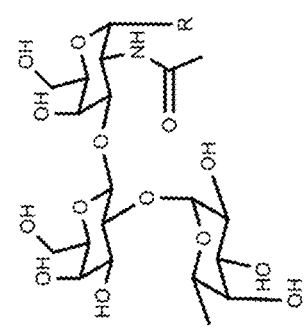
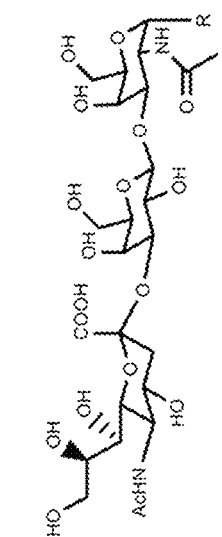
FIG. 9A Galβ1-3GalNAcα (TF antigen)
FIG. 9B Galβ1-3GlcNAβ (Le^c)
FIG. 9C GalNAcα1-3GalNAcα
FIG. 9D Galα1-3GalNAcα
FIG. 9E NeuSAcα2-3Galβ1-3GalNAcα (Sia-TF)
FIG. 9F Fucα1-2Galβ1-3GalNAcα (H3)

GLYCAN-BINDING PROTEINS AND RELATED COMPOSITIONS AND METHODS

RELATED APPLICATIONS

This application is a continuation of U.S. patent application Ser. No. 16/818,827, filed on Mar. 13, 2020, and entitled "Glycan-Binding Proteins and Related Compositions and Methods," which claims priority to U.S. Provisional Patent Application Ser. No. 62/848,891, filed on May 16, 2019, and entitled "Glycan-Binding Proteins and Related Compositions and Methods," each of which is hereby incorporated by reference in its entirety.

GOVERNMENT SPONSORSHIP

This invention was made with government support under AI130776 awarded by the National Institutes of Health. The government has certain rights in the invention.

REFERENCE TO AN ELECTRONIC SEQUENCE LISTING

The contents of the electronic sequence listing (M092570757US02-SEQ-LBS.xml; Size: 558,992 bytes; and Date of Creation: Jan. 26, 2023) is herein incorporated by reference in its entirety.

TECHNICAL FIELD

Glycan-binding proteins and related compositions and methods are generally described.

SUMMARY

Glycan-binding proteins, and compositions thereof, are generally described. Inventive methods of making and using the glycan-binding proteins are also described. The subject matter of the present invention involves, in some cases, interrelated products, alternative solutions to a particular problem, and/or a plurality of different uses of one or more systems and/or articles.

Certain aspects are related to compositions. In one aspect, a composition comprises a protein having at least 55% homology to the following sequence:

```
                                      (SEQ ID NO: 3)
ATVKFTYQGEEKQVDISKIK(s1)(s2)DEGGG(s3)SEKDAPKELLQML

EKQ
``` wherein (s1) consists of 7 amino acid residues and is not KKVWRVG (SEQ ID NO: 407), (s2) consists of 7 amino acid residues and is not QMISFTY (SEQ ID NO: 408), (s3) consists of 7 amino acid residues and is not ATGRGAV (SEQ ID NO: 409). In some embodiments, the protein specifically binds to a monosaccharide or disaccharide-binding determinant.

In another aspect, a composition comprises a protein having at least 55% homology to the following sequence:

```
                                      (SEQ ID NO: 4)
ATVKFTYQGEEKQVDISKIKKX¹VX²RX³GQX⁴IX⁵FX⁶YDEGGGAX⁷GX⁸G

X⁹VSEKDAPKELLQMLEKQ,
``` wherein each of $X^1$, $X^2$, $X^3$, $X^4$, $X^5$, $X^6$, $X^7$, $X^8$, and $X^9$ is independently an amino acid residue, with the proviso that $X^1$, $X^2$, $X^3$, $X^4$, $X^5$, $X^6$, $X^7$, $X^8$, and $X^9$ cannot simultaneously be K, W, V, M, S, T, T, R, and A, respectively. In some cases, the protein specifically binds to a monosaccharide or disaccharide-binding determinant.

In another aspect, a composition comprises a protein having 55-99% homology to the following sequence:

```
                                      (SEQ ID NO: 1)
ATVKFTYQGEEKQVDISKIKKVWRVGQMISFTYDEGGGATGRGAVSEKD

APKELLQMLEKQ,
``` wherein the protein specifically binds to a monosaccharide or disaccharide-binding determinant.

In yet another aspect, a composition comprises a first glycan-binding portion and a second glycan-binding portion. In some cases, each of the first glycan-binding portion and the second glycan-binding portion independently has at least 55% homology to Sso7d.

In addition, certain aspects are related to methods. For example, in one aspect, a method of producing a glycan-binding protein comprises providing a protein scaffold, wherein the protein scaffold comprises Sso7d, generating one or more variants of the protein scaffold, determining binding and/or binding selectivity of the one or more variants to a monosaccharide or disaccharide-binding determinant, selecting a variant exhibiting increased binding and/or binding selectivity to the monosaccharide or disaccharide-binding determinant from the one or more variants, and repeating the generating, determining and selecting steps, using the variant exhibiting increased binding and/or binding selectivity to the monosaccharide or disaccharide-binding determinant in each repeat.

In another aspect, a method of producing a glycan-binding protein comprises providing a protein scaffold, wherein the protein scaffold has no more than 200 amino acid residues, with a binding face area of less than or equal to 6 square nanometers ($nm^2$), generating one or more variants of the protein scaffold, determining binding and/or binding selectivity of the one or more variants to a monosaccharide or disaccharide-binding determinant, selecting a variant exhibiting increased binding and/or binding selectivity to the monosaccharide or disaccharide-binding determinant from the one or more variants, and repeating the generating, determining and selecting steps, using the variant exhibiting increased binding and/or binding selectivity to the monosaccharide or disaccharide-binding determinant in each repeat.

A large variety of proteins are described herein. For example, in one set of embodiments, the protein is selected from Sequence List 1. In another set of embodiments, the protein is selected from Sequence List 2.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIG. 2A illustrates the structure of Galβ1-3GalNAcα (TF or Thomsen-Friedenrich antigen).

FIG. 2B illustrates the structure of Galα1-3GalNAcα, with arrows towards various points of differentiation from the TF antigen.

FIG. 2C illustrates the structure of GalNAcα1-3GalNAcα, with arrows towards various points of differentiation from the TF antigen.

FIG. 3A illustrates the structure of Neu5Ac.

FIG. 3B illustrates the structure of Neu5Gc.

FIGS. 9A-9F illustrate disaccharides (or disaccharide motifs within trisaccharides) bound by glycan-binding proteins, in accordance with some embodiments described herein.

BRIEF DESCRIPTION OF THE SEQUENCES

Figure 1:
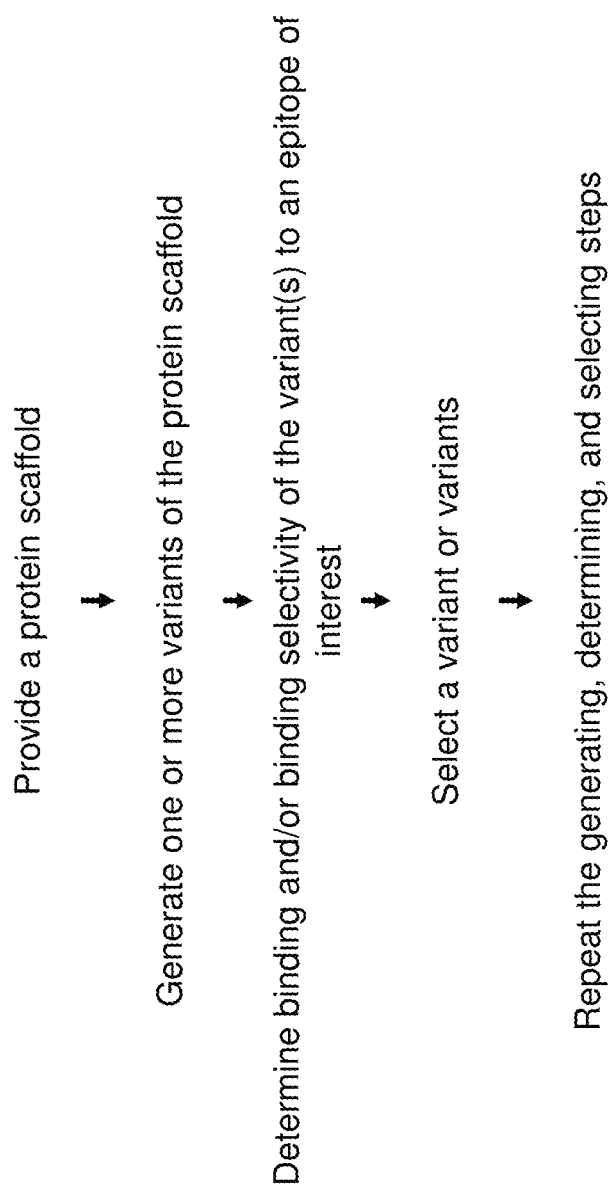
FIG. 1 illustrates a flowchart of methods of generating a glycan-binding protein, in some embodiments.

SEQ ID NO: 1 is a reduced-charge variant of Sso7d (rcSso7d), having a sequence:

ATVKFTYQGEEKQVDISKIKKVWRVGQMISFTYDEGGGATGRGAVSEKDA
PKELLQMLEKQ.

SEQ ID NO: 2 is Sso7d, a protein from *S. solfataricus* having a sequence:

ATVKFKYKGEEKQVDISKIKKVWRVGKMISFTYDEGGGKTGRGAVSEKDA
PKELLQMLEKQK.

SEQ ID NO: 3 is ATVKFTYQGEEKQVDISKIK(s1)(s2)DEGGG(s3) SEKDAPKELLQMLEKQ, where (s1) consists of 7 amino acid residues and is not KKVWRVG (SEQ ID NO: 407), (s2) consists of 7 amino acid residues and is not QMISFTY (SEQ ID NO: 408), and (s3) consists of 7 amino acid residues and is not ATGRGAV (SEQ ID NO: 409).

SEQ ID NO: 4 is the following amino acid sequence: ATVKFTYQGEEKQVDISKIKKX$^1$VX$^2$RX$^3$GQX$^4$IX$^5$FX$^6$YDEGGGAX$^7$GX$^8$GX$^9$VSE KDAPKELLQMLEKQ, where each of X$^1$, X$^2$, X$^3$, X$^4$, X$^5$, X$^6$, X$^7$, X$^8$, and X$^9$ is independently an amino acid residue, with the proviso that X$^1$, X$^2$, X$^3$, X$^4$, X$^5$, X$^6$, X$^7$, X$^8$, and X$^9$ cannot simultaneously be K, W, V, M, S, T, T, R, and A, respectively.

SEQ ID NO: 5 is M11.1, an artificial protein having the following sequence:

ATVKFTYQGEEKQVDISKIKWVIRWGQHIAFKYDEGGGAAGYGWVSEKDA
PKELLQMLEKQ.

SEQ ID NO: 6 is M11.2, an artificial protein having the following sequence:

ATVKFTYQGEEKQVDISKIKWVNRWGQRIYFKYDEGGGAAGYGWVSEKDA
PKELLQMLEKQ.

SEQ ID NO: 7 is M11.1.2, an artificial protein having the following sequence:

ATVKYTYRGEEKRVDISKIKWVNRWGQHLAFKYDKGGGAAGYGWVSEKDAP
KELLQMLEKR.

SEQ ID NO: 8 is M11.1.3, an artificial protein having the following sequence:

ATVKSTYRGEEKQVDISKIKWVIRWGQHLAFKYDEGGGAAGYGWVSEKDAP
KELLQMLEKQ.

SEQ ID NO: 9 is M11.1.5, an artificial protein having the following sequence:

ATVKFTYRGEEKQVDISKIKWVNRWGQHLAFKYDVGGGAAGYGWMSEKDAP
KELLQMLEKR.

SEQ ID NO: 10 is M18.1, an artificial protein having the following sequence:

ATVKFTYQGEEKQVDISKIKWVIRLGRTIMFKYDEGGGANGYGKVSEKDAP
KELLQMLEKQ.

SEQ ID NO: 11 is M18.2, an artificial protein having the following sequence:

ATVKFTYQGEEKQVDISKIKWVVRLGQVIMFKYDEGGGANGYGKVSEKDAP
KELLQMLEKQ.

SEQ ID NO: 12 is M18.2.2, an artificial protein having the following sequence:

ATVKFTYRGEEKQVDISKIKWVVRLGQVIMFKYGEGGGSNGYGRVSEKDA
PKELRQMLEKR.

SEQ ID NO: 13 is M18.2.5, an artificial protein having the following sequence:

ATVKFTYRGEEKQVDISKIKWVVRLGQVIMFKYDEGGGASGYGRVSEKDA
PKELLQMLEK.

DETAILED DESCRIPTION

Glycan-binding proteins, and compositions thereof, are generally described, including methods of making and using such proteins. The proteins may include scaffolds based on easily evolvable DNA-binding proteins, with binding sites able to specifically bind to mono- or disaccharides, such as monosaccharide-binding determinants, disaccharide-binding determinants, in more complex carbohydrates, etc. In certain aspects, a protein may be generated starting from a small DNA-binding protein, such as Sso7d. Such glycan-binding proteins may have numerous applications, including in enzyme-linked immunosorbent assays (ELISAs), glycan characterization, cell selection, flow cytometry, histology, imaging, arrays, affinity purification, enzyme-linked visualization, binding to a target for pharmaceutical purposes, etc.

Certain aspects of the invention are generally directed to proteins able to bind to glycans, for example, via specific binding. Glycans are generally sugars or carbohydrates, alone or conjugated to other entities, such as proteins, lipids, small molecules, or the like. The glycans may include any number of saccharide units, including monosaccharides, disaccharides, and larger polysaccharides. Glycans can be homo- or heteropolymers of monosaccharide residues, and can be linear or branched. The glycan may comprise only saccharide units, or other non-saccharide units as well, for example, as in glycoproteins, glycolipids, glyconucleic acids, proteoglycans, etc.

In some cases, glycan-binding proteins such as those discussed herein may be relatively small or low-molecular weight, and can accordingly bind to small glycan-binding determinants, e.g., monosaccharides or disaccharides within an overall glycan structure, e.g., via specific binding. Such glycan-binding determinants that the protein can bind may be a single monosaccharide or disaccharide, or in some cases, the glycan-binding determinant may be part of a larger structure, e.g., such as those noted above.

In contrast, other carbohydrate-binding proteins known to the art are typically significantly larger, and are unable to specifically bind to or recognize single monosaccharide or disaccharide-binding determinants. Glycan-binding proteins such as these may be useful in a variety of immunological, therapeutic, diagnostic, or technological roles such as those discussed herein.

In addition, certain embodiments of the invention are generally directed to systems and methods for making such glycan-binding proteins. In some cases, a DNA-binding protein may be used as a protein scaffold and engineered, e.g., using directed evolution, to produce a glycan-binding protein. In some cases, e.g., after multiple generations, proteins with high specificities of binding to glycans may be developed.

In some cases, the protein scaffold may be one that is readily evolvable. The protein scaffold may also, in certain embodiments, have a binding site (e.g., a binding pocket) that has dimensions compatible with monosaccharide and/or disaccharide binding, and/or have a binding site (e.g., a binding pocket) that has dimensions similar to those of any monosaccharide or disaccharide motif of interest within a glycan.

In addition, in certain embodiments, the protein scaffold may be devoid of disulfides. In some cases, the protein scaffold may be stable to a wide range of temperatures and/or pH values. In addition, such protein scaffolds may be one that can be readily functionalized chemically or conjugated to other entities, for example, to generate clustered or branched assemblies. For example, in one set of embodiments, two such protein scaffolds may be linked together.

As one non-limiting example, in some embodiments, Sso7d (or a reduced-charge variant thereof) can be used as a protein scaffold. Native or wild-type Sso7d arises from *Sulfolobus solfataricus*, where it binds DNA and does not ordinarily bind glycans. However, the Sso7d scaffold can be used to develop glycan-binding proteins, as discussed herein. For instance, in some embodiments, the Sso7d protein scaffold is mutated, for example, by error-prone PCR, to generate variants. These variants are then, in some cases, analyzed to determine binding efficiency to a target glycan, for instance, using Yeast-Surface Display (YSD) selections with magnetic bead-immobilized glycans. The variant or variants with the best binding and/or binding selectivity to the target glycan (e.g., a specific monosaccharide or disaccharide-binding determinant) are then selected, and the process is optionally repeated one or more times (e.g., the variant(s) undergo a session of random mutation, the variants generated from this session of mutation are analyzed via YSD, and the variant(s) with the best binding and/or binding selectivity to the target of interest are selected). As many repetitions can be done as desired and/or as required to achieve the desired binding constant and/or binding selectivity.

Based on techniques such as these, or others described herein, modified Sso7d proteins can be developed that can bind to various glycans, for example, but not limited to, a disaccharide (e.g. the dihexose Galβ1-3GalNAcα, also named the TF antigen, FIG. 2A) or a monosaccharide (e.g. the nonulosonic acid named Neu5Ac, FIG. 3A) and certain embodiments of the invention are also generally directed to such modified Sso7d proteins. In some cases, the binding may be relatively specific, for example, with a $K_D$ of less than $10^{-5}$ M, or other values such as those described herein.

In certain embodiments, glycan-binding proteins such as those discussed herein can be used in various applications. In some cases, the protein can be modified further. For example, a glycan-binding protein could be attached to another glycan-binding protein to, for example, increase the binding and/or binding selectivity even further. As another example, in certain instances, a glycan-binding protein could be attached to another structure (e.g., a fluorophore) to, for example, functionalize the protein for a particular use, such as use for ELISAs, therapeutics, glycan characterization, cell selection, flow cytometry, histology, imaging, arrays, affinity purification, and/or enzyme-linked visualization, among other applications. A variety of applications involving the binding of a glycan to a glycan-binding protein, e.g., specifically, thus may be realized.

The above discussion illustrates various non-limiting examples of some embodiments. However, other embodiments of glycan-binding proteins and compositions thereof are also possible, as discussed below.

Certain aspects are related to systems and methods for producing glycan-binding proteins and compositions thereof. Non-limiting examples of such glycan-binding proteins are discussed below. Exemplary directed evolution methods of producing glycan-binding proteins are described in relation to FIG. 1. However, it should be understood that the methods described herein have broader utility, and are not limited to generating the glycan-binding proteins described herein. In addition, it should be understood that other methods may be used instead of the methods described in FIG. 1, including other directed evolution methods as well as other methods, such as ab initio calculations, to produce glycan-binding proteins and other proteins such as those described herein.

Thus, some embodiments are generally directed to directed evolution method of producing a protein, such as a glycan-binding protein. As an example of a directed evolution method, in FIG. 1, the method comprises providing a protein scaffold and generating one or more variants of the scaffold, determining binding and/or selectivity of those variants (for example, to a binding determinant of interest, such as to a monosaccharide and/or disaccharide) and selecting those that meet desired criteria (e.g., improved binding and/or selectivity). These steps can be repeated in some cases.

Certain methods, including certain directed evolution methods, start with the identification of a suitable protein scaffold. The protein scaffold may then be randomly mutated under directed evolution to produce a protein having one or more desired characteristics, such as the ability to bind a glycan, in some cases specifically.

Figure 8B:
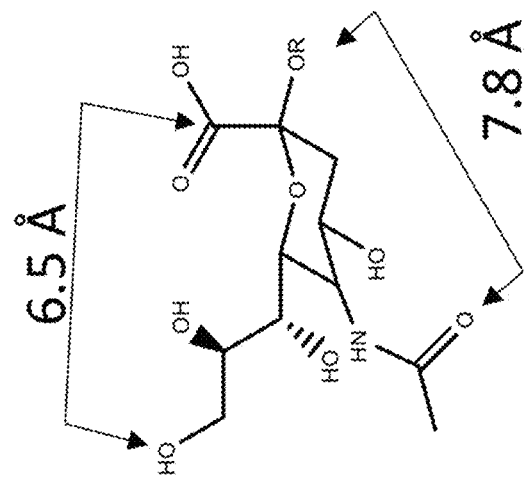
FIG. 8B illustrates the dimensions of an example monosaccharide (i.e., NeuN5Ac).
Figure 8A:
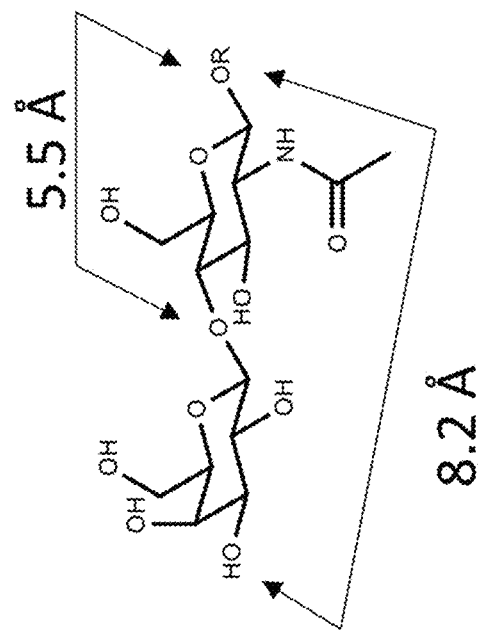
FIG. 8A illustrates the dimensions of an example disaccharide (i.e., TF antigen).

In some cases, the protein scaffold may be one that has a binding site (e.g., a binding pocket) that has dimensions compatible with monosaccharide and/or disaccharide binding, and/or have a structure that has dimensions similar to those of any monosaccharide or disaccharide motif of interest within a glycan In some cases the binding site may be one that is evolvable, e.g., as the protein scaffold is evolved using directed evolution. For example, the protein scaffold may be one that has a binding site (e.g., a binding pocket) that has dimensions compatible with monosaccharide and/or disaccharide binding, and/or have a binding site (e.g., a binding pocket) that has dimensions similar to those of any monosaccharide or disaccharide motif of interest within a glycan Examples of such dimensions are shown in FIGS. 8A-8B; in FIG. 8A, the dimensions of a typical disaccharide (the dihexose Galβ1-3GalNAcα) are shown; in FIG. 8B, the dimensions of a typical monosaccharide (the nonulosonic acid Neu5Ac) are shown. It should be understood that these dimensions are exemplary, and that other monosaccharides or disaccharides will have dimensions slightly different from these. However, the dimensions of the binding site of the protein scaffold may have dimensions comparable to these. For example, the binding site may have a largest dimension that is smaller than 30 Angstroms, smaller than 25 Angstroms, smaller than 20 Angstroms, smaller than 15 Angstroms, smaller than 10 Angstroms, smaller than 9.8 Angstroms, smaller than 9.6 Angstroms, smaller than 9.4 Angstroms, smaller than 9.2 Angstroms, smaller than 9.0 Angstroms, smaller than 8.8 Angstroms, smaller than 8.6 Angstroms, smaller than 8.4 Angstroms, smaller than 8.2 Angstroms, smaller than 8.0 Angstroms, smaller than 7.8 Angstroms, smaller than 7.6 Angstroms, smaller than 7.4 Angstroms, smaller than 7.2 Angstroms, smaller than 7.0 Angstroms, etc.

In some cases, the protein scaffold may be selected to have a binding face area of at least 1, at least 2, at least 3, at least 4, at least 5, at least 6, or at least 7 square nanometers ($nm^2$). The protein scaffold, in some instances, has a binding face area of less than or equal to 6, less than or equal to 5, less than or equal to 4, or less than or equal to 3 square nanometers ($nm^2$). Combinations of these ranges are also possible (e.g., 2-6 square nanometers ($nm^2$)). The binding face area can be calculated by looking at the binding site of the protein scaffold, finding the longest dimension of that site, and multiplying it by the dimension of the site at a 90 degree angle from the longest dimension. For example, if the longest dimension is 30 Angstroms and the orthogonal dimension is 15 Angstroms, then the binding face area would be 450 Angstroms$^2$ (1.5×3.0) or 4.5 $nm^2$.

The protein scaffold itself may, in some cases, be one that is based on a relatively small protein, for example, one that is slightly greater than these dimensions. This may, for example, allow for multiple scaffolds to be conjugated together with minimal additional sequences. For example, the protein scaffold may be one that has a relatively low number of amino acids, e.g., less than 250 amino acids. In certain cases, the protein scaffold has less than or equal to 200 amino acid residues, less than or equal to 175 amino acid residues, less than or equal to 150 amino acid residues, less than or equal to 125 amino acid residues, less than or equal to 100 amino acid residues, or less than or equal to 75 amino acid residues. In accordance with some embodiments, the protein scaffold has greater than or equal to 25 amino acid residues, greater than or equal to 50 amino acid residues, greater than or equal to 75 amino acid residues, greater than or equal to 100 amino acid residues, or greater than or equal to 150 amino acid residues. Combinations of these ranges are also possible (e.g., the protein scaffold may have between 50-100 amino acid residues, between 50-75 amino acid residues, between 75-100 amino acid residues, or the like).

In certain instances, the protein scaffold has a maximum dimension of less than or equal to 200 Angstroms, less than or equal to 150 Angstroms, less than or equal to 100 Angstroms, less than or equal to 50 Angstroms, less than or equal to 40 Angstroms, less than or equal to 30 Angstroms, less than or equal to 25 Angstroms, less than or equal to 20 Angstroms, less than or equal to 15 Angstroms, less than or equal to 10 Angstroms, less than or equal to 7 Angstroms, or less than or equal to 3 Angstroms. In addition, according to some embodiments, the protein scaffold has a maximum dimension of greater than or equal to 5 Angstroms, greater than or equal to 9 Angstroms, greater than or equal to 12 Angstroms, greater than or equal to 15 Angstroms, greater than or equal to 18 Angstroms, greater than or equal to 20 Angstroms, greater than or equal to 25 Angstroms, greater than or equal to 30 Angstroms, greater than or equal to 40 Angstroms, etc. Combinations of these ranges are also possible (e.g., the protein scaffold may have a maximum dimension of between 15-20 Angstroms, between 20-25 Angstroms, between 10-30 Angstroms, etc.).

In addition, in some embodiments, the protein scaffold may be substantially devoid of disulfides or cysteine residues. Cysteines may cause problems with respect to disulfide bond formation, which can significantly alter the molecular structure of the protein scaffold, e.g., during the directed evolution process. For example, there may be no more than 4, 3, 2, or 1 cysteines within the protein scaffold. In some cases, no cysteines are present. Similarly, the protein scaffold may have fewer than or equal to 2, or 1 disulfide bonds, or the protein scaffold may be free of disulfide bonds.

In some cases, the protein scaffold may be selected to have a relatively high melting temperature ($T_m$), i.e., the protein scaffold may exhibit high thermal stability. For example, the protein scaffold may exhibit a melting temperature of greater than or equal to 50° C., greater than or equal to 60° C., greater than or equal to 70° C., greater than or equal to 80° C., greater than or equal to 90° C. greater than or equal to 100° C., greater than or equal to 125° C., greater than or equal to 150° C., etc. In some cases, the melting temperature may be less than or equal to 150° C., less than or equal to 125° C., less than or equal to 100° C., less than or equal to 90° C., or less than or equal to 80° C. Combinations of these ranges are also possible (e.g., 60° C. to 125° C. (inclusive)). The melting temperature or melting point is generally the temperature at which the protein begins to denature or lose its shape or 3D conformation. Accordingly, melting temperature can be determined, for example, by increasing the temperature and observing any changes in three-dimensional structure using circular dichroism (CD), differential scanning calorimetry (DSC) measurements, or the like.

The protein scaffolds may also be selected to be stable to a wide range of pH conditions. For example, the protein scaffold may be stable at a pH of greater than or equal to 1, greater than or equal to 2, greater than or equal to 3, greater than or equal to 4, greater than or equal to 5, or greater than or equal to 6. In some embodiments, the protein scaffold may be stable at a pH of less than or equal to 12, less than or equal to 11, less than or equal to 10, less than or equal to 9, or less than or equal to 8. Combinations of these ranges are also possible. For example, in some cases, the protein and/or the protein scaffold used to generate a glycan-binding protein are stable within a pH of between 2-11, or within a pH between 1-12. pH stability can be determined, for example, by adjusting the pH of the solution and observing changes in three-dimensional structure (e.g., using CD) after 30 minutes.

In some cases, a protein scaffold may be selected to be readily functionalized chemically or conjugated to other entities, for example, to generate clustered or branched assemblies. For example, the protein scaffold may be one that is capable of chemical functionalization, array display, and/or conjugation. This may be useful, for example, to generate clustered and branched assemblies to exploit avidity effects, which can be important in glycan binding in some cases. In certain embodiments, the size of the protein scaffold may be sufficiently compact, e.g., having the dimensions as discussed above, so that non-binding components of the scaffold do not substantially interfere with conjugation of glycan readers for binding multivalent glycans and more complex glycan targets. For example, in some embodiments, two protein scaffolds may be linked or conjugated together, e.g., to bind to more complex glycan targets. In some cases, the protein scaffold may be selected to be amenable to high-yield protein expression in *Escherichia coli* and facile bioconjugation to fluorophores, purification tags, biocompatible resins, 2-dimensional (2D) arrays, or the like. In addition, in some embodiments, the protein scaffold may be selected to be compatible with yeast surface display, in the presence and/or in the absence of $Ca^{2+}$ or any other metal ion or cofactor.

Examples of protein scaffolds that may be suitable to produce glycan-binding proteins, such as those discussed herein, include Affibody, Fn3 domain, DARPins, Lambody, and Sso7d, these are summarized in Table 1.

TABLE 1

| SCAFFOLD | # Residues | WT $T_m$ (° C.) |
| --- | --- | --- |
| Affibody | 58 | 78 |
| Fn3 domain | 94 | 84 |
| DARPins | 130-190 | variable |
| Lambody | 217 | n/d |
| Sso7d | 63 | 98 |

Thus, in one set of embodiments, the protein scaffold may be Sso7d (e.g., from *Sulfolobus solfataricus*), or variants thereof. Sso7d has the following sequence:

(SEQ ID NO: 2)
ATVKFKYKGEEKQVDISKIKKVWRVGKMISFTYDEGGGKTGRGAVSEK

DAPKELLQMLEKQK

In addition, the protein scaffold may be based on the reduced-charge variant of Sso7d (rcSso7d), for example, comprising the following sequence:

(SEQ ID NO: 1)
ATVKFTYQGEEKQVDISKIKKVWRVGQMISFTYDEGGGATGRGAVSEKD

APKELLQMLEKQ.

Thus, in certain cases, the protein scaffold may be based on Sso7d or rcSso7d, with 10, 9, 8, 7, 6, 5, 4, 3, 2, or 1 changed residues. In some cases, the protein scaffold may be based on rcSso7d, but with greater than or equal to 70%, greater than or equal to 80%, greater than or equal to 90%, greater than or equal to 95%, or greater than or equal to 99% homology. The protein scaffold may also have less than or equal to 99%, less than or equal to 95%, less than or equal to 90%, or less than or equal to 85% homology to Sso7d or rcSso7d. Combinations of these ranges are also possible (e.g., 90-99% homology).

In certain embodiments, the method comprises generating one or more variants of the protein scaffold, e.g., as is shown in FIG. 1. Any number of variants may be generated. In addition, a variety of methods may be used to generate variants of the protein scaffold. For example, in some embodiments, error-prone PCR can be used to mutate the protein scaffold randomly. Other non-limiting examples include various experimental techniques (such as error-prone PCR, chemical mutagenesis, UV irradiation, etc.), or computer-based approaches (e.g., altering the amino acid sequence, e.g., randomly or with particular mutations, such as relatively conservative mutations). In some cases, site-directed mutagenesis techniques may be used (e.g., focused on one or more of the variable residue portions of a protein scaffold, such as those discussed herein). In other cases, the mutations may be randomly generated, e.g., without regard to any particular focus within the protein scaffold.

In some embodiments, the variants of the protein scaffold that are generated include, on average, greater than or equal to 1 amino acid, greater than or equal to 2 amino acids, greater than or equal to 3 amino acids, greater than or equal to 5 amino acids, etc., in each round of mutation. In certain embodiments, there may be less than or equal to 5 amino acids, less than or equal to 4 amino acids, less than or equal to 3 amino acids, or less than or equal to 2 amino acids that were mutated in a protein scaffold in a round of mutation. Combination of these ranges are also possible. In some cases, the number of mutations in a protein scaffold may not be deterministic, i.e., in techniques, such as error-prone PCR, that generate random mutations within a protein scaffold.

In some cases, the variant protein scaffolds may be studied to determine which ones exhibit desired characteristics. For example, the variants exhibiting increased binding and/or binding selectivity to the target of interest (e.g., the monosaccharide or disaccharide-binding determinant) may be determined. In some embodiments, binding and/or binding selectivity of the one or more variants to a target of interest, such as a glycan, may be used. Examples of potential targets include monosaccharide or disaccharide-binding determinants, more complex carbohydrates, or the like, e.g., as discussed herein.

For example, in accordance with certain embodiments, binding and/or binding selectivity may be determined based on binding of the variants to a target of interest, such as a monosaccharide or disaccharide-binding determinant. Non-limiting examples of monosaccharide-binding determinants include hexoses (e.g., glucose, galactose, fructose, etc.), hexosamines (e.g. glucosamine, galactosamine), heptoses or heptuloses (e.g., sedoheptulose, mannoheptulose, L-glycero-D-manno-heptose, etc.), octoses or octulosonic acids (e.g., methylthiolincosamide), nonoses or nonulosonic (sialic) acids (e.g., Kdn, Neu5Gc, Neu, Neu2en5Ac), and Neu5Ac (sialic acid) etc., as well as derivatives thereof having one or more additional substitutions at the hydroxyl groups, e.g., on C-4, C-7, C-8, and/or C-9 (such as O-acetyl, O-methyl, 0-sulfate, O-lactyl, or phosphate groups, etc.), octulosonic acids and derivatives thereof (e.g. KDO or keto-deoxyoctulosonate), and nonulosonic acids and derivatives thereof (e.g. Leg or legionaminic acid, Pse or pseudaminic acid, etc.). Non-limiting examples of disaccharide-binding determinants include dihexoses (e.g., sucrose, lactose, maltose, etc.), diheptoses, and Galβ1-3GalNAcα (TF or Thomsen-Friedenrich antigen). Those of ordinary skill in the art will be familiar with other monosaccharide or disaccharide-binding determinants as well that can be used in other embodiments, e.g., as a target of interest. Many of these have been widely discussed in the scientific literature.

Thus, one or more variants may be selected that exhibit increased binding and/or binding selectivity to a target, such as a monosaccharide or disaccharide-binding determinant. In some cases, for example, variants exhibiting improved binding (e.g., as measured by the dissociation constant or $K_D$) may be selected, for example, improvements of at least 5% or at least 10% in $K_D$ in a given round of mutation/selection. It will be understood that generally, higher affinities produce smaller $K_D$ values, as discussed below. Thus, such improved variants can be determined by determining $K_D$ values, and selecting those that meet some suitable criteria, e.g., by selecting variants that have less than a certain $K_D$ value, by selecting a certain number or percentage of variants as ranked by their $K_D$ values, or the like (e.g., the 5% or 10% of variants with the lowest $K_D$ values, etc.).

In some cases, variants that are selected may be those that are able to specifically bind to a target, such as a glycan. For example, specific binding may be observed with $K_D$ values of less than $10^{-5}$ M, less than $10^{-6}$ M, less than $10^{-7}$ M, less than $10^{-8}$ M, less than $10^{-9}$ M, less than $10^{-10}$ M, etc.

A variety of methods of determining $K_D$ values can be used, e.g., based on the glycan or other target. For example, one suitable technique is yeast-surface display (YSD), e.g., using with magnetic bead-immobilized glycans as discussed below. The yeast (and the variants) can be sorted, for example, using fluorescence-activated cell sorting (FACS) or other flow cytometry techniques. Other non-limiting examples include expression in alternative systems (e.g. bacteria, insect cells, mammalian cells, or the like), biolayer interferometry traces, surface plasmon resonance (SPR) traces, binding to immobilized glycan arrays, or the like. In addition, it should be understood that other methods of determining binding or selectively may be used, instead of and/or in in addition to determining $K_D$ values.

Figure 7:
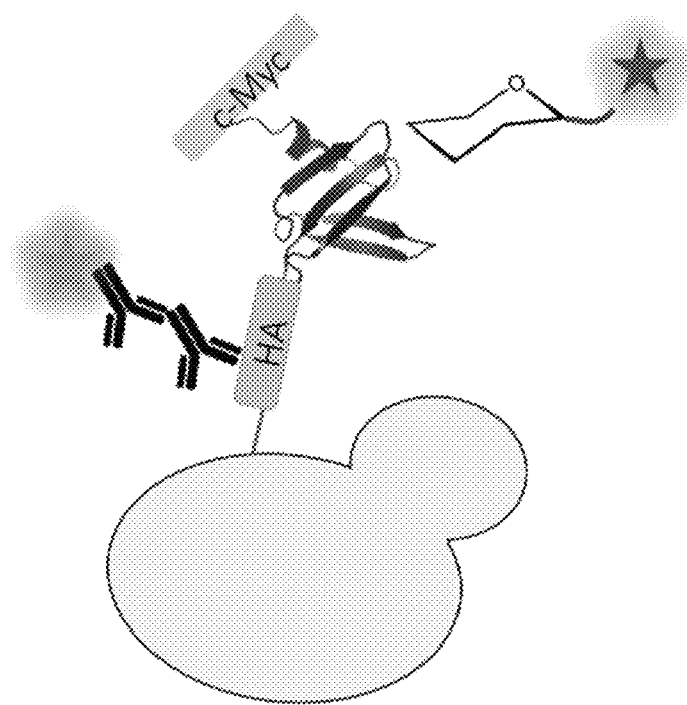
FIG. 7 illustrates a yeast-surface display of a glycan-binding protein binding a sugar-binding determinant, in accordance with certain embodiments.

Thus, in some embodiments, the determination and/or selection are accomplished using Yeast-Surface Display (YSD) selections with magnetic bead-immobilized glycans. For example, in FIG. 7, yeast-surface display is used to determine whether a variant binds a sugar-binding determinant of interest (e.g., a monosaccharide or disaccharide-binding determinant). Moreover, in certain embodiments, YSD will be used in the presence or in the absence of $Ca^{2+}$ or other metal ion or cofactor. Accordingly, in some cases, the protein scaffold is compatible with YSD in the presence of $Ca^{2+}$ and/or in the absence of $Ca^{2+}$.

In certain embodiments, the above steps (e.g., generating, determining, and selecting) may be repeated, using the variant exhibiting increased binding and/or binding selectivity as the next protein scaffold that binds to the target (e.g., a monosaccharide or disaccharide-binding determinant) in each repeat. In some instances, the generating, determining, and selecting steps are repeated, for example, until one or more variants with the desired binding and/or binding selectivity is obtained, e.g., as discussed herein. In some embodiments, these steps are repeated at least once, at least 5 times, at least 10 times, at least 20 times, or more in some cases. In certain instances, these steps are repeated less than or equal to 25 times, less than or equal to 20 times, less than or equal to 10 times, less than or equal to 5 times, or less than or equal to 2 times. Combinations of these ranges are also possible (e.g., 1-2 times).

In certain cases, once the variant has been characterized and/or its sequence has been identified, the generated protein can then be made with other common techniques available in the art. For example, the protein could be synthesized or it could be expressed in cells, such as in *E. coli*. Those of ordinary skill in the art will be aware of systems and methods for expressing a protein from its nucleic acid sequence.

Another aspect of the present invention is generally related to glycan-binding proteins and compositions thereof, e.g., generated using the techniques discussed above, or other techniques. The protein, in accordance with certain embodiments, may be able to bind to a glycan-binding determinant including any of those described herein e.g., via specific binding. For example, the protein may exhibit binding to a monosaccharide or a disaccharide-binding determinant, e.g., with $K_D$ values of less than $10^{-5}$ M, less than $10^{-6}$ M, less than $10^{-7}$ M, less than $10^{-8}$ M, less than $10^{-9}$ M, less than $10^{-10}$ M, etc. In addition, the protein can exhibit selective binding to a target glycan in certain embodiments, e.g. as compared to other glycans having similar structures. For example, the protein may be able to tightly bind to single copies of a binding determinant and/or distinguish differences at the atomic level.

As an example, as discussed, certain glycan-binding proteins are generally based on rcSso7d used as a protein scaffold. Native Sso7d is a DNA-binding protein, but does not significantly bind glycans. It forms an SH3-domain-like fold with five beta (β)-strands and an alpha (α)-helix at the C-terminus. In certain embodiments, the protein rcSso7d has a similar, or identical, three-dimensional structure to that of native Sso7d. For example, in certain cases, the protein has an SH3-domain-like fold. The protein, in some instances, has five beta (β)-strands. The protein has an alpha (α)-helix at the C-terminus, in certain embodiments. The three-dimensional structure of the protein may be considered similar to that of Sso7d if it has one or more of (i) an SH3-domain-like fold, (ii) five beta (β)-strands, or (iii) an alpha (α)-helix at the C-terminus.

In some cases, for example, the glycan-binding protein may exhibit a certain degree of homology to Sso7d (SEQ ID NO: 2), or to modified Sso7d sequences such as those described herein, for instance, the reduced-charge variant of Sso7d (rcSso7d) shown as SEQ ID NO: 1. For instance, the glycan-binding protein may exhibit 50% or greater, 55% or greater, 60% or greater, 65% or greater, 68% or greater, 70% or greater, 75% or greater, 80% or greater, 85% or greater, 90% or greater, 95% or greater homology, 97% or greater, or 99% to one or more of the sequences disclosed herein, for example, Sso7d, a modified Sso7d such as the reduced-charge variant of Sso7d (rcSso7d) of SEQ ID NO: 1, or other scaffold protein such as affibodies, Fn3 domains, DARPins, Lambodies, or the like. The glycan-binding protein may also have 99% or less, 95% or less, 90% or less, 85% or less, 80% or less, 75% or less, 70% or less, 65% or less, or 60% or less homology to one or more of those sequences. Combinations of these ranges are also possible (e.g., 55-90% homology, 68-90% homology, 75-90% homology, and 75-85% homology, etc.). As mentioned, there may be variants from the original scaffold protein, e.g., caused by directed evolution or other techniques descried herein, that allow the protein to bind to glycans. Thus, in some cases, the homology may exclude 100% (i.e., exclude wild-type scaffold proteins), since such proteins may not be able to bind glycans, or bind to glycans very poorly.

In some embodiments, the glycan-binding protein may have at least 1, at least 2, at least 3, at least 4, at least 5, at least 6, at least 8, at least 10, at least 12, at least 14, at least 16, at least 18, at least 20, at least 22, at least 24, at least 26, at least 28, at least 30, at least 32, at least 34, at least 36, at least 38, and/or no more than 40, no more than 38, no more than 36, no more than 34, no more than 32, no more than 30, no more than 28, no more than 26, no more than 24, no more than 22, no more than 20, no more than 18, no more than 16, no more than 14, no more than 12, no more than 10, no more than 8, no more than 6, no more than 5, no more than 4, no more than 3, or no more than 2 mutations relative to the initial scaffold protein, e.g., to Sso7d, a modified Sso7d such as the reduced charge variant of Sso7d (rcSso7d) of SEQ ID NO: 1, or other scaffold protein such as affibodies, Fn3 domains, DARPins, Lambodies, or the like. As a non-limiting example, a scaffold protein may have 2-4, 6-8, or 10-14 mutations relative to SEQ ID NO: 1 or SEQ ID NO: 2.

In addition, in some cases, the glycan-binding protein may have at least 34 amino acids, at least 37 amino acids, at least 40 amino acids, at least 43 amino acids, at least 46 amino acids, at least 49 amino acids, at least 52 amino acids, at least 55 amino acids, or at least 58 amino acids of one or more of the sequences in the same order. In certain embodiments, the protein may have 61 or fewer amino acids, 58 or fewer amino acids, 55 or fewer amino acids, 52 or fewer amino acids, 49 or fewer amino acids, 46 or fewer amino acids, 43 or fewer amino acids, 40 or fewer amino acids, or 37 or fewer amino acids of one or more of the sequences disclosed above in the same order. Combinations of these ranges are also possible (e.g., 37-58 amino acids of the sequences disclosed above in the same order).

In some embodiments, the amino acids may be contiguous or noncontiguous. For example, the following sequence (discussed in Example 2, Sequence List 1) has 45 amino acids (shown in underlining) of SEQ ID NO: 1:

(SEQ ID NO: 14)
ATVKFTYRGEEKQVGVSRVKSVHRIGQWIKFWYDEGSGAYGRGYVSEK

DAPEELLQMLEKRGSEQKLISEEDL.

Notably, in this example, some of the homologous amino acids are contiguous (e.g., the following 7 amino acid stretch: ATVKFTY (SEQ ID NO: 15)) while others are noncontiguous (e.g., the following 8 homologous amino acids in an 18 amino acid stretch: GVSRVKSVHRIGQWIKFW (SEQ ID NO: 16)).

In some cases, there may be additional amino acids that are not present in the protein scaffold, before, after, and/or in between contiguous sections. For example, in the above example, the protein has 12 amino acids at the end of its sequence that are not present in the protein scaffold (SEQ ID NO: 1). Similarly, in certain instances, there may be sections of the protein scaffold that are missing from the protein. For example, in the above example, the protein contains the sequence OVGVSRVKSV (SEQ ID NO: 410) while the protein scaffold (SEQ ID NO: 1) contains the sequence OVDISKIKKV (SEQ ID NO: 411). In this case, the protein scaffold has an extra amino acid (11 amino acids compared to 10 amino acids). Lastly, in this example, since there are 45 amino acids of the protein scaffold in the protein, 62 amino acids in the protein scaffold, and 73 amino acids in the protein, the protein has 72.6% (45/62) homology to the protein scaffold (SEQ ID NO:1).

As mentioned, certain embodiments of the invention are generally directed to modified Sso7d sequences that are able to bind to a glycan, for instance specifically. In some instances, the protein may be able to bind to a monosaccharide or disaccharide-binding determinant. For example, in some cases, the Sso7d, or a reduced charge variant thereof, may be modified in one or more surface-exposed residues on the protein. For instance, in one set of embodiments, 1, 2, 3, 4, 5, 6, 7, 8, or 9 or more surface-exposed residues may be modified. As a specific non-limiting example, certain embodiments of the invention are generally directed to the following sequence:

ATVKFTYQGEEKQVDISKIKKX$^1$VX$^2$RX$^3$GQX$^4$IX$^5$FX$^6$YDEGGGAX$^7$GX$^8$G

X$^9$VSEKDAPKELLQMLEKQ, where each of $X^1$, $X^2$, $X^3$, $X^4$, $X^5$, $X^6$, $X^7$, $X^8$, and $X^9$ is independently an amino acid residue, with the proviso that $X^1$, $X^2$, $X^3$, $X^4$, $X^5$, $X^6$, $X^7$, $X^8$, and $X^9$ cannot all be K, W, V, M, S, T, T, R, and A, respectively (SEQ ID NO: 4). However, it should be understood that individually, one or more of these substitutions may still be made, e.g., 1, 2, 3, 4, 5, 6, 7, or 8 of the substitutions of $X^1$ with K, $X^2$ with W, $X^3$ with V, $X^4$ with M, $X^5$ with S, $X^6$ with T, $X^7$ with T, $X^8$ with R, and $X^9$ with A can be made in various embodiments.

In addition, other embodiments of the invention are generally directed to sequences that are homologous to any of the above sequences, e.g., sequences exhibiting 50% or greater, 55% or greater, 60% or greater, 65% or greater, 68% or greater, 70% or greater, 75% or greater, 80% or greater, 85% or greater, 90% or greater, 95% or greater homology, 97% or greater, and/or 99% or less, 95% or less, 90% or less, 85% or less, 80% or less, 75% or less, 70% or less, 65% or less, or 60% or less homology to this sequence. Combinations of these ranges are also possible (e.g., 55-90% homology, 68-90% homology, 75-90% homology, and 75-85% homology, etc.).

In certain cases, the protein may be a modified Sso7d sequences that are able to bind to a glycan, e.g. specifically. For example, the protein may be able to bind to a monosaccharide or disaccharide-binding determinant. In one embodiment, the protein has the following sequence:

(SEQ ID NO: 3)
ATVKFTYQGEEKQVDISKIK(s1)(s2)DEGGG(s3)SEKDAPKELLQML
EKQ.

In this sequence, (s1), (s2), and (s3) represent regions of a reduced charge Sso7d variant that are surface-exposed, and may be modified. For example, independently within each of (s1), (s2), and (s3), 1, 2, 3, 4, 5, 6, or 7 of the amino acid residues within these sequences may be modified. In the initial variant, (s1) is KKVWRVG (SEQ ID NO: 407), (s2) is QMISFTY (SEQ ID NO: 408), and (s3) is ATGRGAV (SEQ ID NO: 409), and one or more of (s1), (s2), and (s3) may be modified, e.g., to have a sequence different than these. Thus, for example, in one embodiment, (s1) consists of 7 amino acid residues and is not KKVWRVG (SEQ ID NO: 407), (s2) consists of 7 amino acid residues and is not QMISFTY (SEQ ID NO: 408), and (s3) consists of 7 amino acid residues and is not ATGRGAV (SEQ ID NO: 409).

In some embodiments, 1, 2, or 3 of positions 2, 4, and 6 of (s1) may be modified, e.g., with a different amino acid residue, for example, as in $KX^1VX^2RX^3G$ (SEQ ID NO: 412), where each of $X^1$, $X^2$, and $X^3$ independently are amino acid residues, although $X^1$, $X^2$, and $X^3$ cannot simultaneously be K, W, and V, respectively. In some embodiments, 1, 2, or 3 of positions 2, 4, and 6 of (s2), e.g., with a different amino acid residue, for example, as in $QX^4IX^5FX^6Y$ (SEQ ID NO: 413), where each of $X^4$, $X^5$, and $X^6$ independently are amino acid residues, although $X^4$, $X^5$, and $X^6$ cannot simultaneously be M, S, and T. In some embodiments, 1, 2, or 3 of positions 2, 4, and 6 of (s3), e.g., with a different amino acid residue. In addition, in certain cases, the substitution is not with cysteine, for example, as in $AX^7GX^8GX^9V$ (SEQ ID NO: 414), where each of $X^7$, $X^8$, and $X^9$ independently are amino acid residues, although $X^7$, $X^8$, and $X^9$ cannot simultaneously be T, R, and A.

In addition, other embodiments of the invention are generally directed to sequences that are homologous to any of the above-described sequences, e.g., sequences exhibiting 50% or greater, 55% or greater, 60% or greater, 65% or greater, 68% or greater, 70% or greater, 75% or greater, 80% or greater, 85% or greater, 90% or greater, 95% or greater homology, 97% or greater, and/or 99% or less, 95% or less, 90% or less, 85% or less, 80% or less, 75% or less, 70% or less, 65% or less, or 60% or less homology to this sequence. Combinations of these ranges are also possible (e.g., 55-90% homology, 68-90% homology, 75-90% homology, and 75-85% homology, etc.).

Non-limiting examples of such proteins include those described in Sequence List 1 and Sequence List 2 (shown in Example 2).

Any of the amino acid substitutions described anywhere herein may be a substitution with natural and/or unnatural amino acids, and may include 1 or 2, 3, 4, etc., amino acids that are substituted in. Those of ordinary skill in the art will be aware of amino acids. For instance, the naturally-occurring amino acids include are the 20 amino acids most commonly found in nature, typically in the L-isomer, i.e., alanine ("Ala" or "A"), arginine ("Arg" or "R"), asparagine ("Asn" or "N"), aspartic acid ("Asp" or "D"), cysteine ("Cys" or "C"), glutamine ("Gln" or "Q"), glutamic acid ("Glu" or "E"), glycine ("Gly" or "G"), histidine ("His" or "H"), isoleucine ("Ile" or "I"), leucine ("Leu" or "L"), lysine ("Lys" or "K"), methionine ("Met" or "M"), phenylalanine ("Phe" or "F"), proline ("Pro" or "P"), serine ("Ser" or "S"), threonine ("Thr" or "T"), tryptophan ("Trp" or "W"), tyrosine ("Tyr" or "Y"), and valine ("Val" or "V"). In some embodiments, only natural amino acids are used in the protein.

However, in some cases, one or more unnatural amino acids may be present. An unnatural amino acid is an amino acid (or an imino acid) that is not one of the 20 natural amino acids. Non-limiting examples of unnatural amino acids include D-isomers of the natural amino acids (with the exception of glycine, which is identical to its L-isomer), as well as other amino acids such as alloisoleucine, allothreonine, homophenylalanine, homoserine, homocysteine, 5-hydroxylysine, 4-hydroxyproline, 4-carboxyglutamic acid, cysteic acid, cyclohexylalanine, ethylglycine, norleucine, norvaline, 3-aminobutyric acid, beta-amino acids (e.g., beta-alanine), N-methylated amino acids such as N-methylglycine, N-methylalanine, N-methylvaline, N-methylleucine, N-methylisoleucine, N-methylnorleucine, N-methyl-2-aminobutyric acid, N-methyl-2-aminopentanoic acid, etc.

In some cases, the glycan-binding protein may have a relatively high melting temperature ($T_m$) or exhibit high thermal stability. For example, the glycan-binding protein may exhibit a melting temperature of greater than or equal to 50° C., greater than or equal to 60° C., greater than or equal to 70° C., greater than or equal to 80° C., greater than or equal to 90° C. greater than or equal to 100° C., greater than or equal to 125° C., greater than or equal to 150° C., etc. In some cases, the melting temperature may be less than or equal to 150° C., less than or equal to 125° C., less than or equal to 100° C., less than or equal to 90° C., or less than or equal to 80° C. Combinations of these ranges are also possible (e.g., 60° C. to 125° C. (inclusive)).

The glycan-binding protein may also be stable to a wide range of pH conditions. For example, the glycan-binding protein may be stable at a pH of greater than or equal to 1, greater than or equal to 2, greater than or equal to 3, greater than or equal to 4, greater than or equal to 5, or greater than or equal to 6. In some embodiments, the glycan-binding protein may be stable at a pH of less than or equal to 12, less than or equal to 11, less than or equal to 10, less than or equal to 9, or less than or equal to 8. Combinations of these ranges are also possible, for example, stable within a pH of between 2-11, or within a pH between 1-12, etc.

In one embodiment, the protein is not any one of the following sequences:

(SEQ ID NO: 5)
ATVKFTYQGEEKQVDISKIKWVIRWGQHIAFKYDEGGGAAGYGWVSEK
DAPKELLQMLEKQ,

```
                                              (SEQ ID NO: 6)
ATVKFTYQGEEKQVDISKIKWVNRWGQRIYFKYDEGGGAAGYGWVSEK

DAPKELLQMLEKQ, (SEQ ID NO: 7)
ATVKYTYRGEEKRVDISKIKWVNRWGQHLAFKYDKGGGAAGYGWVSEK

DAPKELLQMLEKR, (SEQ ID NO: 8)
ATVKSTYRGEEKQVDISKIKWVIRWGQHLAFKYDEGGGAAGYGWVSEK

DAPKELLQMLEKQ, (SEQ ID NO: 9)
ATVKFTYRGEEKQVDISKIKWVNRWGQHLAFKYDVGGGAAGYGWMSEK

DAPKELLQMLEKR, (SEQ ID NO: 10)
ATVKFTYQGEEKQVDISKIKWVIRLGRTIMFKYDEGGGANGYGKVSEK

DAPKELLQMLEKQ, (SEQ ID NO: 11)
ATVKFTYQGEEKQVDISKIKWVVRLGQVIMFKYDEGGGANGYGKVSEK

DAPKELLQMLEKQ, (SEQ ID NO: 12)
ATVKFTYRGEEKQVDISKIKWVVRLGQVIMFKYGEGGGSNGYGRVSEK

DAPKELRQMLEKR,
or
                                             (SEQ ID NO: 13)
ATVKFTYRGEEKQVDISKIKWVVRLGQVIMFKYDEGGGASGYGRVSEK

DAPKELLQMLEK
```

In accordance with some embodiments, two or more proteins are linked directly to each other, or indirectly linked, e.g., by a suitable linker. Thus, in certain embodiments, the composition comprises one or more glycan-binding portions (e.g., a first glycan-binding portion and a second glycan-binding portion). The proteins can be linked, for example, C-terminus to C-terminus, N-terminus to N-terminus, C-terminus to N-terminus, or in other suitable configurations in certain instances. In some instances, the two or more proteins are joined in a linear structure. In certain cases, the two or more proteins are joined in a branched structure. In some embodiments, the two or more proteins are immobilized proximally as part of a surface immobilized array.

In some cases, two or more linked proteins may be useful to create compositions that can bind to longer glycans. For instance, a first glycan-binding portion may recognize a first binding determinant in a glycan while a second glycan-binding portion may recognize a second binding determinant in the same glycan. In this way, longer glycans comprised of more than one saccharide may be selectively bound or even sequenced in some cases, e.g., using suitable proteins such as those discussed herein. In certain embodiments, one or more of the glycan-binding portions may include protein structures such as any of these disclosed herein, for example, those generally based on Sso7d, reduced-charge variant of Sso7d (rcSso7d), etc. In some cases, such glycans may be sequenced or their identities may be determined, e.g., as discussed herein.

For example, in some cases, one or more linked proteins may be used to identify glycan structures within glycoproteins, glycolipids, glyconucleic acids, proteoglycans, or the like. For instance, glycan structures may comprise a plurality of saccharide units (e.g., Neu5Ac, Kdn, Neu5Gc, Neu, Neu2en5Ac, mannose, glucose, GlcNAc, galactose, Xyl, fucose, Leg, Pse, etc.) joined together in various configurations (e.g. by $\alpha$- or $\beta$-glycosidic linkage) or onto various structures (e.g., via N-glycosylation, O-glycosylation, etc.), and the linked protein may be able to identify two, three, or more saccharide-binding determinants within such structures.

Figure 6:
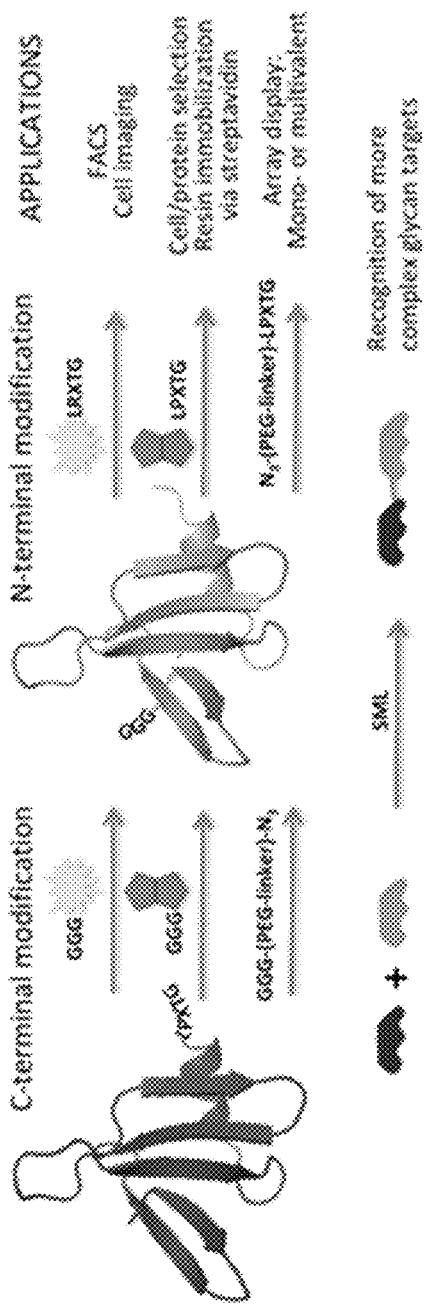
FIG. 6 illustrates conjugation of glycan-binding proteins, in accordance with various embodiments described herein.

In some embodiments, the linkage between the proteins can be accomplished indirectly. The linker, in certain embodiments, comprises a peptidic linker. For example, in FIG. 6, two proteins are linked together via an LPXTG (SEQ ID NO: 17) (or LRXTG (SEQ ID NO: 18)) sequence on one of the proteins (where X can be any amino acid) and a GGG sequence on the other protein. These may be linked together, for example, using sortase or other suitable enzymes. The LPXTG (SEQ ID NO: 17) (or LRXTG (SEQ ID NO: 18)) sequence may be found near the C-terminus of a first protein and the GGG sequence may be found near the N-terminus of a second protein, and sortase may thus covalently link the N-terminus of the first protein to a location near (within ~100 amino acids of) the C-terminus of the second protein. As another example, the peptidic linker may comprise a Gly-rich linker, e.g., a Gly-Gly linker or other Glyn linkers (n being any positive integer, e.g., 1, 2, 3, 4, 5, 6, etc.). Other amino acids may also be present in a Gly-rich linker, e.g. as in $(GGGGS)_n$ (SEQ ID NOs: 19-24).

The linker, in some instances, comprises a non-peptidic linker. A variety of non-peptidic linkers can be used, including click chemistry techniques, PEG, or the like. For example, a non-peptidic linker may comprise a polyethylene glycol (PEG) linker. For example, in FIG. 6, two proteins are linked via PEG in combination with an azide-alkyne click-chemistry linker.

According to certain embodiments, two proteins may be directly linked to each other by ligating or joining their nucleic acid sequences together such that the two proteins are expressed together. For instance, the two or more proteins may be genetically fused together.

In some cases, linking two proteins together may increase binding and/or binding selectivity to the target of interest (e.g., the monosaccharide or disaccharide-binding determinant).

In accordance with some embodiments, the composition further comprises an additional structure. For example, in some cases, the additional structure comprises a protein (e.g., a non-glycan-binding protein), enzyme, affinity tag (e.g. polyHis tag) and/or an oligonucleotide sequence, and/or small molecule (for instance, having a molecular weight of less than 2000 or 1000 Da). In some embodiments, the small molecule comprises a fluorophore. For example, in FIG. 6, one of the proteins is attached to a fluorophore.

The additional structure may be covalently attached to the protein, in certain instances. For example, in some instances, the additional structure is covalently attached to the protein via multivalent dendritic polymer backbones. According to certain embodiments, the additional structure comprises an oligomerization domain of a native protein (e.g., a non-glycan-binding protein), and the oligomerization domain is fused to the protein.

Figure 5:
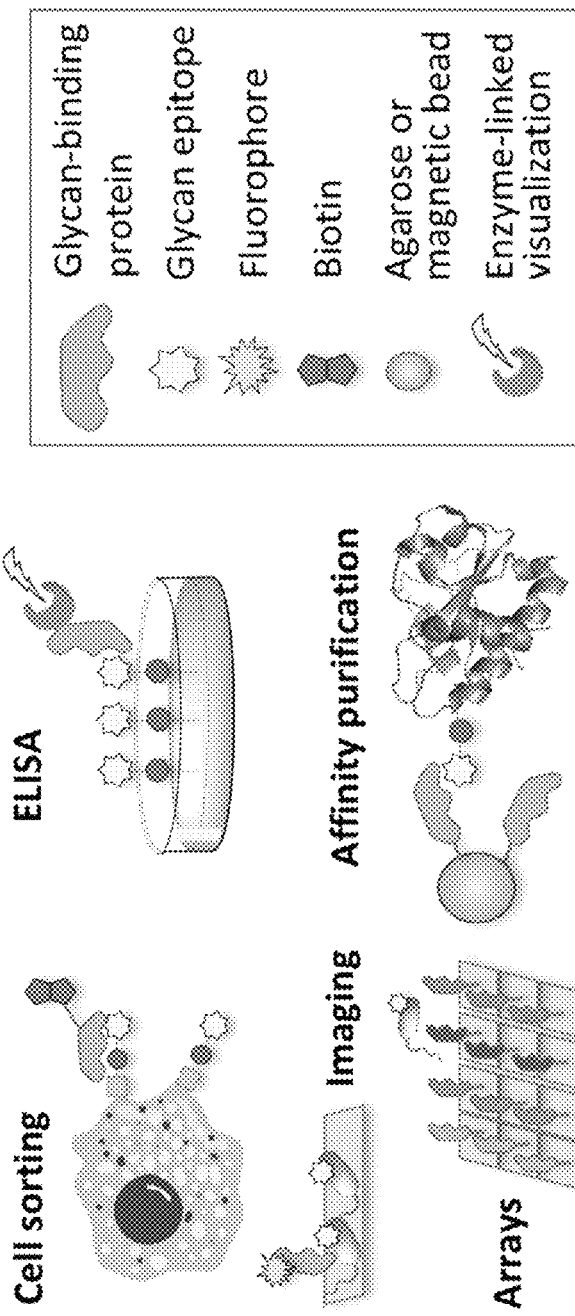
FIG. 5 illustrates functionalization and uses of the glycan-binding proteins, in accordance with some embodiments as described herein.

In some embodiments, the proteins, and compositions thereof, described herein have numerous applications, including in identification, manipulation, diagnostics, ELISAs, glycan characterization, cell selection, immunoblotting, flow cytometry, histology, imaging, arrays, affinity purification, and/or enzyme-linked visualization. For example, FIG. 5 shows some possible uses, in some cases, for the glycan-binding proteins, and compositions thereof, disclosed herein.

For instance, in some cases, the proteins disclosed herein may be useful as substitutes or analogs for antibodies and antibody-like biomolecules in immunological, therapeutic, diagnostic, or technological applications, such as flow cytometry, histology, and others. The generated proteins disclosed herein, in some instances, can be used to identify and/or manipulate a carbohydrate of interest regardless of size or composition.

Many carbohydrates or biomolecules play significant roles in various diseases, and systems and methods for determining glycans, e.g., using glycan-binding proteins such as those discussed herein, may be useful for identifying, characterizing, or sequencing such glycans. As another example, such proteins could be used to determine human cancer-binding determinants, bacterial glycans, or the like.

In certain embodiments, proteins such as those disclosed herein can be attached to other groups, providing a vast array of applications. For example, in some cases, proteins such as those disclosed herein can be attached to a fluorophore. This could be useful, for example, in imaging of a glycan-binding determinant of interest (or molecules containing the glycan-binding determinant of interest). As another example, in certain instances, a protein can be attached to a molecule such as biotin. This could be useful, for example, various in cell selection applications. According to yet another example, a protein disclosed herein can be attached to a bead, such as an agarose bead or a magnetic bead. This could be useful, for example, in affinity purification of glycan-binding determinants of interest (or molecules containing the glycan-binding determinant of interest).

According to certain embodiments, the proteins (and compositions thereof) described herein have various advantages. For example, in some embodiments, the methods described herein can be used to generate a protein specific for any desired target, which can be useful, for example, where there are no native binders of that target. In some cases, the proteins described herein may be more stable (e.g., to temperature or pH) than other binders of the desired target. Moreover, in some instances, the proteins described herein are small enough that they can recognize single-atom differences between molecules (e.g., sugars), which may provide higher specificity for a target of interest than other binders, and/or which may prevent or reduce steric hindrance.

Without wishing to be bound by theory, it is believed that, in certain embodiments, generating a glycan-binding protein from a protein that does not typically bind sugars (e.g., from a DNA-binding protein or a protein-binding protein) can improve selectivity for the glycan of interest, for instance, as there is no possibility of lingering native sugar-binding functionality for a different sugar. Similarly, in some embodiments, the proteins described herein have higher binding constants for the target of interest than other binders. Further, in certain cases, the proteins described herein can be easily attached to one another (e.g., through sortase-mediated ligation or genetic fusion) or to other groups (e.g., fluorophores or chemical handles) for easy functionalization.

The following examples are intended to illustrate certain embodiments of the present invention, but do not exemplify the full scope of the invention.

Example 1

This example describes an archaeal DNA binding protein to bind and manipulate glycans, or carbohydrates and carbohydrate-containing biomolecules. As discussed herein, small DNA-binding proteins (based on Sso7d from *Sulfolobus solfataricus*) can be engineered using directed evolution to bind and specifically recognize targeted monosaccharides (e.g. hexose, heptulose, octulosonic and nonulosonic derivatives), disaccharides, and other more complex carbohydrates, although wild-type Sso7d is not able to bind to any glycans. As such, the engineered proteins may be able to substitute for antibody and antibody-like biomolecules in various immunological, diagnostic, and/or technological roles, such as flow cytometry, histology, and others. The proteins directly can also be used as a protein reagent capable of identifying and manipulating a carbohydrate of interest regardless of size or composition, filling a long-standing need in the glycosciences and medicine. Importantly, the proteins can also be assembled, e.g., in a "mix-and-match" fashion, to create custom reagents.

In some embodiments, the engineered proteins can tightly bind single copies of a sugar and distinguish single differences at the atomic level. The proteins may also be capable of straightforward chemical functionalization, do not require specialized training for use, and can be linked in some cases to assemble a reagent capable of specifically recognizing and manipulating complex oligosaccharide structures.

This example describes the preparation of glycan-binding proteins from an Sso7d library. The initial Sso7d library was prepared based on the methods described in Traxlmayr, M. W. et al. *J. Biol. Chem.* 2016, 291(43), 22496-22508. This library was prepared from a reduced charge-variant of Sso7d, a native DNA binder. Nine surface-exposed residues on one face of a reduced-charge variant of Sso7d were randomized with 18 different amino acids (all of the 20 naturally occurring amino acids, except the original amino acid itself and cysteine to avoid any sulfide groups) to generate a combinatorial library of approximately $10^9$ Sso7d variants. This was accomplished by PCR elongation and amplification of the SSo7d gene, followed by electroporation of PCR fragments and linearized vectors into yeast.

Sso7d has the following sequence:

(SEQ ID NO: 2)
ATVKFKYKGEEKQVDISKIKKVWRVGKMISFTYDEGGGKTGRGAVSEK

DAPKELLQMLEKQK while the reduced-charge variant of Sso7d has the following sequence:

(SEQ ID NO: 1)
ATVKFTYQGEEKQVDISKI<u>KKV</u>WRVG<u>QMI</u>SFTYDEGGG<u>ATG</u>RGAVSEK

DAPKELLQMLEKQ, where the underlining indicates the nine residues that were randomized.

After a Sso7d library was prepared as discussed above, the Sso7d library was then panned in these experiments via yeast-surface display (YSD) selections with magnetic bead-immobilized glycans for evolution of glycan binders using established techniques for yeast display. The beads were Dynabeads, which are made of polystyrene with a ferrous core. The bead-immobilized glycans used included a dihexose (e.g. Galβ1-3GalNAcα, the TF or Thomsen-Friedenrich antigen) or a nonulosonic acid (e.g. Neu5Ac.) Glycans were added by covalent chemical conjugation via a tosyl moiety or by non-covalent interactions between a biotin molecule on the glycan and a streptavidin tetramer on the bead surface.

Variants that bound glycans of interest with higher binding and/or binding selectivity were selected. In each bead selection (three or more were performed), yeast cells displaying Sso7d were selected by (i) their ability to stay bound to magnetic beads through rigorous, iterative rounds of washing, agitation, and/or presence of competitors, and/or (ii) their inability to stay bound on beads displaying undesired molecules, such as other saccharides or polymeric backbones. Once selected by bead selections and FACS sorts, Sso7d variants on yeast surfaces were required to bind polymeric sugar reagents (sugar-PAA-FITC) in solution state and any variants that did this moved forward in the process.

The selected variants were then mutated further. Mutated residues were no longer limited to the 9 surface exposed residues in order to allow for more possibilities for favorable properties to be found, by allowing mutations throughout the protein. FACS sorting allowed identification and physical selection of the tightest binding yeast cells, and these were propagated and their expression vectors removed for DNA sequencing. This DNA material was then used in any further mutagenesis by error-prone PCR or by rational site-directed mutagenesis. The process (i.e., mutating and selecting) was repeated numerous times.

After variants of proteins exhibiting desired binding and/or binding selectivities were obtained, the genes of the Sso7d variants of interest were amplified from yeast expression vectors by PCR, and the resulting PCR fragments were cloned into an *E. coli* expression vector bearing an affinity tag. Proteins were overexpressed in *E. coli* bearing the vector and the proteins were purified by affinity chromatography and characterized by SDS-Page for identity and purity.

In some cases, the variants were then conjugated to other variants (of the same or different types) and to other structures (e.g., fluorophores). For example, some expressed Sso7d variants were elongated to contain the sequence LPXTG (SEQ ID NO: 17). They were then ligated via sortase-mediated ligation to bear short peptides carrying a biotin molecule. They have also been sortagged to contain the FITC fluorophore. Sso7d variants have been attached to each other via genetic fusion, but also are attached by sortase-mediated mediated ligation.

Non-limiting examples of Sso7d variants that can bind to glycans are shown below. The exemplary variants in Sequence List 1 were engineered to bind one or more nonulsonic acids, while the exemplary variants in Sequence List 2 were engineered to bind one or more dihexoses. The disaccharides (or disaccharides motifs within trisaccharides) bound by variants in Sequence List 1 and 2 are shown in FIGS. 9A-9F. Every variant listed in Sequence List 1 and Sequence List 2 bound at least one disaccharide (or disaccharide motif within a trisaccharide) in FIGS. 9A-9F. These variants are not shown in any particular order.

Example 2

This example describes some of the glycan-binding proteins of Example 1. The protein scaffold (SEQ ID NO: 1) of Example 1 is a reduced-charge variant of Sso7d, which is a native DNA binder. The protein scaffold was used to generate the glycan-binding proteins. It had 63 residues and a melting temperature of 98° C. The protein scaffold was stable to prolonged exposure to pH values with the range of 0.3-12.5 and was free of disulfides. The protein scaffold was compatible with yeast surface display, high-yield protein expression in *E. coli*, and functionalization. The protein scaffold formed an SH3-domain-like fold with five beta (β)-strands and an alpha (α)-helix at the C-terminus.

Figure 4:
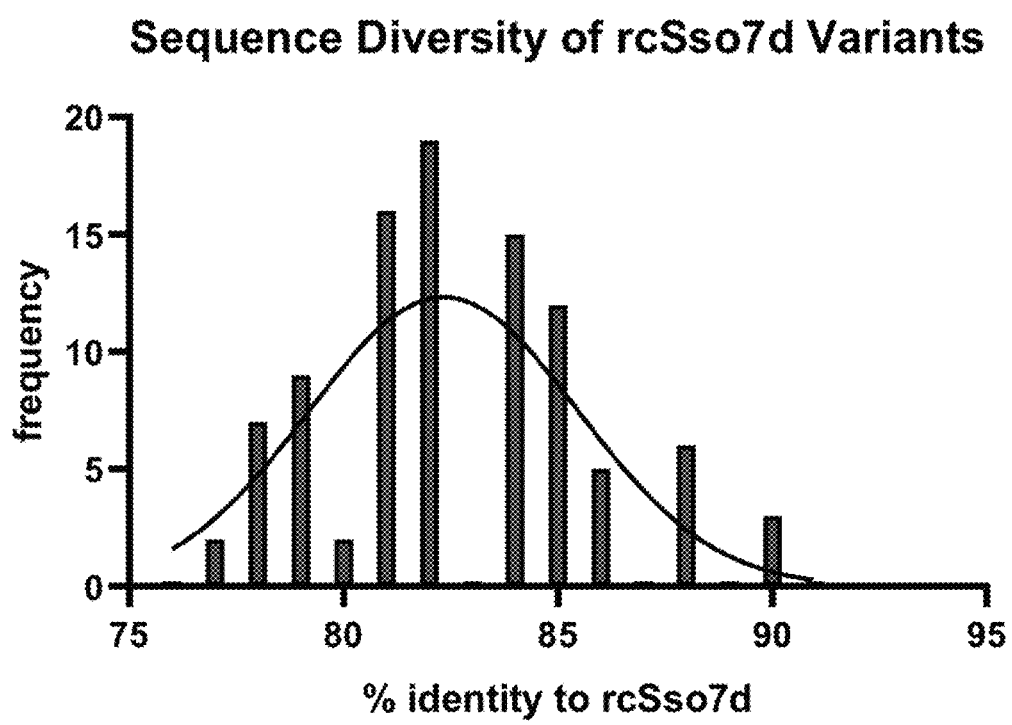
FIG. 4 illustrates, in accordance with certain embodiments, a histogram of the percent identity of the glycan-binding proteins in Sequence List 2 with rcSso7d.

The glycan-binding proteins that were found in Example 1 were generally stable to the described biochemical manipulations and were predicted to be well-folded both on yeast surfaces and as soluble expressed proteins based the observed binding properties. Anecdotally it also is known that proteins that are efficiently expressed on yeast cell surfaces must be well-folded. In addition, the glycan-binding proteins had sequences that diverged significantly from the protein scaffold. FIG. 4 shows a histogram of the number of variants in Sequence List 2 that bind glycans versus percent homology in sequence compared to the original protein scaffold (the reduced-charge variant of Sso7d, or rcSso7d). Notably, these sequences are significantly different than the protein scaffold, with the most divergent sequences having approximately 68-69% homology. For example, these histograms include the following sequences that have 68.852% homology to the protein scaffold:

```
                                         (SEQ ID NO: 13)
ATVKFTYRGEEKQVGVSRVKSVHRIGQWIKFWYDEGSGAYGRGYVSEK

DAPEELLQMLEKRGSEQKLISEEDL (SEQ ID NO: 394)
ATVKFTYRGEEKQVGISRIRSVHRIGQWIKFWYDEGSGACGRGYVSEK

GAPKELLQMLGKRGSEQKLISEEDL (SEQ ID NO: 395)
ATVKFTYRGKEKRVGVSRIKSVRRIGQWIKFWYDEGSGAYGRGYVSEK

DAPKELLQMLEKRGSEQKLISEEDL (SEQ ID NO: 396)
ATVKFTYRGEEKQVGINRIKSVHRIGQWIKFWYDEGSGAYGRGYVSGK

DAPKELLRMLEKRGSEQKLISEEDL
```

Despite the differences in sequence, these variants are all predicted to form an SH3-domain-like fold with five beta (β)-strands and an alpha (al-helix at the C-terminus. Other glycan-binding proteins with even more divergence are also predicted to exhibit a similar SH3-domain-like fold with five beta (β)-strands and an alpha (α)-helix at the C-terminus.

Example 3

This example describes some glycan-binding proteins from Example 1.

Some of the variants that were generated demonstrated high specificity for a target of interest and could distinguish small points of differences between molecules that were targeted and other, non-target molecules having similar structures. For instance, in this example, variants were evolved to bind Galα1-3GalNAcα (TF antigen), as discussed in Example 1. These variants demonstrated $K_D$ values for the TF antigen of 3 nM to 150 nM. These variants were studied with biolayer interferometry (BLI).

FIGS. 2A-2C show the structure of the TF antigen compared to the structures of Galα1-3GalNAcα and GalNAcα1-3GalNAcα, with arrows pointing to the stereocenters and functional groups that vary from the TF antigen. Specifically, Galα1-3GalNAcα differs from the TF antigen in having a substituent in the axial position instead of an equatorial position. GalNAcα1-3GalNAcα has an additional differentiation, in that a hydroxyl group is replaced by an N-acetamide substituent.

Figure 2D:
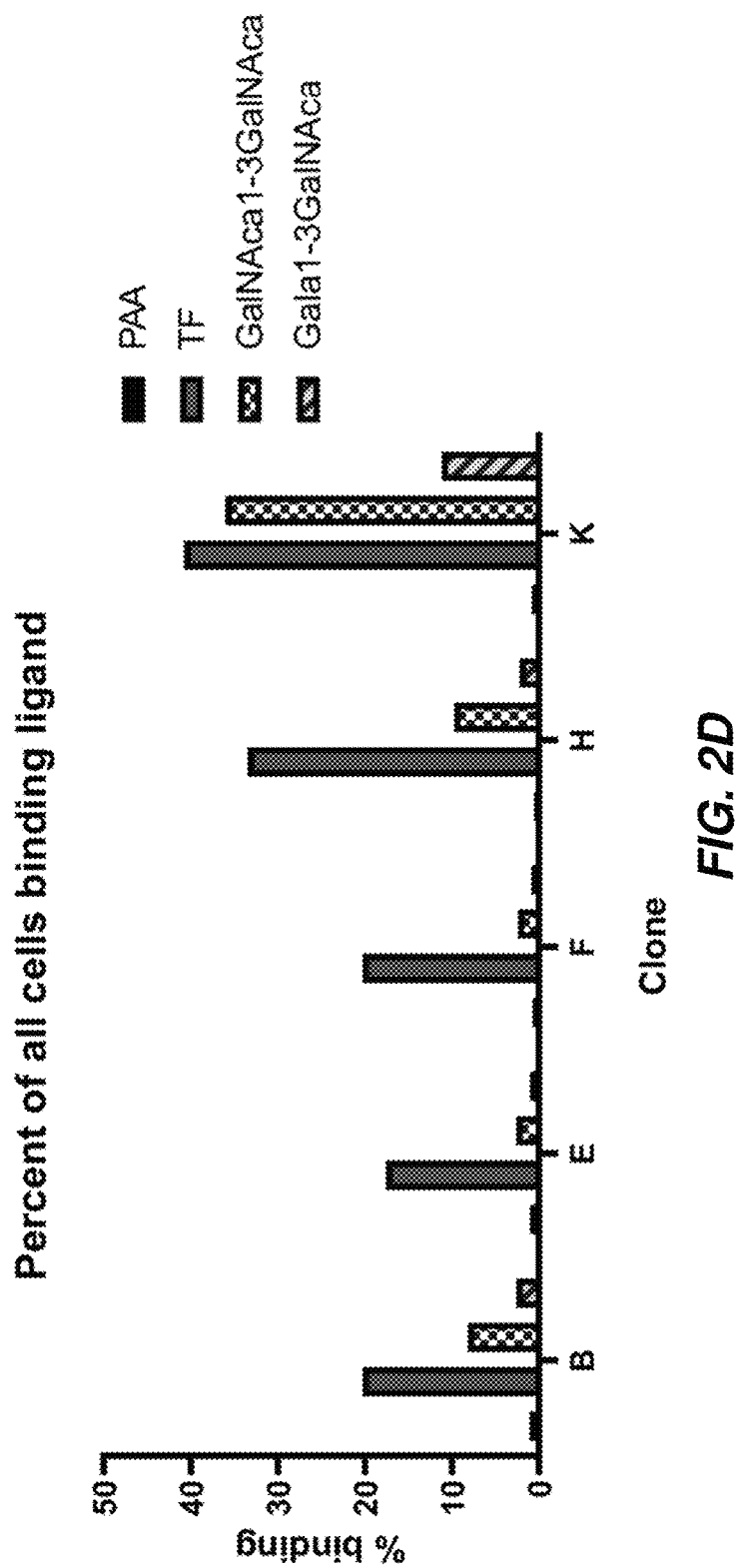
FIG. 2D illustrates, in accordance with certain embodiments, the percent binding of the three compounds of FIGS. 2A-2C and PAA-FITC (the control) for five different glycan-binding proteins.

FIG. 2D shows the percent binding of these three compounds and a sugar-polyacrylic acid (PAA)-FITC conjugate as a control for five different variants that were identified in these experiments. This binding was determined by analytical flow cytometry, wherein fluorescently labeled yeast and fluorescently labeled sugar-PAA-FITC were co-localized. These five variants (from Sequence List 2) have the following sequences:

```
                                            (SEQ ID NO: 397)
ATVKFTYQGEEKQVDISKIKIVYRWGQRISFIYDEGGGARGYGRVSEKDA

PKELLQMLEKQGSEQKLISEEDL
(arbitrarily labeled clone B)

(SEQ ID NO: 398)
ATVKFTYQGEEKQVDISKIKHVRRWGQWIWFIYDEGGGAKGWGGVSEKDA

PKELLQMLEKQGSEQKLISEEDL
(arbitrarily labeled clone E)

(SEQ ID NO: 399)
ATVKFTYQGEEKQVDISKIKYVRRWGQYIWFGYDEGGGARGYGYVSEKDA

PKELLQMLEKQGSEQKLISEEDL
(arbitrarily labeled clone F)

(SEQ ID NO: 400)
ATVKFTYQGEEKQVDISKIKRVYRYGQWIWFRYDEGGGAYGGGWVSEKDA

PKELLQMLEKQGSEQKLISEEDL
(arbitrarily labeled clone H)

(SEQ ID NO: 401)
ATVKFTYQGEEKQVDISKIKSVSRWGQAIIFRYDEGGGAKGKGSVSEKDA

PKELLQMLEKARIRTKAYF
(arbitrarily labeled clone K).
```

Notably, despite the small differences between the compounds in FIGS. 2A-2C, it was found that all of these variants preferentially bound the TF antigen versus the other compounds and the control. Thus, these data illustrate that proteins can be engineered to preferentially bind to specific sugars. Additionally, the variants differed from each other by 6 or fewer amino acids within the binding region.

Figure 2E:
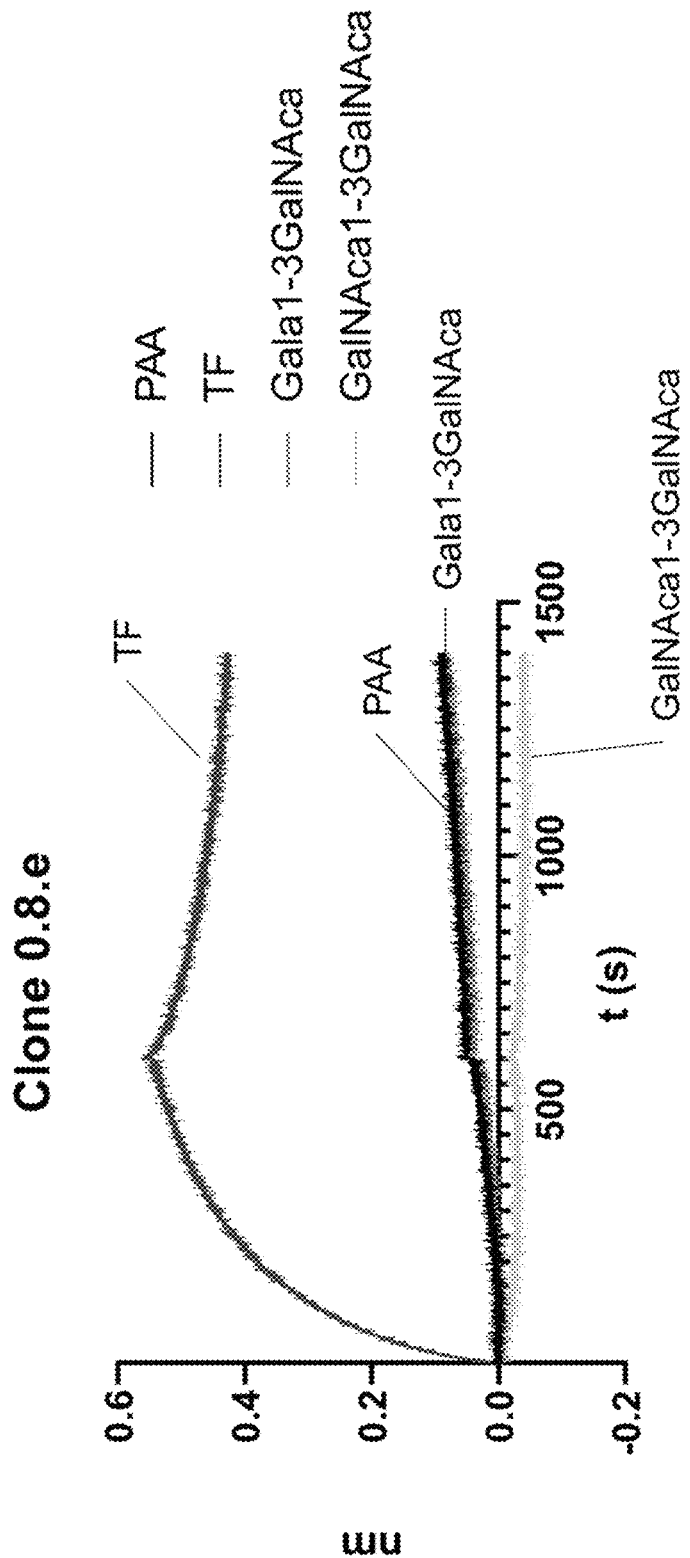
FIG. 2E illustrates biolayer interferometry traces of a glycan-binding protein in accordance with some embodiments.

FIG. 2E shows the biolayer interferometry traces for clone E. Clone E was immobilized on a Ni-NTA tip and dipped into a 1 uM solution of the sugar of interest. The traces show an increase in nm as sugar starts binding to protein on the tip, then a decrease in nm as the tip is moved from the sugar solution to buffer only. From this data, a curved was fitted and the binding affinity was determined from the rate of association and dissociation. FIG. 2E demonstrates that clone E bound to the TF antigen but did not bind to the negative control (PAA) and the other related disaccharides provided.

Example 4

This example describes certain glycan-binding proteins from Example 1. Some of the variants that were generated in Example 1 demonstrated high specificity for a target of interest and could distinguish small points of differences between molecules that were targeted and other, non-target molecules having similar structures. For instance, in this example, variants were evolved to bind sialic acid (Neu5Ac), as discussed in Example 1. These variants were then studied with flow cytometry and in particular, were determined to preferentially bind to Neu5Ac (sialic acid) relative to Neu5Gc. These variants (from Sequence List 1) have the following sequences:

```
                                            (SEQ ID NO: 402)
ATVKFTYRGEEKQVGISRIKSVRRIGQWIKFWYDEGSGAYGRGYVSEKDA

PKELLQMLEKR (arbitrarily labeled clone A4)

(SEQ ID NO: 403)
ATVKFTYRGEEKQVGISRIKSVRRIGQWIKFWYDEGSGAYGRGYVSGKDA

PKELLQMLEKR (arbitrarily labeled clone B5)

(SEQ ID NO: 404)
ATVKFTYRGGEKQVGISRIKSVRRIGQWIKFWYDEGSGAYGRGYVSEKDA

PKELLQMLEKR (arbitrarily labeled clone B6)

(SEQ ID NO: 405)
ATVKFTYRGEEKQVGISRIKSVHRIGRWIKFWYDEGSGAYGRGYVSEKDA

PKELLQMLEKR (arbitrarily labeled clone B8)

(SEQ ID NO: 406)
ATVKFTYRGEEKQVGISRIKSVHRIGQWIKFWYDEGSGAYGRGYVSKKDA

PKELLQMLEKR (arbitrarily labeled clone C11)
```

To analyze this specificity, yeast cells bearing the HA-epitope tag and displaying Sso7d variant Clone B5, for example, on their surface were labeled using fluorescent anti-HA antibody. These were provided 500 nM of the desired sugar-PAA-FITC for 1 hour, then analyzed by analytical flow cytometry for co-localization of both fluorophores, indicating glycan binding. Specific binding can be observed by the percentage of cells binding Neu5Ac versus Neu5Gc or PAA-FITC alone. Cells were gated in flow cytometry parameters to ensure single-cell analysis of live cells presenting Sso7d on their surface. As an example, the binding constant for Clone B5, as determined independently by BLI with soluble, expressed Clone B5, was 25-30 nM.

FIGS. 3A-3B show the structures of sialic acid (Neu5Ac) (FIG. 3A) and Neu5Gc (FIG. 3B). These binding determinants differ by one hydroxyl group.

Figure 3E:
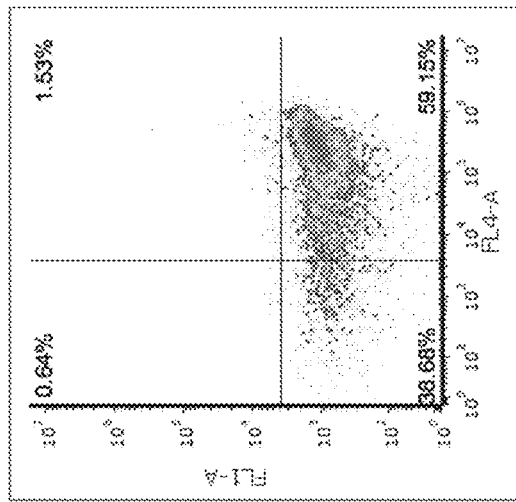
FIGS. 3C-3E illustrate flow cytometry results for sialic acid-PAA-FITC (FIG. 3C), NeuN5Gc-PAA-FITC (FIG. 3D), and PAA-FITC (FIG. 3E) for a glycan-binding protein, in accordance with certain embodiments.
Figure 3D:
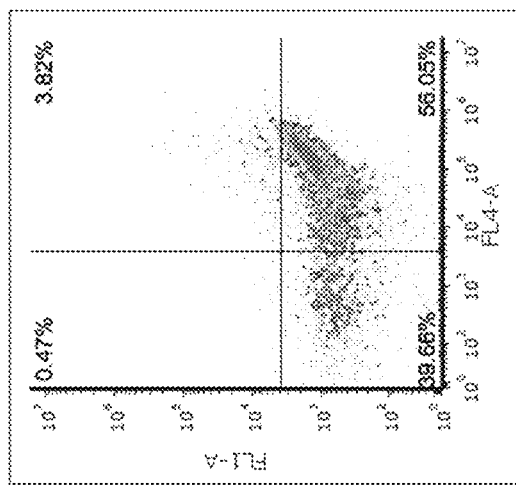
Figure 3C:
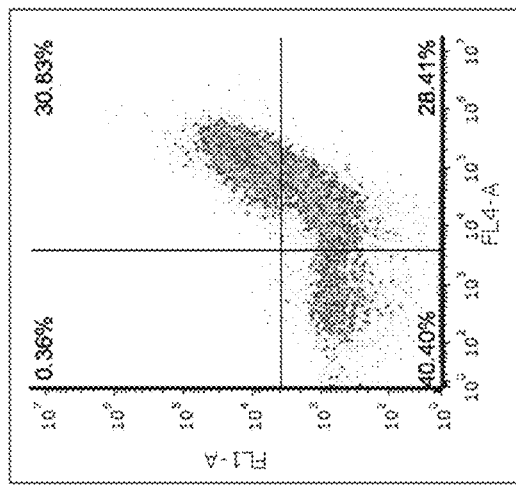

FIGS. 3C-3E show the flow cytometry results for Neu5Ac-PAA-FITC (FIG. 3C), Neu5Gc-PAA-FITC (FIG. 3D), and the control PAA-FITC (FIG. 3E) for clone B5. These results show that the variants tested preferentially bound to sialic acid relative to Neu5Gc-PAA-FITC or PAA-FITC. Similar results have been attained for other glycan-binding proteins from Example 1, such as clones A4, B6, B8, and C11.

Example 5

This example describes testing of glycan-binding proteins described herein against various glycans in flow cytometry binding studies.

Figure 10A:
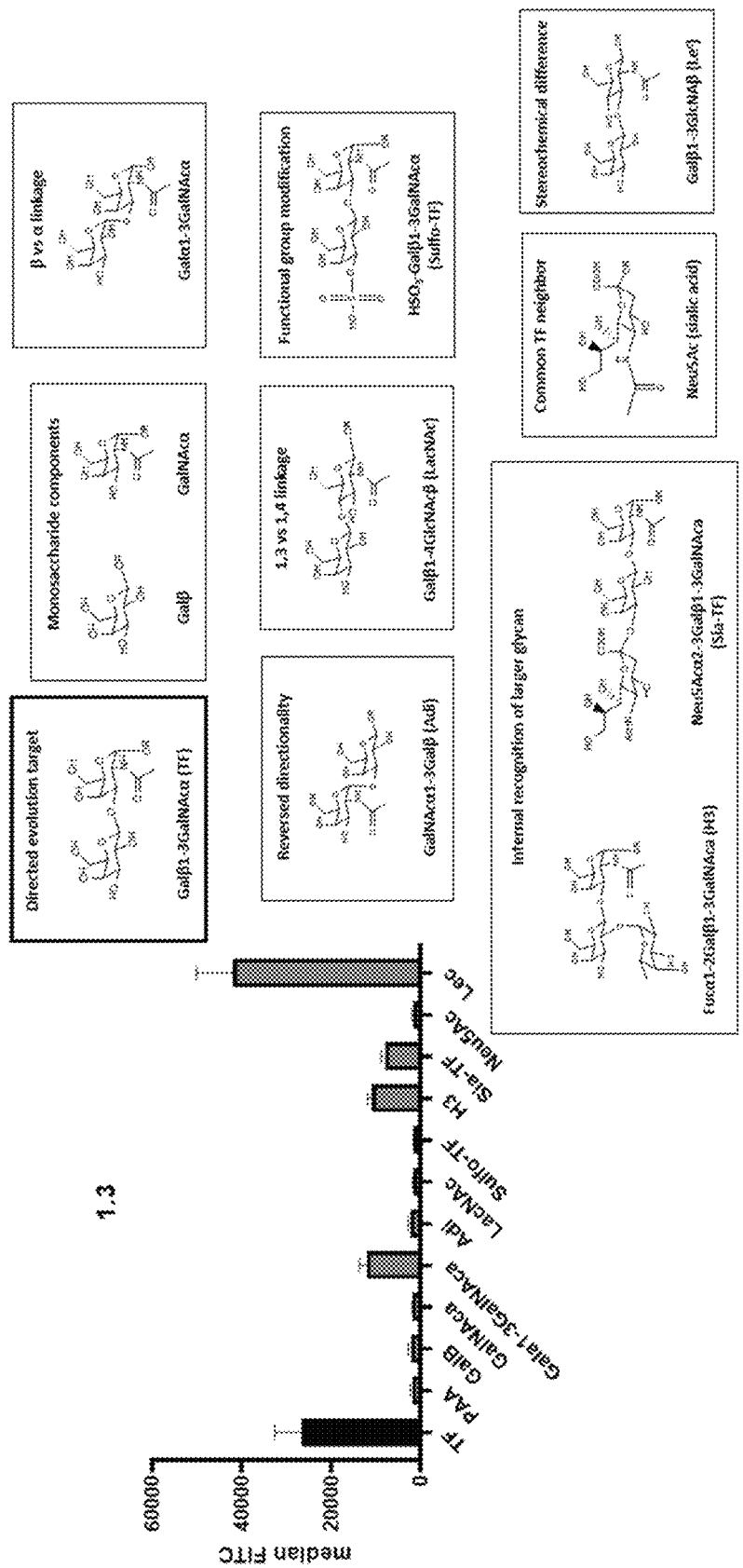
FIG. 10A illustrates median fluorescence intensity of a binding study of an embodiment described herein tested against various glycans.
Figure 10B:
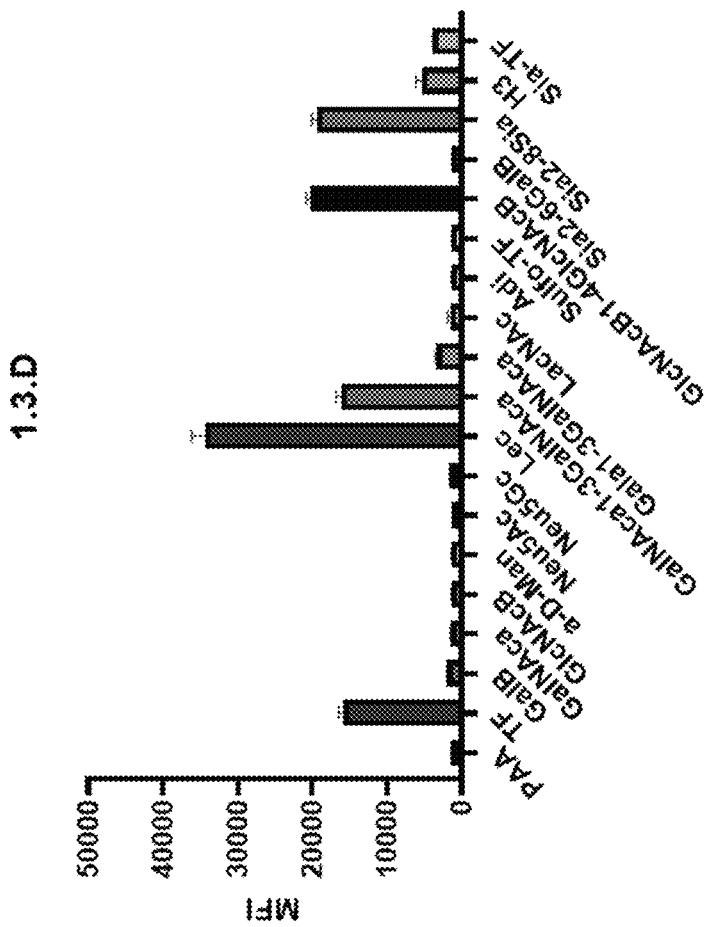
FIG. 10B illustrates binding specificity of an embodiment described herein tested against various glycans.
Figure 10C:
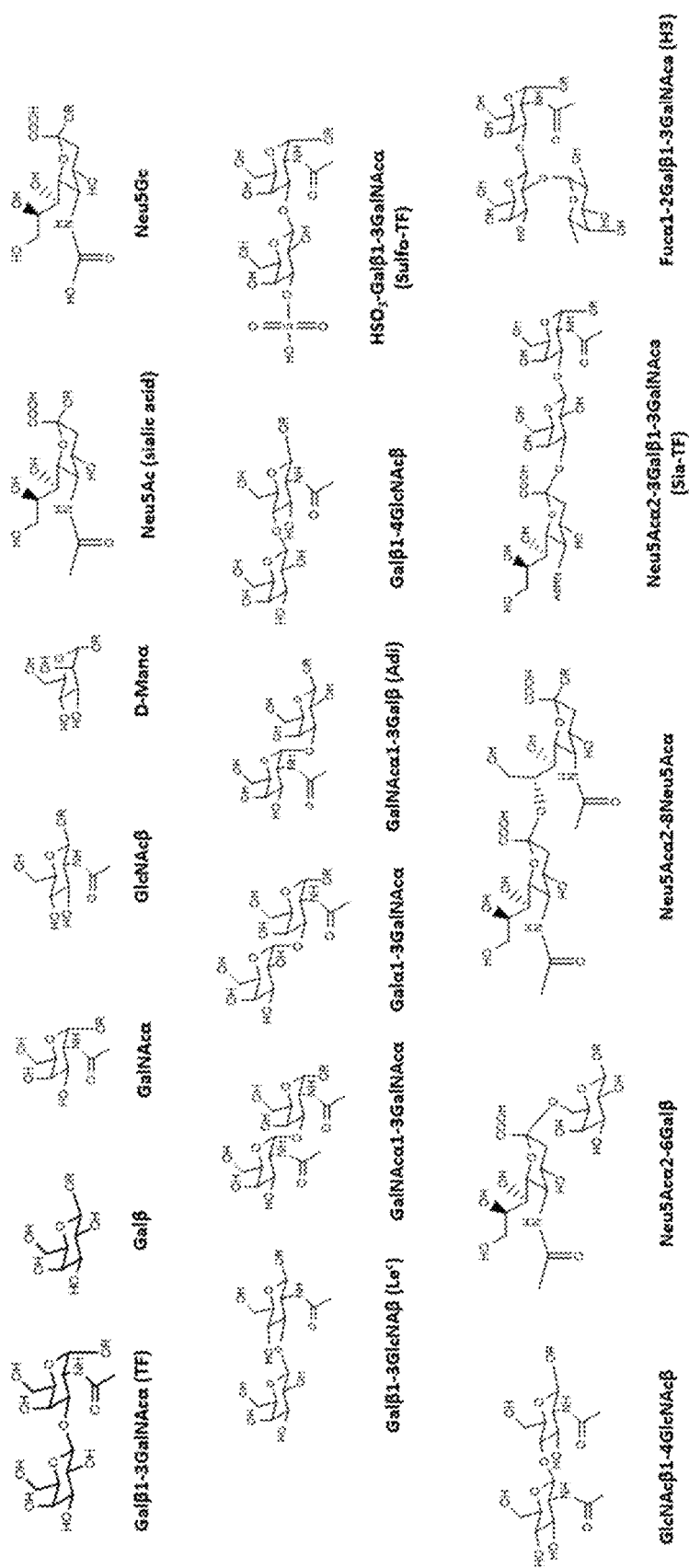
FIG. 10C illustrates structures of all glycans tested for binding.
Figure 10D:
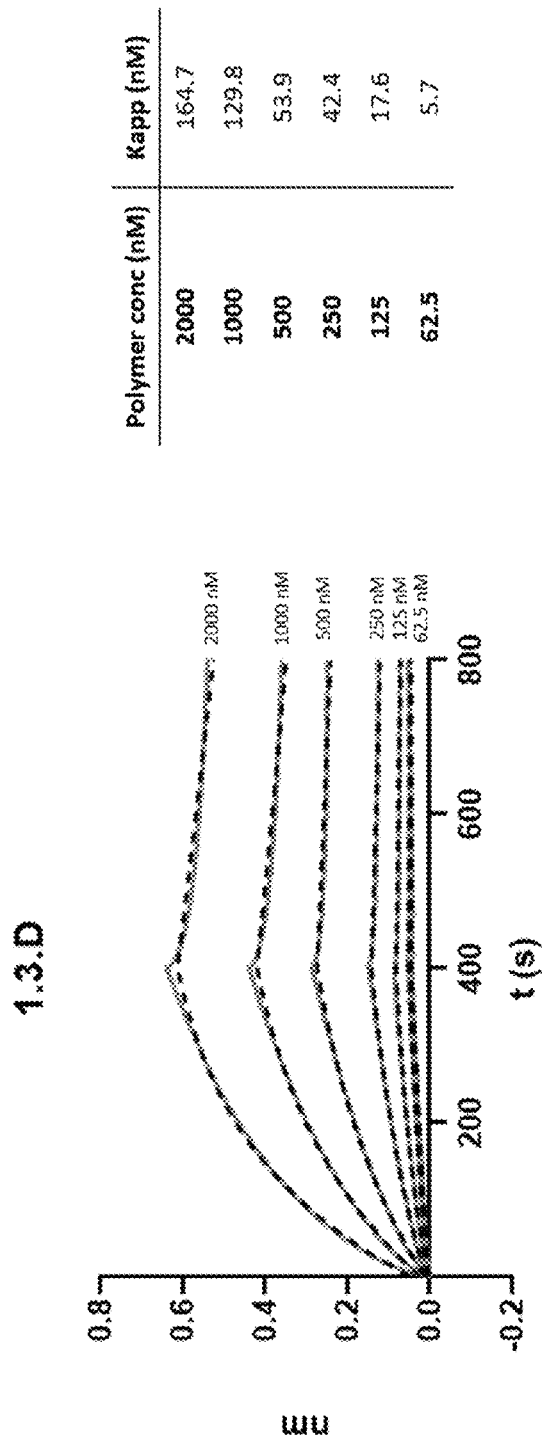
FIG. 10D illustrates biolayer interferometry traces of an embodiment described herein with apparent Kd values calculated.

A mixed library of clones was generated based upon the directed evolution target Galβ1-3GalNAcα (TF). Based upon the directed evolution target Galβ1-3GalNAcα (TF), glycans with structural variations were chosen for a flow cytometry study in which binding behavior was examined (FIG. 10C). Glycans were chosen that possess atom-level differences to each other, including but not limited to: glycans that differ by 1 inverted stereocenter (e.g., GlcNAc vs. GalNAc), glycans with sidechains on neighboring carbon atoms (e.g., OH— on C3 vs. OH— and C4), disaccharides that are comprised of identical monosaccharides whose positions have been flipped (e.g., Gal-GalNAc vs. GalNac-Gal) and others. These glycans with structural variations (FIG. 10C) were all chosen to highlight the ability of this scaffold at distinguishing small structural differences essential to glycan recognition in nature. These results show that only glycan Galβ1-3GlcNAβ (Lec) demonstrated greater binding than the directed evolution target Galβ1-3GalNAcα for a mixed library of clones (FIG. 10A). In addition to the previously discussed binding study, a flow cytometry study in which the binding specificity was studied was carried out, and results show that glycans Galβ1-3GlcNAβ (Lec), GlcNAcβ 1-4GlcNAcβ, and Sia2-8Sia had higher binding specificities than that of TF, while GalNAcα1-3GalNAcα had comparable binding specificity to TF (FIG. 10B). Biolayer interferometry was also used to calculate apparent $K_D$ values at varying polymer concentrations for Clone 1.3.D (FIG. 10D), which has the following sequence:

(SEQ ID NO: 416)
ATVKFTYRGEEKQVDISKIKYVRRWGQYIWFGYDEGGGARGYGY

VSETDAPELLLQMLEKQ (Clone 1.3.D).

Figure 11A:
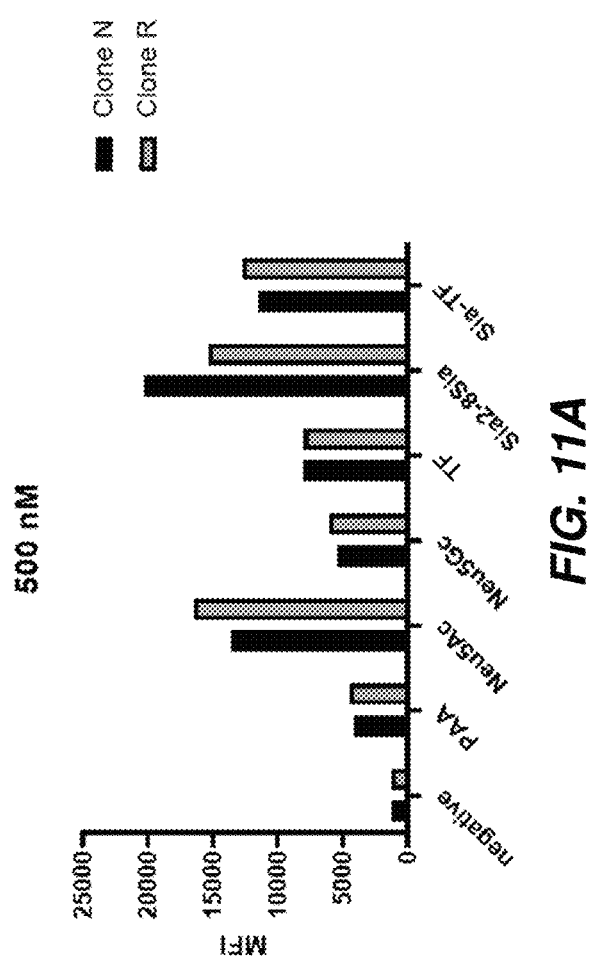
FIG. 11A illustrates the binding specificity of embodiments described herein.

Binding specificity was also tested for various glycans with Clone N and Clone R (FIG. 11A), which have the following sequences:

(SEQ ID NO: 417)
ATVKFTYRGEGKqVGISRIKSVRRIGQWIKFWYDEGSGAYGRGY

VSGKDAPKELLQMLEKR (Clone N)

(SEQ ID NO: 418)
ATVKFTYRGEEKQVGISRIKSVRRIGRWIKLWYDEGSGAYGRGY

VSGKDAPKELLQMLEKR (Clone R)

Figure 11B:
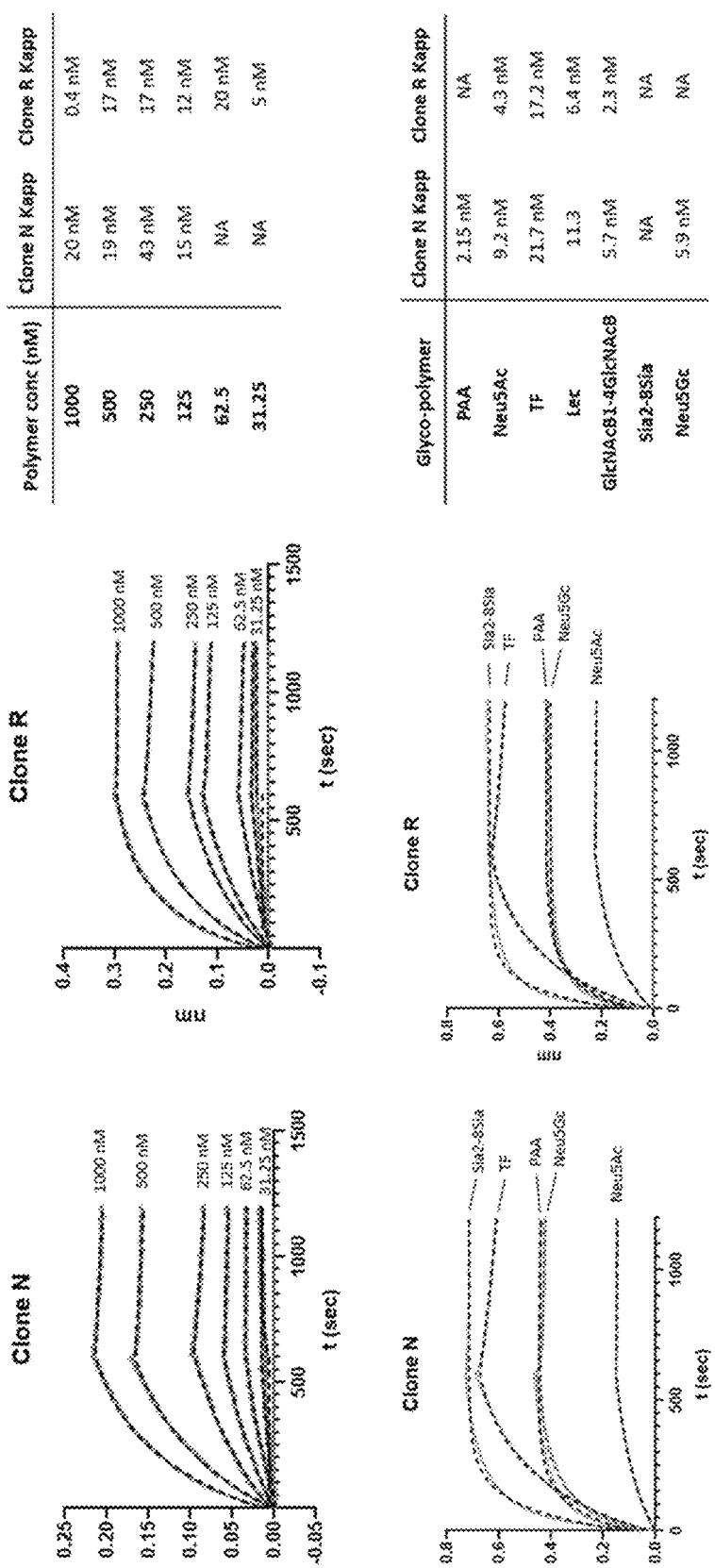
FIG. 11B illustrates biolayer interferometry traces of embodiments described herein with apparent Kd values calculated.

The results indicate that glycan Sia2-8Sia showed the most difference in preferential binding, as evidenced by the median fluorescence intensity values for Clone N and Clone R binding. Biolayer interferometry was used to calculate $K_D$ values for Clone N and Clone R at varying polymer concentrations and using various glycol-polymers (FIG. 11B). These biolayer inferometry results measure average apparent $K_D$ values for Clone N and Clone R to be 24 nM and 12 nM respectively, suggesting these scaffolds bind glycans 10- to 100-fold more tightly than glycan-binding proteins occurring in nature (i.e. lectins and mAbs).

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Some embodiments may be embodied as a method, of which various examples have been described. The acts performed as part of the methods may be ordered in any suitable way. Accordingly, embodiments may be constructed in which acts are performed in an order different than illustrated, which may include different (e.g., more or less)

acts than those that are described, and/or that may involve performing some acts simultaneously, even though the acts are shown as being performed sequentially in the embodiments specifically described above. In some cases, the methods may also have intervening steps in addition to those described.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

```
                            SEQUENCE LISTING

Sequence total quantity: 418
SEQ ID NO: 1            moltype = AA  length = 61
FEATURE                 Location/Qualifiers
REGION                  1..61
                        note = Synthetic Polypeptide
source                  1..61
                        mol_type = protein
                        organism = synthetic construct
SEQUENCE: 1
ATVKFTYQGE EKQVDISKIK KVWRVGQMIS FTYDEGGGAT GRGAVSEKDA PKELLQMLEK   60
Q                                                                  61

SEQ ID NO: 2            moltype = AA  length = 62
FEATURE                 Location/Qualifiers
source                  1..62
                        mol_type = protein
                        organism = Sulfolobus solfataricus
SEQUENCE: 2
ATVKFKYKGE EKQVDISKIK KVWRVGKMIS FTYDEGGGKT GRGAVSEKDA PKELLQMLEK   60
QK                                                                 62

SEQ ID NO: 3            moltype = AA  length = 62
FEATURE                 Location/Qualifiers
REGION                  1..62
                        note = Synthetic Polypeptide
VARIANT                 21..27
                        note = X can be any naturally occurring amino acid
VARIANT                 21..27
                        note = Xs cannot sequentially be KKVWRVG
VARIANT                 28..34
                        note = X can be any naturally occurring amino acid
VARIANT                 28..34
                        note = Xs cannot sequentially be QMISFTY
VARIANT                 40..46
                        note = X can be any naturally occurring amino acid
VARIANT                 40..46
                        note = Xs cannot sequentially be ATGRGAV
source                  1..62
                        mol_type = protein
                        organism = synthetic construct
SEQUENCE: 3
ATVKFTYQGE EKQVDISKIK XXXXXXXXX XXXXDEGGGX XXXXXXSEKD APKELLQMLE    60
KQ                                                                 62

SEQ ID NO: 4            moltype = AA  length = 62
FEATURE                 Location/Qualifiers
REGION                  1..62
                        note = Synthetic Polypeptide
VARIANT                 22
                        note = X can be any naturally occurring amino acid
VARIANT                 22..45
                        note = Xs cannot simultaneously be K, W, V, M, S, T, T, R,
                         and A, sequentially
VARIANT                 24
                        note = X can be any naturally occurring amino acid
VARIANT                 26
                        note = X can be any naturally occurring amino acid
VARIANT                 29
                        note = X can be any naturally occurring amino acid
VARIANT                 31
                        note = X can be any naturally occurring amino acid
VARIANT                 33
```

```
                        note = X can be any naturally occurring amino acid
VARIANT                 41
                        note = X can be any naturally occurring amino acid
VARIANT                 43
                        note = X can be any naturally occurring amino acid
VARIANT                 45
                        note = X can be any naturally occurring amino acid
source                  1..62
                        mol_type = protein
                        organism = synthetic construct
SEQUENCE: 4
ATVKFTYQGE EKQVDISKIK KXVXRXGQXI XFXYDEGGGA XGXGXVSEKD APKELLQMLE     60
KQ                                                                   62

SEQ ID NO: 5            moltype = AA  length = 61
FEATURE                 Location/Qualifiers
REGION                  1..61
                        note = Synthetic Polypeptide
source                  1..61
                        mol_type = protein
                        organism = synthetic construct
SEQUENCE: 5
ATVKFTYQGE EKQVDISKIK WVIRWGQHIA FKYDEGGGAA GYGWVSEKDA PKELLQMLEK     60
Q                                                                    61

SEQ ID NO: 6            moltype = AA  length = 61
FEATURE                 Location/Qualifiers
REGION                  1..61
                        note = Synthetic Polypeptide
source                  1..61
                        mol_type = protein
                        organism = synthetic construct
SEQUENCE: 6
ATVKFTYQGE EKQVDISKIK WVNRWGQRIY FKYDEGGGAA GYGWVSEKDA PKELLQMLEK     60
Q                                                                    61

SEQ ID NO: 7            moltype = AA  length = 61
FEATURE                 Location/Qualifiers
REGION                  1..61
                        note = Synthetic Polypeptide
source                  1..61
                        mol_type = protein
                        organism = synthetic construct
SEQUENCE: 7
ATVKYTYRGE EKRVDISKIK WVNRWGQHLA FKYDKGGGAA GYGWVSEKDA PKELLQMLEK     60
R                                                                    61

SEQ ID NO: 8            moltype = AA  length = 61
FEATURE                 Location/Qualifiers
REGION                  1..61
                        note = Synthetic Polypeptide
source                  1..61
                        mol_type = protein
                        organism = synthetic construct
SEQUENCE: 8
ATVKSTYRGE EKQVDISKIK WVIRWGQHLA FKYDEGGGAA GYGWVSEKDA PKELLQMLEK     60
Q                                                                    61

SEQ ID NO: 9            moltype = AA  length = 61
FEATURE                 Location/Qualifiers
REGION                  1..61
                        note = Synthetic Polypeptide
source                  1..61
                        mol_type = protein
                        organism = synthetic construct
SEQUENCE: 9
ATVKFTYRGE EKQVDISKIK WVNRWGQHLA FKYDVGGGAA GYGWMSEKDA PKELLQMLEK     60
R                                                                    61

SEQ ID NO: 10           moltype = AA  length = 61
FEATURE                 Location/Qualifiers
REGION                  1..61
                        note = Synthetic Polypeptide
source                  1..61
                        mol_type = protein
                        organism = synthetic construct
SEQUENCE: 10
ATVKFTYQGE EKQVDISKIK WVIRLGRTIM FKYDEGGGAN GYGKVSEKDA PKELLQMLEK     60
Q                                                                    61
```

```
SEQ ID NO: 11            moltype = AA   length = 61
FEATURE                  Location/Qualifiers
REGION                   1..61
                         note = Synthetic Polypeptide
source                   1..61
                         mol_type = protein
                         organism = synthetic construct
SEQUENCE: 11
ATVKFTYQGE EKQVDISKIK WVVRLGQVIM FKYDEGGGAN GYGKVSEKDA PKELLQMLEK   60
Q                                                                  61

SEQ ID NO: 12            moltype = AA   length = 61
FEATURE                  Location/Qualifiers
REGION                   1..61
                         note = Synthetic Polypeptide
source                   1..61
                         mol_type = protein
                         organism = synthetic construct
SEQUENCE: 12
ATVKFTYRGE EKQVDISKIK WVVRLGQVIM FKYGEGGGSN GYGRVSEKDA PKELRQMLEK   60
R                                                                  61

SEQ ID NO: 13            moltype = AA   length = 60
FEATURE                  Location/Qualifiers
REGION                   1..60
                         note = Synthetic Polypeptide
source                   1..60
                         mol_type = protein
                         organism = synthetic construct
SEQUENCE: 13
ATVKFTYRGE EKQVDISKIK WVVRLGQVIM FKYDEGGGAS GYGRVSEKDA PKELLQMLEK   60

SEQ ID NO: 14            moltype = AA   length = 73
FEATURE                  Location/Qualifiers
REGION                   1..73
                         note = Synthetic Polypeptide
source                   1..73
                         mol_type = protein
                         organism = synthetic construct
SEQUENCE: 14
ATVKFTYRGE EKQVGVSRVK SVHRIGQWIK FWYDEGSGAY GRGYVSEKDA PEELQMLEK    60
RGSEQKLISE EDL                                                     73

SEQ ID NO: 15            moltype = AA   length = 7
FEATURE                  Location/Qualifiers
REGION                   1..7
                         note = Synthetic Polypeptide
source                   1..7
                         mol_type = protein
                         organism = synthetic construct
SEQUENCE: 15
ATVKFTY                                                            7

SEQ ID NO: 16            moltype = AA   length = 18
FEATURE                  Location/Qualifiers
REGION                   1..18
                         note = Synthetic Polypeptide
source                   1..18
                         mol_type = protein
                         organism = synthetic construct
SEQUENCE: 16
GVSRVKSVHR IGQWIKFW                                                18

SEQ ID NO: 17            moltype = AA   length = 5
FEATURE                  Location/Qualifiers
REGION                   1..5
                         note = Synthetic Polypeptide
VARIANT                  3
                         note = X can be any naturally occurring amino acid
source                   1..5
                         mol_type = protein
                         organism = synthetic construct
SEQUENCE: 17
LPXTG                                                              5

SEQ ID NO: 18            moltype = AA   length = 5
FEATURE                  Location/Qualifiers
REGION                   1..5
```

```
                            note = Synthetic Polypeptide
VARIANT                     3
                            note = X can be any naturally occurring amino acid
source                      1..5
                            mol_type = protein
                            organism = synthetic construct
SEQUENCE: 18
LRXTG                                                                           5

SEQ ID NO: 19               moltype = AA  length = 5
FEATURE                     Location/Qualifiers
REGION                      1..5
                            note = Synthetic Polypeptide
source                      1..5
                            mol_type = protein
                            organism = synthetic construct
SEQUENCE: 19
GGGGS                                                                           5

SEQ ID NO: 20               moltype = AA  length = 10
FEATURE                     Location/Qualifiers
REGION                      1..10
                            note = Synthetic Polypeptide
source                      1..10
                            mol_type = protein
                            organism = synthetic construct
SEQUENCE: 20
GGGGSGGGGS                                                                     10

SEQ ID NO: 21               moltype = AA  length = 15
FEATURE                     Location/Qualifiers
REGION                      1..15
                            note = Synthetic Polypeptide
source                      1..15
                            mol_type = protein
                            organism = synthetic construct
SEQUENCE: 21
GGGGSGGGGS GGGGS                                                               15

SEQ ID NO: 22               moltype = AA  length = 20
FEATURE                     Location/Qualifiers
REGION                      1..20
                            note = Synthetic Polypeptide
source                      1..20
                            mol_type = protein
                            organism = synthetic construct
SEQUENCE: 22
GGGGSGGGGS GGGGSGGGGS                                                          20

SEQ ID NO: 23               moltype = AA  length = 25
FEATURE                     Location/Qualifiers
REGION                      1..25
                            note = Synthetic Polypeptide
source                      1..25
                            mol_type = protein
                            organism = synthetic construct
SEQUENCE: 23
GGGGSGGGGS GGGGSGGGGS GGGGS                                                    25

SEQ ID NO: 24               moltype = AA  length = 30
FEATURE                     Location/Qualifiers
REGION                      1..30
                            note = Synthetic Polypeptide
source                      1..30
                            mol_type = protein
                            organism = synthetic construct
SEQUENCE: 24
GGGGSGGGGS GGGGSGGGGS GGGGSGGGGS                                               30

SEQ ID NO: 25               moltype = AA  length = 72
FEATURE                     Location/Qualifiers
REGION                      1..72
                            note = Synthetic Polypeptide
source                      1..72
                            mol_type = protein
                            organism = synthetic construct
SEQUENCE: 25
ATVKFTYQGE EKQVDISKIK HVRRWGRWIW FIYEEGGGAK GRGGVSEKDA PKELLQMLEK              60
QGSEQKLISE ED                                                                  72
```

```
SEQ ID NO: 26          moltype = AA  length = 72
FEATURE                Location/Qualifiers
REGION                 1..72
                       note = Synthetic Polypeptide
source                 1..72
                       mol_type = protein
                       organism = synthetic construct
SEQUENCE: 26
ATGKFTYQGE KKQGDISKIK HGRRWGRGIW FIYEEGGGAK GRGGVSEKDA PKELLQMLEK    60
QGSEQKLISE ED                                                       72

SEQ ID NO: 27          moltype = AA  length = 72
FEATURE                Location/Qualifiers
REGION                 1..72
                       note = Synthetic Polypeptide
source                 1..72
                       mol_type = protein
                       organism = synthetic construct
SEQUENCE: 27
ITVKFTYQGE EKQVDISKIE HVRRWGQWIW FTYDEGGGAK GRGGVSEKGA PKELLQMLGK    60
RGSEQKLISE ED                                                       72

SEQ ID NO: 28          moltype = AA  length = 72
FEATURE                Location/Qualifiers
REGION                 1..72
                       note = Synthetic Polypeptide
source                 1..72
                       mol_type = protein
                       organism = synthetic construct
SEQUENCE: 28
ATVKFTYQGE EKQVDISKIK HVRRWGQWIW FIYDKGGGAK GRGGVSEKDA PKELLQMLEK    60
QGSEQKLISE ED                                                       72

SEQ ID NO: 29          moltype = AA  length = 69
FEATURE                Location/Qualifiers
REGION                 1..69
                       note = Synthetic Polypeptide
source                 1..69
                       mol_type = protein
                       organism = synthetic construct
SEQUENCE: 29
ATVKFTYQGE EKQVDISKIK HVRRWGQWIW FIYDEGGGAK GKGSVSEKDA PKELLQMLEK    60
AGIRTKAYF                                                           69

SEQ ID NO: 30          moltype = AA  length = 72
FEATURE                Location/Qualifiers
REGION                 1..72
                       note = Synthetic Polypeptide
source                 1..72
                       mol_type = protein
                       organism = synthetic construct
SEQUENCE: 30
ATVEFTYQGE EKQVDISKIK HVRRWGQWIW FIYDEGGGAK GRGGVSERDA PKELLQLLEK    60
RGSEQKLISE ED                                                       72

SEQ ID NO: 31          moltype = AA  length = 69
FEATURE                Location/Qualifiers
REGION                 1..69
                       note = Synthetic Polypeptide
source                 1..69
                       mol_type = protein
                       organism = synthetic construct
SEQUENCE: 31
ATVKFTYQGE EKQVDISKIK YVRRWGQAII FRYDEGGGAE GKGSVSEKGA PKELLQMLEK    60
ARIRTKAYF                                                           69

SEQ ID NO: 32          moltype = AA  length = 72
FEATURE                Location/Qualifiers
REGION                 1..72
                       note = Synthetic Polypeptide
source                 1..72
                       mol_type = protein
                       organism = synthetic construct
SEQUENCE: 32
ATVKFTYRGE EKQVGISRIK SVHRIGQWIK FWYDEGSGAY GRGYVSEKDA PKELLQMLEK    60
RGSEQKLISE ED                                                       72

SEQ ID NO: 33          moltype = AA  length = 72
```

```
FEATURE              Location/Qualifiers
REGION               1..72
                     note = Synthetic Polypeptide
source               1..72
                     mol_type = protein
                     organism = synthetic construct
SEQUENCE: 33
AIVKFTYQGE EKQVDISKIK YVRRWGQYIW FGYDEGGGAH GRGRVSGKDA PKELLQMLEK    60
QGSEQKLISE ED                                                       72

SEQ ID NO: 34        moltype = AA  length = 69
FEATURE              Location/Qualifiers
REGION               1..69
                     note = Synthetic Polypeptide
source               1..69
                     mol_type = protein
                     organism = synthetic construct
SEQUENCE: 34
ATVKFTYRGE EKQVDISKIK SVSRWGQAII FRYDGGGGAR GKGSVSEKDA PKELLQMLEE    60
ARIRTKAYF                                                           69

SEQ ID NO: 35        moltype = AA  length = 68
FEATURE              Location/Qualifiers
REGION               1..68
                     note = Synthetic Polypeptide
source               1..68
                     mol_type = protein
                     organism = synthetic construct
SEQUENCE: 35
ATVKFTYRGE EKQVGISRIK SVHRIGQWIK FWYDEGSGAY GRGYVSEKDA PKELLQMLEK    60
RGSEQKLF                                                            68

SEQ ID NO: 36        moltype = AA  length = 60
FEATURE              Location/Qualifiers
REGION               1..60
                     note = Synthetic Polypeptide
source               1..60
                     mol_type = protein
                     organism = synthetic construct
SEQUENCE: 36
ATVKFTYRGK EKQVGISRIK SVHRIGQWIR FWYDEGSGAY GRGYVSEKDA PKELLQMLEK    60

SEQ ID NO: 37        moltype = AA  length = 72
FEATURE              Location/Qualifiers
REGION               1..72
                     note = Synthetic Polypeptide
source               1..72
                     mol_type = protein
                     organism = synthetic construct
SEQUENCE: 37
ATVKFTYRGE EKQVGISRIK SVHRIGQWIK FWYDEGSGAY GRGYVSGKDA PKELLQMLEK    60
RGSEQKLISE ED                                                       72

SEQ ID NO: 38        moltype = AA  length = 72
FEATURE              Location/Qualifiers
REGION               1..72
                     note = Synthetic Polypeptide
source               1..72
                     mol_type = protein
                     organism = synthetic construct
SEQUENCE: 38
ATVKFTYRGK EKQVGISRIK SVHRIGQWIK FWYDEGSGAY GRGYVSGKDA PKELLQMLEK    60
RGSEQKLISE ED                                                       72

SEQ ID NO: 39        moltype = AA  length = 72
FEATURE              Location/Qualifiers
REGION               1..72
                     note = Synthetic Polypeptide
source               1..72
                     mol_type = protein
                     organism = synthetic construct
SEQUENCE: 39
ATVKFTYRGE EKQVGINRIK SVHRIGQWIK FWYDEGSGAY GRGYVSGKDA PKELLRMLEK    60
RGSEQKLISE ED                                                       72

SEQ ID NO: 40        moltype = AA  length = 72
FEATURE              Location/Qualifiers
REGION               1..72
                     note = Synthetic Polypeptide
```

```
source                          1..72
                                mol_type = protein
                                organism = synthetic construct
SEQUENCE: 40
ATVKFTYRGE EKQVGISRIK SVHRIGRWIK FWYDEGSGAY GRGYVSGKDA PKELLQMLEK    60
RGSEQKLISE ED                                                       72

SEQ ID NO: 41                   moltype = AA  length = 72
FEATURE                         Location/Qualifiers
REGION                          1..72
                                note = Synthetic Polypeptide
source                          1..72
                                mol_type = protein
                                organism = synthetic construct
SEQUENCE: 41
ATVKFTYRGE EKQVGISRIK SVRRIGQWIK FWYDEGSGAY GRGYVSGKDA PKELLQMLEK    60
RGSEQKLISE ED                                                       72

SEQ ID NO: 42                   moltype = AA  length = 72
FEATURE                         Location/Qualifiers
REGION                          1..72
                                note = Synthetic Polypeptide
source                          1..72
                                mol_type = protein
                                organism = synthetic construct
SEQUENCE: 42
ATVKFTYRGE EKRVGISRIK SVRRIGQWIK FWYDEGSGAY GRGYVSEKDA PKELLQMLGK    60
RGSEQKLISE ED                                                       72

SEQ ID NO: 43                   moltype = AA  length = 72
FEATURE                         Location/Qualifiers
REGION                          1..72
                                note = Synthetic Polypeptide
source                          1..72
                                mol_type = protein
                                organism = synthetic construct
SEQUENCE: 43
ATVKFTYRGE EKQVGISRIK SVRRIGQWIK FWYDEGSGAY GRGYVSEKDA PKELLQMLGK    60
RGSEQKLISE ED                                                       72

SEQ ID NO: 44                   moltype = AA  length = 72
FEATURE                         Location/Qualifiers
REGION                          1..72
                                note = Synthetic Polypeptide
source                          1..72
                                mol_type = protein
                                organism = synthetic construct
SEQUENCE: 44
ATVRFTYRGE EKQVGISRIK SVRRIGQWIK FWYDEGSGAY GRGYVSEKDA PKELLQMLGK    60
RGSEQKLISE ED                                                       72

SEQ ID NO: 45                   moltype = AA  length = 72
FEATURE                         Location/Qualifiers
REGION                          1..72
                                note = Synthetic Polypeptide
source                          1..72
                                mol_type = protein
                                organism = synthetic construct
SEQUENCE: 45
ATVKFTYRGE EKQVGISRIK SVHRIGQWIK FWYDEGSGAY GRGYVSEKGA PKELLQMLGK    60
RGSEQKLISE ED                                                       72

SEQ ID NO: 46                   moltype = AA  length = 72
FEATURE                         Location/Qualifiers
REGION                          1..72
                                note = Synthetic Polypeptide
source                          1..72
                                mol_type = protein
                                organism = synthetic construct
SEQUENCE: 46
ATVKFTYRGE EKQVGISRIR SVHRIGQWIK FWYDEGSGAC GRGYVSEKGA PKELLQMLGK    60
RGSEQKLISE ED                                                       72

SEQ ID NO: 47                   moltype = AA  length = 72
FEATURE                         Location/Qualifiers
REGION                          1..72
                                note = Synthetic Polypeptide
source                          1..72
                                mol_type = protein
```

```
                            organism = synthetic construct
SEQUENCE: 47
ATVKFTYRGE EKQVGISRIK SVHRIGQWIK FWYDEGSGAY GRGYVSEKDA PKELLQMLGK    60
RGSEQKLISE ED                                                       72

SEQ ID NO: 48           moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 48
ATVRFTYRGE EKQVGISRIK SVHRIGQWIK FWYDEGSGTY GRGYVSEKDA PRELLQMLGK    60
RGSEQKLISE ED                                                       72

SEQ ID NO: 49           moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 49
ATVKFTYRGE EKQVGISRIK SVRRIGQWIK FWYDEGSGAY GRGYVSEKDA PKELLQMLEK    60
RGSEQKLISE ED                                                       72

SEQ ID NO: 50           moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 50
ATVKFTYRGG EKQVGISRIK SVRRIGQWIK FWYDEGSGAY GRGYVSEKDA PKELLQMLEK    60
RGSEQKLISE ED                                                       72

SEQ ID NO: 51           moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 51
ATVKFTYRGK EKRVGVSRIK SVRRIGQWIK FWYDEGSGAY GRGYVSEKDA PKELLQMLEK    60
RGSEQKLISE ED                                                       72

SEQ ID NO: 52           moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 52
ATVKFTYRGE EKRVGISRIK SVRRIGQWIK FWYDEGSGAY GRGYVSEKDA PKELLQMLEK    60
RGSEQKLISE ED                                                       72

SEQ ID NO: 53           moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 53
ATVKFTYRGE EKQVGISRIK SVRRIGQWVK FWYDEGSGAY GRGYVSEKDA PKELLQMLEK    60
RGSEQKLISE ED                                                       72

SEQ ID NO: 54           moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 54
```

```
ATVKFTYRGE EKQVGISRIK SVRRIGQWVK FWYGEGSGAY GRGYVSEKDA PKELLQMLEK    60
RGSEQKLISE ED                                                       72

SEQ ID NO: 55           moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 55
ATVKFTYRGE EKQVGISRIR SVRRIGQWIK FWYDEGSGAY GRGYVSEKDA PKELLQMLEK    60
RGSEQKLISE ED                                                       72

SEQ ID NO: 56           moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 56
ATVKFTYRGE EKQVGISRIK SVRRIGQWIK FWYDEGRGAY GRGYVSEKDA PKELLQMLEK    60
RGSEQKLISE ED                                                       72

SEQ ID NO: 57           moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 57
ATVKFTYRGE EKQVGISRIK SVRRIGQWIK FWYDEGSGAY GRGYVSEKDA PEELLQMLEK    60
RGSEQKLISE ED                                                       72

SEQ ID NO: 58           moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 58
ATVKFTYRGE EKQVGISRIK SVHRIGQWIK FWYDEGSGAY GRGYVSKKDA PKELLQMLEK    60
RGSEQKLISE ED                                                       72

SEQ ID NO: 59           moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 59
ATVKFTYRGE EKQVGVSRIK SVHRIGRWIK FWYDEGSGAY GRGYVSEKDA PKELLQMLEK    60
RGSEQKLISE ED                                                       72

SEQ ID NO: 60           moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 60
ATVKFTYRGE EKQVGISRIK SVHRIGRWIK FWYDEGSGAY GRGYVSEKDA PKELLQMLEK    60
RGSEQKLISE ED                                                       72

SEQ ID NO: 61           moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 61
ATVKFTYRGE EKQVGISRIK SVHRVGRWIK FWYDEGSGAY GRGYVSEKDA PKELLQMLEK    60
RGSEQKLISE ED                                                       72
```

```
SEQ ID NO: 62            moltype = AA  length = 72
FEATURE                  Location/Qualifiers
REGION                   1..72
                         note = Synthetic Polypeptide
source                   1..72
                         mol_type = protein
                         organism = synthetic construct
SEQUENCE: 62
ATVKFTYRGE EKQVGIGRIK SVHRIGRWIK FWYDEGSGAY GRGYVSEKDA PKELLQMLEK    60
RGSEQKLISE ED                                                       72

SEQ ID NO: 63            moltype = AA  length = 72
FEATURE                  Location/Qualifiers
REGION                   1..72
                         note = Synthetic Polypeptide
source                   1..72
                         mol_type = protein
                         organism = synthetic construct
SEQUENCE: 63
ATVKFTYRGE EKQVGISRIK SVHRIGRWIK FWYDEGSGAY GRGYVNEKDA PKELLQMLEK    60
RGSEQKLISE ED                                                       72

SEQ ID NO: 64            moltype = AA  length = 72
FEATURE                  Location/Qualifiers
REGION                   1..72
                         note = Synthetic Polypeptide
source                   1..72
                         mol_type = protein
                         organism = synthetic construct
SEQUENCE: 64
ATVKFTYRGE EKQVGISRIK FVHRIGRWIK FWYDEGSGAY GRGYVSEKDA PKELLQMLEK    60
RGSEQKLISE ED                                                       72

SEQ ID NO: 65            moltype = AA  length = 72
FEATURE                  Location/Qualifiers
REGION                   1..72
                         note = Synthetic Polypeptide
source                   1..72
                         mol_type = protein
                         organism = synthetic construct
SEQUENCE: 65
ATVKFTYRGE EKQVGISRIK SVHRIGQWIK FWYDEGSGAY GRGYVSEKNA PKELLQMLEK    60
RGSEQKLISE ED                                                       72

SEQ ID NO: 66            moltype = AA  length = 72
FEATURE                  Location/Qualifiers
REGION                   1..72
                         note = Synthetic Polypeptide
source                   1..72
                         mol_type = protein
                         organism = synthetic construct
SEQUENCE: 66
ATVKFTYRGE EKQVGISRIK SVHRIGQWIK FWYDEGSGAY GRGYVSEKGA PKELLQMLEK    60
RGSEQKLISE ED                                                       72

SEQ ID NO: 67            moltype = AA  length = 72
FEATURE                  Location/Qualifiers
REGION                   1..72
                         note = Synthetic Polypeptide
source                   1..72
                         mol_type = protein
                         organism = synthetic construct
SEQUENCE: 67
ATVKFTYRGE GKQVGISRIK SVHRIGQWIK FWYDEGSGAY GRGYVSEKDA PKELLQMLEK    60
RGSEQKLISE ED                                                       72

SEQ ID NO: 68            moltype = AA  length = 72
FEATURE                  Location/Qualifiers
REGION                   1..72
                         note = Synthetic Polypeptide
source                   1..72
                         mol_type = protein
                         organism = synthetic construct
SEQUENCE: 68
ATVKFTYRGE GKQVGISRIK SVHRIGQWIK FWYDEGSGAY GRGYVSEKDA PKELLQMLKK    60
RGSEQKLISE ED                                                       72

SEQ ID NO: 69            moltype = AA  length = 72
```

```
FEATURE              Location/Qualifiers
REGION               1..72
                     note = Synthetic Polypeptide
source               1..72
                     mol_type = protein
                     organism = synthetic construct
SEQUENCE: 69
ATVKFTYRGE RKQVGISRIK SVHRIGQWIK FWYDEGSGAY GRGYVSEKDA PKELLQMLEK    60
RGSEQKLISE ED                                                        72

SEQ ID NO: 70        moltype = AA  length = 72
FEATURE              Location/Qualifiers
REGION               1..72
                     note = Synthetic Polypeptide
source               1..72
                     mol_type = protein
                     organism = synthetic construct
SEQUENCE: 70
ATVKFTYRGE EKQVGISRIK SVHRVGQWIK FWYDEGSGAY GRGYVSEKDA PKELLQMLEK    60
RGSEQKLISE ED                                                        72

SEQ ID NO: 71        moltype = AA  length = 72
FEATURE              Location/Qualifiers
REGION               1..72
                     note = Synthetic Polypeptide
source               1..72
                     mol_type = protein
                     organism = synthetic construct
SEQUENCE: 71
ATVKFTYRGE ERQVGISRIK SVHRIGQWIK FWYDEGSGAY GRGYVSEKDA PKELLQMLEK    60
RGSEQKLISE ED                                                        72

SEQ ID NO: 72        moltype = AA  length = 72
FEATURE              Location/Qualifiers
REGION               1..72
                     note = Synthetic Polypeptide
source               1..72
                     mol_type = protein
                     organism = synthetic construct
SEQUENCE: 72
ATVKFTYRGE EKQVGISRIK SVHRIGQWIK FWYDEGSGAY GRGYVGEKDA PKELLQMLEK    60
RGSEQKLISE ED                                                        72

SEQ ID NO: 73        moltype = AA  length = 72
FEATURE              Location/Qualifiers
REGION               1..72
                     note = Synthetic Polypeptide
source               1..72
                     mol_type = protein
                     organism = synthetic construct
SEQUENCE: 73
ATVKFTYRGE EKRVGISRIK SVHRIGQWIK FWYDEGSGAY GRGYVSEKDA PKELLQMLEK    60
RGSEQKLISE ED                                                        72

SEQ ID NO: 74        moltype = AA  length = 72
FEATURE              Location/Qualifiers
REGION               1..72
                     note = Synthetic Polypeptide
source               1..72
                     mol_type = protein
                     organism = synthetic construct
SEQUENCE: 74
ATVKFTYRGE EKQVGISRIK SVHRIGQWIK FWYDEGSGAY GRGYVSEKDA PKELLRMLEK    60
RGSEQKLISE ED                                                        72

SEQ ID NO: 75        moltype = AA  length = 72
FEATURE              Location/Qualifiers
REGION               1..72
                     note = Synthetic Polypeptide
source               1..72
                     mol_type = protein
                     organism = synthetic construct
SEQUENCE: 75
ATVKFTYRGE EKQVGVSRIK SVHRIGQWIK FWYDGGSGAY GRGYVSEKDA PKELLQMLEK    60
RGSEQKLISE ED                                                        72

SEQ ID NO: 76        moltype = AA  length = 72
FEATURE              Location/Qualifiers
REGION               1..72
```

```
                        note = Synthetic Polypeptide
source                  1..72
                        mol_type = protein
                        organism = synthetic construct
SEQUENCE: 76
ATVKFTYRGE EKQVGISRIK SVHRIGQWIK FWYDGGSGAY GRGYVSEKDA PKELLQMLEK   60
RGSEQKLISE ED                                                      72

SEQ ID NO: 77           moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 77
ATVKFTYRGE EKQVGVSRVK SVHRIGQWIK FWYDEGSGAY GRGYVSEKDA PEELLQMLEK   60
RGSEQKLISE ED                                                      72

SEQ ID NO: 78           moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 78
ATVKFTYRGE EKQVGISRIK SVHRIGQWIK FWYDEGSGAH GRGYVSEKDA PKELLQMLEK   60
RGSEQKLISE ED                                                      72

SEQ ID NO: 79           moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 79
ATVKFTYRGE EKQVGISRIK SVHRIGQWIK FRYDEGSGAY GRGYVSEKDA PKELLQMLEK   60
RGSEQKLISE ED                                                      72

SEQ ID NO: 80           moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 80
VTVEFTYRGE EKQVDISKIK HVRRWGRWIW FIYEEGGGAK GRGGVSEKDA PKELLQMLEK   60
RGSEQKLISE ED                                                      72

SEQ ID NO: 81           moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 81
ATVKFTYQGE EKQVDISKIK HVRRWGRWIW FIYEEGGGAK GRGGVSEKDA PKELLQMLEK   60
RGSEQKLISE ED                                                      72

SEQ ID NO: 82           moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 82
ATVRFTYQGE EKQVDISKIK HVRRWGRWIW FIYEEGGGAK GRGGVSEKDA PKELLQMLEK   60
RGSEQKLISE ED                                                      72

SEQ ID NO: 83           moltype = AA  length = 72
FEATURE                 Location/Qualifiers
REGION                  1..72
                        note = Synthetic Polypeptide
source                  1..72
```

```
                        mol_type = protein
                        organism = synthetic construct
SEQUENCE: 83
ATVKFTYQGE EKQVDISKIK HVRRWGRWIW FIYEEGGGGK GRGGVSEKDA PKELLQMLEK    60
RGSEQKLISE ED                                                        72

SEQ ID NO: 84           moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 84
ATVKFTHQGE EKQVDISKIK HVRRWGRWIW FIYEEGGGAK GRGGVSEKDA PKELLQMLEK    60
RGSEQKLISE ED                                                        72

SEQ ID NO: 85           moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 85
AIVKFTYQGE EKQVDISKIK HVRRWGRWIW FIYEEGGGAK GRGGVSEKDA PKELLQMLEK    60
RGSEQKLISE ED                                                        72

SEQ ID NO: 86           moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 86
AAVKFTYQGE EKQVDISKIK HVRRWGRWIW FIYEEGGGAK GRGGVSEKDA PKELLQMLEK    60
QGSEQKLISE ED                                                        72

SEQ ID NO: 87           moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 87
ATVKFTYQGE EKQVDISKIK HVRRWGRWIW FIYEAGGGAK GRGGVSEKDA PKELLQMLEK    60
QGSEQKLISE ED                                                        72

SEQ ID NO: 88           moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 88
ATVKFTYQGE EKQVDISKIK HVRRWGRWIW FIYEGGGGAK GRGGVSEKDA PKELLQMLER    60
RGSEQKLISE ED                                                        72

SEQ ID NO: 89           moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 89
ATVKFTYQGE EKQVDISKIK HVRRWGRWIW FIYEGGGGAK GRGGVSEKDA PKELLQMLEK    60
QGSEQKLISE ED                                                        72

SEQ ID NO: 90           moltype = AA  length = 69
FEATURE                 Location/Qualifiers
REGION                  1..69
                        note = Synthetic Polypeptide
source                  1..69
                        mol_type = protein
                        organism = synthetic construct
```

```
SEQUENCE: 90
ATVKFTYRGE EKQVDISKIK HVRRWGQWIW FIYDEGGGAK GKGSVSEKDA PKELLQMLEK    60
AGIRTKAYF                                                            69

SEQ ID NO: 91           moltype = AA   length = 69
FEATURE                 Location/Qualifiers
REGION                  1..69
                        note = Synthetic Polypeptide
source                  1..69
                        mol_type = protein
                        organism = synthetic construct
SEQUENCE: 91
ATVKFTYQGE EKQVDVSKIK HVRRWGQWIW FIYDEGGGAK GKGSVSEKDA PKELLQMLGK    60
AGIRTKAYF                                                            69

SEQ ID NO: 92           moltype = AA   length = 69
FEATURE                 Location/Qualifiers
REGION                  1..69
                        note = Synthetic Polypeptide
source                  1..69
                        mol_type = protein
                        organism = synthetic construct
SEQUENCE: 92
ATVKFTYQGE EKQVDISKIK HVRRWGRWIW FIYDEGGGAK GKGSVSEKDA PKELLQMLEK    60
AGIRTKAYF                                                            69

SEQ ID NO: 93           moltype = AA   length = 69
FEATURE                 Location/Qualifiers
REGION                  1..69
                        note = Synthetic Polypeptide
source                  1..69
                        mol_type = protein
                        organism = synthetic construct
SEQUENCE: 93
ATVKFTYQGE EKQVDISKIK HVRRWGRWIW FIYEEGGGAK GKGSVSEKDA PKELLQMLEK    60
AGIRTKAYF                                                            69

SEQ ID NO: 94           moltype = AA   length = 69
FEATURE                 Location/Qualifiers
REGION                  1..69
                        note = Synthetic Polypeptide
source                  1..69
                        mol_type = protein
                        organism = synthetic construct
SEQUENCE: 94
ATVKFTYQGE EKQVDISKIK HVRRWGQRIW FIYGEGGGAK GRGSVSEKDA PKELLQMLEK    60
AGIRTKAYF                                                            69

SEQ ID NO: 95           moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 95
ATVKFTYQGE EKQVDISKIK HVRRWGRWIW FIYEEGGAKG RGGVSEKDAP KELLQMLEKQ    60
GSEQKLISEE DL                                                        72

SEQ ID NO: 96           moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 96
ATVKFTYQGE EKQVDISKIK HVRRWGRWIW FTYEEGGGAK GRGGVSEKDA PKELLQMLEK    60
QGSEQKLILK RT                                                        72

SEQ ID NO: 97           moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 97
ATVKFTYQGE EKQVDISKIK HVRRWGRWIW FTYEEGGGAK GRGGVSEKDA PKELLQMLEK    60
```

```
PGSEQKLISE ED                                                            72

SEQ ID NO: 98           moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 98
ATVKFTYQGE EKQVDISKIK HVRRWGRWIW FTYEEGGGAR GRGGVSEKDA PKELLQMLEK         60
QGSEQKLISE ED                                                            72

SEQ ID NO: 99           moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 99
ATVKFTYQGE EKQVDVSKIK HVRRWGRWIW FTYEEGGGAK GRGGVSEKDA PKELLQMLEK         60
QGSEQKLISE ED                                                            72

SEQ ID NO: 100          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 100
ATVKFTYQGE EKQVDISKIK HVRRWGRWIW FTYEEGGGAK GRGGVSEKDA PRELLQMLEK         60
RGSEQKLISE ED                                                            72

SEQ ID NO: 101          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 101
ATVKFTYRGE EKQVDISEIK HVRRWGRWIW FTYEEGGGAR GRGGVSEKDA PKELLQMLEK         60
RGSEQKLISE ED                                                            72

SEQ ID NO: 102          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 102
ATVKFTYQGE EKQVDISKIR HVRRWGRRIW FTYEEGGGAK GRGGVGEKDA PKELLQMLEK         60
QGSEQKLISE ED                                                            72

SEQ ID NO: 103          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 103
ATVKFTYQGE EKQVDISKIK HVRRWGRRIW FIYEEGGGAK GRGGVSEKDA PKELLQMLEK         60
QGSEQKLISE KD                                                            72

SEQ ID NO: 104          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 104
ATVKFTYQGE EKQVDISKIK HVRRWGRRIW FIYEEGGGAK GRGGVSEKDA PKELLQMLEK         60
QGSEQKLISE ED                                                            72
```

```
SEQ ID NO: 105          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 105
ATVKFTYQGE EKQVDISKIK HVRRWGRWIW FIYEEGGGAK GRGGVGEKDA PKELLQMLEK     60
QGSEQKLISE ED                                                        72

SEQ ID NO: 106          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 106
ATVKFTYQGE GKQVDISKIK HVRRWGRWIW FIYEEGGGAK GRGGVSEKDA PKELLQMLEK     60
QGSEQKLISE ED                                                        72

SEQ ID NO: 107          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 107
ATVKFTYQGE EKQVDISKIK RVRRWGRWIW FIYEEGGGAK GRGGVSEKDA PKELLQMLEK     60
QGSEQKLISE ED                                                        72

SEQ ID NO: 108          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 108
ITVKFTYQGE EKQVDISKIE HVRRWGRWIW FTYDEGGGAK GRGGVSEKGA PKELLQMLGK     60
RGSEQKLISE ED                                                        72

SEQ ID NO: 109          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 109
ITVKFTYRGE EKQVDISKIE HVRRWGQWIW FTYDEGGGAK GRGGVSEKGA PRELLQMLGK     60
RGSEQKLISE ED                                                        72

SEQ ID NO: 110          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 110
ATVKFTYQGE EKQVDISKIK HVRRWGRWIW FTYDEGGGAK GRGGVSEKGA PKELLQMLGK     60
RGSEQKLISE ED                                                        72

SEQ ID NO: 111          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 111
ATVKFTYQGE EKQVDISKIK HVRRWGRWIW FTYEEGGGAK GRGGVSEKDA PKELLQMLGK     60
RGSEQKLISE ED                                                        72

SEQ ID NO: 112          moltype = AA  length = 72
FEATURE                 Location/Qualifiers
```

```
REGION                  1..72
                        note = Synthetic Polypeptide
source                  1..72
                        mol_type = protein
                        organism = synthetic construct
SEQUENCE: 112
ATVKFTYQGE EKRVDISKIK HVRRWGRWIW FIYEEGGGAK GRGGVSEKDA PKELLQMLGK   60
RGSEQKLISE ED                                                      72

SEQ ID NO: 113          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 113
ATVKFTYQGE EKQVDISKIK HVRRWGRWIW FIYEEGGGAK GRGGVSEKDA PKELLQMLGK   60
QGSEQKLISE ED                                                      72

SEQ ID NO: 114          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 114
ATVKFTYRGE EKQVDISKIK HVRRWGRWIW FIYEEGGGAK GRGGVSEKDA PKELLQMLGK   60
QRSEQKLISE ED                                                      72

SEQ ID NO: 115          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 115
ATVKFTYHGE EKQVDISKIK HVRRWGRWIW FIYEEGGGAK GRGGVSEKDA PKELLQMLEK   60
QGSEQKLISE ED                                                      72

SEQ ID NO: 116          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 116
ATVKFTYRGE EKQVDISKIK HVRRWGQWIW FIYDKGGGAK GRGGVSEKDA PKELLQMLEK   60
QGSEQKLISE ED                                                      72

SEQ ID NO: 117          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 117
ATVKFTYRGE EKQVDISKIK HVRCWGQWIW FIYDKGGGAK GRGGVSEKGA PKELLQMLEK   60
QGSEQKLISE ED                                                      72

SEQ ID NO: 118          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 118
ATVKFTYRGE EKQVGISRIR SVHRIGQWIK FWYDEGSGAY GRGYVSEKDA PKELLQMLEK   60
RGSEQKLISE ED                                                      72

SEQ ID NO: 119          moltype = AA  length = 72
FEATURE                 Location/Qualifiers
REGION                  1..72
                        note = Synthetic Polypeptide
```

```
source                   1..72
                         mol_type = protein
                         organism = synthetic construct
SEQUENCE: 119
TTVKFTYRGE EKQVGISRIK SVHRIGQWIK FWYDKGSGAY GRGYVSEKDA PKELLQMLEK    60
RGSEQKLISE ED                                                       72

SEQ ID NO: 120           moltype = AA   length = 72
FEATURE                  Location/Qualifiers
REGION                   1..72
                         note = Synthetic Polypeptide
source                   1..72
                         mol_type = protein
                         organism = synthetic construct
SEQUENCE: 120
AIVKFTYRGE EKQVGISRIK SVHRIGQWIK FWYGEGSGAY GRGYVSEKDA PKELLQMLEK    60
RGSEQKLISE ED                                                       72

SEQ ID NO: 121           moltype = AA   length = 72
FEATURE                  Location/Qualifiers
REGION                   1..72
                         note = Synthetic Polypeptide
source                   1..72
                         mol_type = protein
                         organism = synthetic construct
SEQUENCE: 121
ATVKFTYRGG EKQVGISRIK SVHRIGQWIK FRYDEGSGAY GRGYVSEKDA PKELLQMLEK    60
RGSEQKLISE ED                                                       72

SEQ ID NO: 122           moltype = AA   length = 72
FEATURE                  Location/Qualifiers
REGION                   1..72
                         note = Synthetic Polypeptide
source                   1..72
                         mol_type = protein
                         organism = synthetic construct
SEQUENCE: 122
ATVKFTYRGK EKQVGISRIK SVHRIGQWIK FRYDEGSGAY GRGYVSEKDA PKELLQMLEK    60
RGSEQKLISE ED                                                       72

SEQ ID NO: 123           moltype = AA   length = 72
FEATURE                  Location/Qualifiers
REGION                   1..72
                         note = Synthetic Polypeptide
source                   1..72
                         mol_type = protein
                         organism = synthetic construct
SEQUENCE: 123
ATVKFTYRGE EKQVDISRIK HVRRWGRWIW FIYEEGGGAK GRGGVSEKDA PKELLQMLEK    60
QGSEQKLISE ED                                                       72

SEQ ID NO: 124           moltype = AA   length = 72
FEATURE                  Location/Qualifiers
REGION                   1..72
                         note = Synthetic Polypeptide
source                   1..72
                         mol_type = protein
                         organism = synthetic construct
SEQUENCE: 124
ATVKFTYRGE EKQVDISKIK HVRRWGRWIW FIYEEGGGAK GRGGVSEKDA PKELLQMLEK    60
QGSEQKLISE ED                                                       72

SEQ ID NO: 125           moltype = AA   length = 72
FEATURE                  Location/Qualifiers
REGION                   1..72
                         note = Synthetic Polypeptide
source                   1..72
                         mol_type = protein
                         organism = synthetic construct
SEQUENCE: 125
ATVKFTYRGE EKQVDISKIK HVRRWGRWVW FIYEEGGGAK GRGGVSEKDA PKELLQMLEK    60
QGSEQKLISE ED                                                       72

SEQ ID NO: 126           moltype = AA   length = 72
FEATURE                  Location/Qualifiers
REGION                   1..72
                         note = Synthetic Polypeptide
source                   1..72
                         mol_type = protein
```

```
                        organism = synthetic construct
SEQUENCE: 126
ATVKFTYRGE EKQVDISKVK HVRRWGRWIW FIYEEGGGAK GRGGVSEKDA PKELLQMLEK    60
QGSEQKLISE ED                                                       72

SEQ ID NO: 127          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 127
ATVKFTYRGE EKQVDISKIK HVRRWGRWIW FIYEEGGGAK GRGGVSEKDA PKELLRMLEK    60
QGSEQKLISE ED                                                       72

SEQ ID NO: 128          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 128
ATVKFTYRGE EKQVDISKIK HVRRWGRWIW FIYEEGGGAK GRGGVSGKDA PKELLQMLEK    60
QGSEQKLISE ED                                                       72

SEQ ID NO: 129          moltype = AA   length = 68
FEATURE                 Location/Qualifiers
REGION                  1..68
                        note = Synthetic Polypeptide
source                  1..68
                        mol_type = protein
                        organism = synthetic construct
SEQUENCE: 129
ATVKFTYRGE EKQVGISRIK SVHRIGQWIK FWYDEGSGAY GRGYVSEKDA PKELLQMLEK    60
RGSEQKLF                                                            68

SEQ ID NO: 130          moltype = AA   length = 60
FEATURE                 Location/Qualifiers
REGION                  1..60
                        note = Synthetic Polypeptide
source                  1..60
                        mol_type = protein
                        organism = synthetic construct
SEQUENCE: 130
ATVKFTYRGK EKQVGISRIK SVHRIGQWIR FWYDEGSGAY GRGYVSEKDA PKELLQMLEK    60

SEQ ID NO: 131          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 131
ATVKFTYRGE EKQVGISRIK SVHRIGQWIK FWYDEGSGAY GRGYVSGKDA PKELLQMLEK    60
RGSEQKLISE ED                                                       72

SEQ ID NO: 132          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 132
ATVKFTYRGK EKQVGISRIK SVHRIGQWIK FWYDEGSGAY GRGYVSGKDA PKELLQMLEK    60
RGSEQKLISE ED                                                       72

SEQ ID NO: 133          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 133
ATVKFTYRGE EKQVGINRIK SVHRIGQWIK FWYDEGSGAY GRGYVSGKDA PKELLRMLEK    60
```

```
RGSEQKLISE ED                                                             72

SEQ ID NO: 134           moltype = AA  length = 72
FEATURE                  Location/Qualifiers
REGION                   1..72
                         note = Synthetic Polypeptide
source                   1..72
                         mol_type = protein
                         organism = synthetic construct
SEQUENCE: 134
ATVKFTYRGE EKQVGISRIK SVHRIGRWIK FWYDEGSGAY GRGYVSGKDA PKELLQMLEK         60
RGSEQKLISE ED                                                             72

SEQ ID NO: 135           moltype = AA  length = 72
FEATURE                  Location/Qualifiers
REGION                   1..72
                         note = Synthetic Polypeptide
source                   1..72
                         mol_type = protein
                         organism = synthetic construct
SEQUENCE: 135
ATVKFTYRGE EKQVGISRIK SVRRIGQWIK FWYDEGSGAY GRGYVSGKDA PKELLQMLEK         60
RGSEQKLISE ED                                                             72

SEQ ID NO: 136           moltype = AA  length = 72
FEATURE                  Location/Qualifiers
REGION                   1..72
                         note = Synthetic Polypeptide
source                   1..72
                         mol_type = protein
                         organism = synthetic construct
SEQUENCE: 136
ATVKFTYRGE EKRVGISRIK SVRRIGQWIK FWYDEGSGAY GRGYVSEKDA PKELLQMLGK         60
RGSEQKLISE ED                                                             72

SEQ ID NO: 137           moltype = AA  length = 72
FEATURE                  Location/Qualifiers
REGION                   1..72
                         note = Synthetic Polypeptide
source                   1..72
                         mol_type = protein
                         organism = synthetic construct
SEQUENCE: 137
ATVKFTYRGE EKQVGISRIK SVRRIGQWIK FWYDEGSGAY GRGYVSEKDA PKELLQMLGK         60
RGSEQKLISE ED                                                             72

SEQ ID NO: 138           moltype = AA  length = 72
FEATURE                  Location/Qualifiers
REGION                   1..72
                         note = Synthetic Polypeptide
source                   1..72
                         mol_type = protein
                         organism = synthetic construct
SEQUENCE: 138
ATVRFTYRGE EKQVGISRIK SVRRIGQWIK FWYDEGSGAY GRGYVSEKDA PKELLQMLGK         60
RGSEQKLISE ED                                                             72

SEQ ID NO: 139           moltype = AA  length = 72
FEATURE                  Location/Qualifiers
REGION                   1..72
                         note = Synthetic Polypeptide
source                   1..72
                         mol_type = protein
                         organism = synthetic construct
SEQUENCE: 139
ATVKFTYRGE EKQVGISRIK SVHRIGQWIK FWYDEGSGAY GRGYVSEKGA PKELLQMLGK         60
RGSEQKLISE ED                                                             72

SEQ ID NO: 140           moltype = AA  length = 72
FEATURE                  Location/Qualifiers
REGION                   1..72
                         note = Synthetic Polypeptide
source                   1..72
                         mol_type = protein
                         organism = synthetic construct
SEQUENCE: 140
ITVKFTYQGE EKQVDISKIE HVRRWGQWIW FTYDEGGGAK GRGGVSEKGA PKELLQMLGK         60
RGSEQKLISE ED                                                             72
```

-continued

```
SEQ ID NO: 141           moltype = AA  length = 72
FEATURE                  Location/Qualifiers
REGION                   1..72
                         note = Synthetic Polypeptide
source                   1..72
                         mol_type = protein
                         organism = synthetic construct
SEQUENCE: 141
ATVKFTYRGE EKQVGISRIR SVHRIGQWIK FWYDEGSGAC GRGYVSEKGA PKELLQMLGK    60
RGSEQKLISE ED                                                       72

SEQ ID NO: 142           moltype = AA  length = 72
FEATURE                  Location/Qualifiers
REGION                   1..72
                         note = Synthetic Polypeptide
source                   1..72
                         mol_type = protein
                         organism = synthetic construct
SEQUENCE: 142
ATVKFTYRGE EKQVGISRIK SVHRIGQWIK FWYDEGSGAY GRGYVSEKDA PKELLQMLGK    60
RGSEQKLISE ED                                                       72

SEQ ID NO: 143           moltype = AA  length = 72
FEATURE                  Location/Qualifiers
REGION                   1..72
                         note = Synthetic Polypeptide
source                   1..72
                         mol_type = protein
                         organism = synthetic construct
SEQUENCE: 143
ATVRFTYRGE EKQVGISRIK SVHRIGQWIK FWYDEGSGTY GRGYVSEKDA PRELLQMLGK    60
RGSEQKLISE ED                                                       72

SEQ ID NO: 144           moltype = AA  length = 72
FEATURE                  Location/Qualifiers
REGION                   1..72
                         note = Synthetic Polypeptide
source                   1..72
                         mol_type = protein
                         organism = synthetic construct
SEQUENCE: 144
ATVKFTYRGE EKQVGISRIK SVRRIGQWIK FWYDEGSGAY GRGYVSEKDA PKELLQMLEK    60
RGSEQKLISE ED                                                       72

SEQ ID NO: 145           moltype = AA  length = 72
FEATURE                  Location/Qualifiers
REGION                   1..72
                         note = Synthetic Polypeptide
source                   1..72
                         mol_type = protein
                         organism = synthetic construct
SEQUENCE: 145
ATVKFTYRGG EKQVGISRIK SVRRIGQWIK FWYDEGSGAY GRGYVSEKDA PKELLQMLEK    60
RGSEQKLISE ED                                                       72

SEQ ID NO: 146           moltype = AA  length = 72
FEATURE                  Location/Qualifiers
REGION                   1..72
                         note = Synthetic Polypeptide
source                   1..72
                         mol_type = protein
                         organism = synthetic construct
SEQUENCE: 146
ATVKFTYRGK EKRVGVSRIK SVRRIGQWIK FWYDEGSGAY GRGYVSEKDA PKELLQMLEK    60
RGSEQKLISE ED                                                       72

SEQ ID NO: 147           moltype = AA  length = 72
FEATURE                  Location/Qualifiers
REGION                   1..72
                         note = Synthetic Polypeptide
source                   1..72
                         mol_type = protein
                         organism = synthetic construct
SEQUENCE: 147
ATVKFTYRGE EKRVGISRIK SVRRIGQWIK FWYDEGSGAY GRGYVSEKDA PKELLQMLEK    60
RGSEQKLISE ED                                                       72

SEQ ID NO: 148           moltype = AA  length = 72
FEATURE                  Location/Qualifiers
```

```
REGION                  1..72
                        note = Synthetic Polypeptide
source                  1..72
                        mol_type = protein
                        organism = synthetic construct
SEQUENCE: 148
ATVKFTYRGE EKQVGISRIK SVRRIGQWVK FWYDEGSGAY GRGYVSEKDA PKELLQMLEK   60
RGSEQKLISE ED                                                       72

SEQ ID NO: 149          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 149
ATVKFTYRGE EKQVGISRIK SVRRIGQWVK FWYGEGSGAY GRGYVSEKDA PKELLQMLEK   60
RGSEQKLISE ED                                                       72

SEQ ID NO: 150          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 150
ATVKFTYRGE EKQVGISRIR SVRRIGQWIK FWYDEGSGAY GRGYVSEKDA PKELLQMLEK   60
RGSEQKLISE ED                                                       72

SEQ ID NO: 151          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 151
ATVKFTYRGE EKQVGISRIK SVRRIGQWIK FWYDEGRGAY GRGYVSEKDA PKELLQMLEK   60
RGSEQKLISE ED                                                       72

SEQ ID NO: 152          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 152
ATVKFTYRGE EKQVGISRIK SVRRIGQWIK FWYDEGSGAY GRGYVSEKDA PEELLQMLEK   60
RGSEQKLISE ED                                                       72

SEQ ID NO: 153          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 153
ATVKFTYRGE EKQVGISRIK SVHRIGQWIK FWYDEGSGAY GRGYVSKKDA PKELLQMLEK   60
RGSEQKLISE ED                                                       72

SEQ ID NO: 154          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 154
ATVKFTYRGE EKQVGVSRIK SVHRIGRWIK FWYDEGSGAY GRGYVSEKDA PKELLQMLEK   60
RGSEQKLISE ED                                                       72

SEQ ID NO: 155          moltype = AA  length = 72
FEATURE                 Location/Qualifiers
REGION                  1..72
                        note = Synthetic Polypeptide
```

```
source                  1..72
                        mol_type = protein
                        organism = synthetic construct
SEQUENCE: 155
ATVKFTYRGE EKQVGISRIK SVHRIGRWIK FWYDEGSGAY GRGYVSEKDA PKELLQMLEK    60
RGSEQKLISE ED                                                       72

SEQ ID NO: 156          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 156
ATVKFTYRGE EKQVGISRIK SVHRVGRWIK FWYDEGSGAY GRGYVSEKDA PKELLQMLEK    60
RGSEQKLISE ED                                                       72

SEQ ID NO: 157          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 157
ATVKFTYRGE EKQVGIGRIK SVHRIGRWIK FWYDEGSGAY GRGYVSEKDA PKELLQMLEK    60
RGSEQKLISE ED                                                       72

SEQ ID NO: 158          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 158
ATVKFTYRGE EKQVGISRIK SVHRIGRWIK FWYDEGSGAY GRGYVNEKDA PKELLQMLEK    60
RGSEQKLISE ED                                                       72

SEQ ID NO: 159          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 159
ATVKFTYRGE EKQVGISRIK FVHRIGRWIK FWYDEGSGAY GRGYVSEKDA PKELLQMLEK    60
RGSEQKLISE ED                                                       72

SEQ ID NO: 160          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 160
ATVKFTYRGE EKQVGISRIK SVHRIGQWIK FWYDEGSGAY GRGYVSEKNA PKELLQMLEK    60
RGSEQKLISE ED                                                       72

SEQ ID NO: 161          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 161
ATVKFTYRGE EKQVGISRIK SVHRIGQWIK FWYDEGSGAY GRGYVSEKGA PKELLQMLEK    60
RGSEQKLISE ED                                                       72

SEQ ID NO: 162          moltype = AA  length = 72
FEATURE                 Location/Qualifiers
REGION                  1..72
                        note = Synthetic Polypeptide
source                  1..72
                        mol_type = protein
```

```
                       organism = synthetic construct
SEQUENCE: 162
ATVKFTYRGE GKQVGISRIK SVHRIGQWIK FWYDEGSGAY GRGYVSEKDA PKELLQMLEK    60
RGSEQKLISE ED                                                       72

SEQ ID NO: 163         moltype = AA  length = 72
FEATURE                Location/Qualifiers
REGION                 1..72
                       note = Synthetic Polypeptide
source                 1..72
                       mol_type = protein
                       organism = synthetic construct
SEQUENCE: 163
ATVKFTYRGE GKQVGISRIK SVHRIGQWIK FWYDEGSGAY GRGYVSEKDA PKELLQMLKK    60
RGSEQKLISE ED                                                       72

SEQ ID NO: 164         moltype = AA  length = 72
FEATURE                Location/Qualifiers
REGION                 1..72
                       note = Synthetic Polypeptide
source                 1..72
                       mol_type = protein
                       organism = synthetic construct
SEQUENCE: 164
ATVKFTYRGE RKQVGISRIK SVHRIGQWIK FWYDEGSGAY GRGYVSEKDA PKELLQMLEK    60
RGSEQKLISE ED                                                       72

SEQ ID NO: 165         moltype = AA  length = 72
FEATURE                Location/Qualifiers
REGION                 1..72
                       note = Synthetic Polypeptide
source                 1..72
                       mol_type = protein
                       organism = synthetic construct
SEQUENCE: 165
ATVKFTYRGE EKQVGISRIK SVHRIGQWIK FWYDEGSGAY GRGYVSEKDA PKELLQMLEK    60
RGSEQKLISE ED                                                       72

SEQ ID NO: 166         moltype = AA  length = 72
FEATURE                Location/Qualifiers
REGION                 1..72
                       note = Synthetic Polypeptide
source                 1..72
                       mol_type = protein
                       organism = synthetic construct
SEQUENCE: 166
ATVKFTYRGE EKQVGISRIK SVHRVGQWIK FWYDEGSGAY GRGYVSEKDA PKELLQMLEK    60
RGSEQKLISE ED                                                       72

SEQ ID NO: 167         moltype = AA  length = 72
FEATURE                Location/Qualifiers
REGION                 1..72
                       note = Synthetic Polypeptide
source                 1..72
                       mol_type = protein
                       organism = synthetic construct
SEQUENCE: 167
ATVKFTYRGE ERQVGISRIK SVHRIGQWIK FWYDEGSGAY GRGYVSEKDA PKELLQMLEK    60
RGSEQKLISE ED                                                       72

SEQ ID NO: 168         moltype = AA  length = 72
FEATURE                Location/Qualifiers
REGION                 1..72
                       note = Synthetic Polypeptide
source                 1..72
                       mol_type = protein
                       organism = synthetic construct
SEQUENCE: 168
ATVKFTYRGE EKQVGISRIK SVHRIGQWIK FWYDEGSGAY GRGYVGEKDA PKELLQMLEK    60
RGSEQKLISE ED                                                       72

SEQ ID NO: 169         moltype = AA  length = 72
FEATURE                Location/Qualifiers
REGION                 1..72
                       note = Synthetic Polypeptide
source                 1..72
                       mol_type = protein
                       organism = synthetic construct
SEQUENCE: 169
```

```
ATVKFTYRGE EKRVGISRIK SVHRIGQWIK FWYDEGSGAY GRGYVSEKDA PKELLQMLEK    60
RGSEQKLISE ED                                                      72

SEQ ID NO: 170          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 170
ATVKFTYRGE EKQVGISRIK SVHRIGQWIK FWYDEGSGAY GRGYVSEKDA PKELLRMLEK    60
RGSEQKLISE ED                                                      72

SEQ ID NO: 171          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 171
ATVKFTYRGE EKQVGVSRIK SVHRIGQWIK FWYDGGSGAY GRGYVSEKDA PKELLQMLEK    60
RGSEQKLISE ED                                                      72

SEQ ID NO: 172          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 172
ATVKFTYRGE EKQVGISRIK SVHRIGQWIK FWYDGGSGAY GRGYVSEKDA PKELLQMLEK    60
RGSEQKLISE ED                                                      72

SEQ ID NO: 173          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 173
ATVKFTYRGE EKQVGVSRVK SVHRIGQWIK FWYDEGSGAY GRGYVSEKDA PEELLQMLEK    60
RGSEQKLISE ED                                                      72

SEQ ID NO: 174          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 174
ATVKFTYRGE EKQVGISRIK SVHRIGQWIK FWYDEGSGAH GRGYVSEKDA PKELLQMLEK    60
RGSEQKLISE ED                                                      72

SEQ ID NO: 175          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 175
ATVKFTYRGE EKQVGISRIK SVHRIGQWIK FRYDEGSGAY GRGYVSEKDA PKELLQMLEK    60
RGSEQKLISE ED                                                      72

SEQ ID NO: 176          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 176
VTVEFTYRGE EKQVDISKIK HVRRWGRWIW FIYEEGGGAK GRGGVSEKDA PKELLQMLEK    60
RGSEQKLISE ED                                                      72
```

```
SEQ ID NO: 177         moltype = AA  length = 72
FEATURE                Location/Qualifiers
REGION                 1..72
                       note = Synthetic Polypeptide
source                 1..72
                       mol_type = protein
                       organism = synthetic construct
SEQUENCE: 177
ATVKFTYQGE EKQVDISKIK HVRRWGRWIW FIYEEGGGAK GRGGVSEKDA PKELLQMLEK  60
QGSEQKLISE ED                                                     72

SEQ ID NO: 178         moltype = AA  length = 72
FEATURE                Location/Qualifiers
REGION                 1..72
                       note = Synthetic Polypeptide
source                 1..72
                       mol_type = protein
                       organism = synthetic construct
SEQUENCE: 178
ATVKFTYQGE EKQVDISKIK HVRRWGRWIW FIYEEGGGAK GRGGVSEKDA PKELLQMLEK  60
RGSEQKLISE ED                                                     72

SEQ ID NO: 179         moltype = AA  length = 72
FEATURE                Location/Qualifiers
REGION                 1..72
                       note = Synthetic Polypeptide
source                 1..72
                       mol_type = protein
                       organism = synthetic construct
SEQUENCE: 179
ATVRFTYQGE EKQVDISKIK HVRRWGRWIW FIYEEGGGAK GRGGVSEKDA PKELLQMLEK  60
RGSEQKLISE ED                                                     72

SEQ ID NO: 180         moltype = AA  length = 72
FEATURE                Location/Qualifiers
REGION                 1..72
                       note = Synthetic Polypeptide
source                 1..72
                       mol_type = protein
                       organism = synthetic construct
SEQUENCE: 180
ATVKFTYQGE EKQVDISKIK HVRRWGRWIW FIYEEGGGGK GRGGVSEKDA PKELLQMLEK  60
RGSEQKLISE ED                                                     72

SEQ ID NO: 181         moltype = AA  length = 72
FEATURE                Location/Qualifiers
REGION                 1..72
                       note = Synthetic Polypeptide
source                 1..72
                       mol_type = protein
                       organism = synthetic construct
SEQUENCE: 181
ATVKFTHQGE EKQVDISKIK HVRRWGRWIW FIYEEGGGAK GRGGVSEKDA PKELLQMLEK  60
RGSEQKLISE ED                                                     72

SEQ ID NO: 182         moltype = AA  length = 72
FEATURE                Location/Qualifiers
REGION                 1..72
                       note = Synthetic Polypeptide
source                 1..72
                       mol_type = protein
                       organism = synthetic construct
SEQUENCE: 182
AIVKFTYQGE EKQVDISKIK HVRRWGRWIW FIYEEGGGAK GRGGVSEKDA PKELLQMLEK  60
RGSEQKLISE ED                                                     72

SEQ ID NO: 183         moltype = AA  length = 72
FEATURE                Location/Qualifiers
REGION                 1..72
                       note = Synthetic Polypeptide
source                 1..72
                       mol_type = protein
                       organism = synthetic construct
SEQUENCE: 183
AAVKFTYQGE EKQVDISKIK HVRRWGRWIW FIYEEGGGAK GRGGVSEKDA PKELLQMLEK  60
QGSEQKLISE ED                                                     72

SEQ ID NO: 184         moltype = AA  length = 72
```

```
FEATURE                 Location/Qualifiers
REGION                  1..72
                        note = Synthetic Polypeptide
source                  1..72
                        mol_type = protein
                        organism = synthetic construct
SEQUENCE: 184
ATVKFTYQGE EKQVDISKIK HVRRWGRWIW FIYEAGGGAK GRGGVSEKDA PKELLQMLEK   60
QGSEQKLISE ED                                                      72

SEQ ID NO: 185          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 185
ATVKFTYQGE EKQVDISKIK HVRRWGRWIW FIYEGGGGAK GRGGVSEKDA PKELLQMLER   60
RGSEQKLISE ED                                                      72

SEQ ID NO: 186          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 186
ATVKFTYQGE EKQVDISKIK HVRRWGRWIW FIYEGGGGAK GRGGVSEKDA PKELLQMLEK   60
QGSEQKLISE ED                                                      72

SEQ ID NO: 187          moltype = AA   length = 69
FEATURE                 Location/Qualifiers
REGION                  1..69
                        note = Synthetic Polypeptide
source                  1..69
                        mol_type = protein
                        organism = synthetic construct
SEQUENCE: 187
ATVKFTYRGE EKQVDISKIK HVRRWGQWIW FIYDEGGGAK GKGSVSEKDA PKELLQMLEK   60
AGIRTKAYF                                                          69

SEQ ID NO: 188          moltype = AA   length = 69
FEATURE                 Location/Qualifiers
REGION                  1..69
                        note = Synthetic Polypeptide
source                  1..69
                        mol_type = protein
                        organism = synthetic construct
SEQUENCE: 188
ATVKFTYQGE EKQVDVSKIK HVRRWGQWIW FIYDEGGGAK GKGSVSEKDA PKELLQMLGK   60
AGIRTKAYF                                                          69

SEQ ID NO: 189          moltype = AA   length = 69
FEATURE                 Location/Qualifiers
REGION                  1..69
                        note = Synthetic Polypeptide
source                  1..69
                        mol_type = protein
                        organism = synthetic construct
SEQUENCE: 189
ATVKFTYQGE EKQVDISKIK HVRRWGRWIW FIYDEGGGAK GKGSVSEKDA PKELLQMLEK   60
AGIRTKAYF                                                          69

SEQ ID NO: 190          moltype = AA   length = 69
FEATURE                 Location/Qualifiers
REGION                  1..69
                        note = Synthetic Polypeptide
source                  1..69
                        mol_type = protein
                        organism = synthetic construct
SEQUENCE: 190
ATVKFTYQGE EKQVDISKIK HVRRWGRWIW FIYEEGGGAK GKGSVSEKDA PKELLQMLEK   60
AGIRTKAYF                                                          69

SEQ ID NO: 191          moltype = AA   length = 69
FEATURE                 Location/Qualifiers
REGION                  1..69
```

```
                        note = Synthetic Polypeptide
source                  1..69
                        mol_type = protein
                        organism = synthetic construct
SEQUENCE: 191
ATVKFTYQGE EKQVDISKIK HVRRWGQRIW FIYGEGGGAK GRGSVSEKDA PKELLQMLEK    60
AGIRTKAYF                                                           69

SEQ ID NO: 192          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 192
ATVKFTYQGE EKQVDISKIK HVRRWGRWIW FIYEEGGAKG RGGVSEKDAP KELLQMLEKQ    60
GSEQKLISEE DL                                                       72

SEQ ID NO: 193          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 193
ATVKFTYQGE EKQVDISKIK HVRRWGRWIW FTYEEGGGAK GRGGVSEKDA PKELLQMLEK    60
QGSEQKLILK RT                                                       72

SEQ ID NO: 194          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 194
ATVKFTYQGE EKQVDISKIK HVRRWGRWIW FTYEEGGGAK GRGGVSEKDA PKELLQMLEK    60
PGSEQKLISE ED                                                       72

SEQ ID NO: 195          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 195
ATVKFTYQGE EKQVDISKIK HVRRWGRWIW FTYEEGGGAR GRGGVSEKDA PKELLQMLEK    60
QGSEQKLISE ED                                                       72

SEQ ID NO: 196          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 196
ATVKFTYQGE EKQVDVSKIK HVRRWGRWIW FTYEEGGGAK GRGGVSEKDA PKELLQMLEK    60
QGSEQKLISE ED                                                       72

SEQ ID NO: 197          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 197
ATVKFTYQGE EKQVDISKIK HVRRWGRWIW FTYEEGGGAK GRGGVSEKDA PRELLQMLEK    60
RGSEQKLISE ED                                                       72

SEQ ID NO: 198          moltype = AA  length = 72
FEATURE                 Location/Qualifiers
REGION                  1..72
                        note = Synthetic Polypeptide
source                  1..72
```

```
                    mol_type = protein
                    organism = synthetic construct
SEQUENCE: 198
ATVKFTYRGE EKQVDISEIK HVRRWGRWIW FTYEEGGGAR GRGGVSEKDA PKELLQMLEK    60
RGSEQKLISE ED                                                       72

SEQ ID NO: 199          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 199
ATVKFTYQGE EKQVDISKIR HVRRWGRRIW FTYEEGGGAK GRGGVGEKDA PKELLQMLEK    60
QGSEQKLISE ED                                                       72

SEQ ID NO: 200          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 200
ATVKFTYQGE EKQVDISKIK HVRRWGRRIW FIYEEGGGAK GRGGVSEKDA PKELLQMLEK    60
QGSEQKLISE KD                                                       72

SEQ ID NO: 201          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 201
ATVKFTYQGE EKQVDISKIK HVRRWGRRIW FIYEEGGGAK GRGGVSEKDA PKELLQMLEK    60
QGSEQKLISE ED                                                       72

SEQ ID NO: 202          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 202
ATVKFTYQGE EKQVDISKIK HVRRWGRWIW FIYEEGGGAK GRGGVGEKDA PKELLQMLEK    60
QGSEQKLISE ED                                                       72

SEQ ID NO: 203          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 203
ATVKFTYQGE GKQVDISKIK HVRRWGRWIW FIYEEGGGAK GRGGVSEKDA PKELLQMLEK    60
QGSEQKLISE ED                                                       72

SEQ ID NO: 204          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 204
ATVKFTYQGE EKQVDISKIK RVRRWGRWIW FIYEEGGGAK GRGGVSEKDA PKELLQMLEK    60
QGSEQKLISE ED                                                       72

SEQ ID NO: 205          moltype = AA   length = 72
FEATURE                 Location/Qualifiers
REGION                  1..72
                        note = Synthetic Polypeptide
source                  1..72
                        mol_type = protein
                        organism = synthetic construct
```

```
SEQUENCE: 205
ITVKFTYQGE EKQVDISKIE HVRRWGRWIW FTYDEGGGAK GRGGVSEKGA PKELLQMLGK    60
RGSEQKLISE ED                                                      72

SEQ ID NO: 206          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 206
ITVKFTYRGE EKQVDISKIE HVRRWGQWIW FTYDEGGGAK GRGGVSEKGA PRELLQMLGK    60
RGSEQKLISE ED                                                      72

SEQ ID NO: 207          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 207
ATVKFTYQGE EKQVDISKIK HVRRWGRWIW FTYDEGGGAK GRGGVSEKGA PKELLQMLGK    60
RGSEQKLISE ED                                                      72

SEQ ID NO: 208          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 208
ATVKFTYQGE EKQVDISKIK HVRRWGRWIW FTYEEGGGAK GRGGVSEKDA PKELLQMLGK    60
RGSEQKLISE ED                                                      72

SEQ ID NO: 209          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 209
ATVKFTYQGE EKRVDISKIK HVRRWGRWIW FIYEEGGGAK GRGGVSEKDA PKELLQMLGK    60
RGSEQKLISE ED                                                      72

SEQ ID NO: 210          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 210
ATVKFTYQGE EKQVDISKIK HVRRWGRWIW FIYEEGGGAK GRGGVSEKDA PKELLQMLGK    60
QGSEQKLISE ED                                                      72

SEQ ID NO: 211          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 211
ATVKFTYRGE EKQVDISKIK HVRRWGRWIW FIYEGGGGAK GRGGVSEKDA PKELLQMLGK    60
QRSEQKLISE ED                                                      72

SEQ ID NO: 212          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 212
ATVKFTYHGE EKQVDISKIK HVRRWGRWIW FIYEEGGGAK GRGGVSEKDA PKELLQMLEK    60
```

```
                                                       -continued
QGSEQKLISE ED                                                         72

SEQ ID NO: 213         moltype = AA  length = 72
FEATURE                Location/Qualifiers
REGION                 1..72
                       note = Synthetic Polypeptide
source                 1..72
                       mol_type = protein
                       organism = synthetic construct
SEQUENCE: 213
ATVKFTYRGE EKQVDISKIK HVRRWGQWIW FIYDKGGGAK GRGGVSEKDA PKELLQMLEK      60
QGSEQKLISE ED                                                         72

SEQ ID NO: 214         moltype = AA  length = 72
FEATURE                Location/Qualifiers
REGION                 1..72
                       note = Synthetic Polypeptide
source                 1..72
                       mol_type = protein
                       organism = synthetic construct
SEQUENCE: 214
ATVKFTYRGE EKQVDISKIK HVRCWGQWIW FIYDKGGGAK GRGGVSEKGA PKELLQMLEK      60
QGSEQKLISE ED                                                         72

SEQ ID NO: 215         moltype = AA  length = 72
FEATURE                Location/Qualifiers
REGION                 1..72
                       note = Synthetic Polypeptide
source                 1..72
                       mol_type = protein
                       organism = synthetic construct
SEQUENCE: 215
ATVKFTYRGE EKQVGISRIR SVHRIGQWIK FWYDEGSGAY GRGYVSEKDA PKELLQMLEK      60
RGSEQKLISE ED                                                         72

SEQ ID NO: 216         moltype = AA  length = 72
FEATURE                Location/Qualifiers
REGION                 1..72
                       note = Synthetic Polypeptide
source                 1..72
                       mol_type = protein
                       organism = synthetic construct
SEQUENCE: 216
TTVKFTYRGE EKQVGISRIK SVHRIGQWIK FWYDKGSGAY GRGYVSEKDA PKELLQMLEK      60
RGSEQKLISE ED                                                         72

SEQ ID NO: 217         moltype = AA  length = 72
FEATURE                Location/Qualifiers
REGION                 1..72
                       note = Synthetic Polypeptide
source                 1..72
                       mol_type = protein
                       organism = synthetic construct
SEQUENCE: 217
AIVKFTYRGE EKQVGISRIK SVHRIGQWIK FWYGEGSGAY GRGYVSEKDA PKELLQMLEK      60
RGSEQKLISE ED                                                         72

SEQ ID NO: 218         moltype = AA  length = 72
FEATURE                Location/Qualifiers
REGION                 1..72
                       note = Synthetic Polypeptide
source                 1..72
                       mol_type = protein
                       organism = synthetic construct
SEQUENCE: 218
ATVKFTYRGG EKQVGISRIK SVHRIGQWIK FRYDEGSGAY GRGYVSEKDA PKELLQMLEK      60
RGSEQKLISE ED                                                         72

SEQ ID NO: 219         moltype = AA  length = 72
FEATURE                Location/Qualifiers
REGION                 1..72
                       note = Synthetic Polypeptide
source                 1..72
                       mol_type = protein
                       organism = synthetic construct
SEQUENCE: 219
ATVKFTYRGK EKQVGISRIK SVHRIGQWIK FRYDEGSGAY GRGYVSEKDA PKELLQMLEK      60
RGSEQKLISE ED                                                         72
```

```
SEQ ID NO: 220          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 220
ATVKFTYRGE EKQVDISRIK HVRRWGRWIW FIYEEGGGAK GRGGVSEKDA PKELLQMLEK   60
QGSEQKLISE ED                                                      72

SEQ ID NO: 221          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 221
ATVKFTYRGE EKQVDISKIK HVRRWGRWIW FIYEEGGGAK GRGGVSEKDA PKELLQMLEK   60
QGSEQKLISE ED                                                      72

SEQ ID NO: 222          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 222
ATVKFTYRGE EKQVDISKIK HVRRWGRWVW FIYEEGGGAK GRGGVSEKDA PKELLQMLEK   60
QGSEQKLISE ED                                                      72

SEQ ID NO: 223          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 223
ATVKFTYRGE EKQVDISKVK HVRRWGRWIW FIYEEGGGAK GRGGVSEKDA PKELLQMLEK   60
QGSEQKLISE ED                                                      72

SEQ ID NO: 224          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 224
ATVKFTYRGE EKQVDISKIK HVRRWGRWIW FIYEEGGGAK GRGGVSEKDA PKELLRMLEK   60
QGSEQKLISE ED                                                      72

SEQ ID NO: 225          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 225
ATVKFTYRGE EKQVDISKIK HVRRWGRWIW FIYEEGGGAK GRGGVSGKDA PKELLQMLEK   60
QGSEQKLISE ED                                                      72

SEQ ID NO: 226          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 226
ATVRFTYRGE EKQVDISKIK YVRRWGQYIW FGYDGGGGAR GYGYVSERDA PKELLQMLEE   60
QGSEQKLISE ED                                                      72

SEQ ID NO: 227          moltype = AA   length = 72
FEATURE                 Location/Qualifiers
```

```
REGION                   1..72
                         note = Synthetic Polypeptide
source                   1..72
                         mol_type = protein
                         organism = synthetic construct
SEQUENCE: 227
ATVRFTYQGE EKQVDISKIK HVRRWGRYIW FGYDEGGGAR GHGYVSEKDA PKELLQMLEK      60
QGSEQKLISE ED                                                         72

SEQ ID NO: 228           moltype = AA  length = 72
FEATURE                  Location/Qualifiers
REGION                   1..72
                         note = Synthetic Polypeptide
source                   1..72
                         mol_type = protein
                         organism = synthetic construct
SEQUENCE: 228
ATVQFTYQGE ERQVDISKIR HVRRWGRWIW FIYGEGGGAK GWGGVSAKDA PKELLQMLEK      60
QGSEQKLISE ED                                                         72

SEQ ID NO: 229           moltype = AA  length = 72
FEATURE                  Location/Qualifiers
REGION                   1..72
                         note = Synthetic Polypeptide
source                   1..72
                         mol_type = protein
                         organism = synthetic construct
SEQUENCE: 229
ATVKFTYQGG EKQVDISKIK HVRRWGQWIW FIYDEGGGAK GWGGVSGKDA PKELLQMLEK      60
RGSEQKLISE ED                                                         72

SEQ ID NO: 230           moltype = AA  length = 72
FEATURE                  Location/Qualifiers
REGION                   1..72
                         note = Synthetic Polypeptide
source                   1..72
                         mol_type = protein
                         organism = synthetic construct
SEQUENCE: 230
ATVKFTYRGE EKQVDISKIK YVRRWGQYIW FGYDEGGGAR GYGYVSERDA PKELLQMLEK      60
QGSEQKLISE ED                                                         72

SEQ ID NO: 231           moltype = AA  length = 72
FEATURE                  Location/Qualifiers
REGION                   1..72
                         note = Synthetic Polypeptide
source                   1..72
                         mol_type = protein
                         organism = synthetic construct
SEQUENCE: 231
ATVKFTYRGE EKQVDISKIK HVRRWGQYIW FGYDEGGGAR GYGYVSEKDA PKGLLQMLEK      60
QGSEQKLISE ED                                                         72

SEQ ID NO: 232           moltype = AA  length = 72
FEATURE                  Location/Qualifiers
REGION                   1..72
                         note = Synthetic Polypeptide
source                   1..72
                         mol_type = protein
                         organism = synthetic construct
SEQUENCE: 232
ATVKFTYRGE EKQVDISKIK HVRRWGQWIW FIYDEGGGAK GWGGVSERDA PKGLLQMLEK      60
QGSEQKLISE ED                                                         72

SEQ ID NO: 233           moltype = AA  length = 72
FEATURE                  Location/Qualifiers
REGION                   1..72
                         note = Synthetic Polypeptide
source                   1..72
                         mol_type = protein
                         organism = synthetic construct
SEQUENCE: 233
AAVKFTYQGE EKQVDISKIK YVWRWGRWIW FRYDEGGGAH GIGHVSEKDV PKELLQMLEK      60
QGSEQKLISE ED                                                         72

SEQ ID NO: 234           moltype = AA  length = 72
FEATURE                  Location/Qualifiers
REGION                   1..72
                         note = Synthetic Polypeptide
```

```
source                  1..72
                        mol_type = protein
                        organism = synthetic construct
SEQUENCE: 234
ATVRFTYRGE EKQVDISRIK YVRRWGQYIW LGYDGGGGAR GYGYVSEKGA PKELLQMLEK    60
QGSEQKLISE ED                                                       72

SEQ ID NO: 235          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 235
ATVKFTYRGE EKQVDISKIK YVRRWGQYIW FGYGEGGGAR GYGYVSEKDA PKELLQMLKK    60
QGSEQKLISE ED                                                       72

SEQ ID NO: 236          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 236
AAVKFTYQGE EKQVDTSKIK HVRRWGRYIW FGYDEGGGAR GHGYVSEKDA PKELLQMLEK    60
QGSEQKLISE ED                                                       72

SEQ ID NO: 237          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 237
ATVKFTYRGE EGQVDISKVK YVWRWGQWIW FRYDGGGGAH GIGYVSEKDT PKELLQMLEK    60
QGSEQKLISE ED                                                       72

SEQ ID NO: 238          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 238
ATVKFTYQGE EKQVGISKIR YVRRWGQYIW FGYDEGGGTR GYGYVSERDA PKELLQMLER    60
RGSEQKLISE ED                                                       72

SEQ ID NO: 239          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 239
ATVKFTYQGE EKQVDISKIK HVRRWGQWIW FIYDEGGGAR GRGYVSEKGA PEELLQMLGK    60
QGSEQKLISE ED                                                       72

SEQ ID NO: 240          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 240
ATVKFTYHGE GKQVDISKIK YVRRWGRYIW FGYDEGGGAR GYGYVSEKGA PEELLQMLEK    60
QGSEQKLISE ED                                                       72

SEQ ID NO: 241          moltype = AA  length = 72
FEATURE                 Location/Qualifiers
REGION                  1..72
                        note = Synthetic Polypeptide
source                  1..72
                        mol_type = protein
```

-continued

```
                        organism = synthetic construct
SEQUENCE: 241
ATVKFTYRGE EKQVDISKIK YVRRWGRYIW FGYDEGGGAR GYGYVSEKDA PKELLQMLEK   60
QGSEQKLISE ED                                                      72

SEQ ID NO: 242          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 242
ATVKFTYQGE EKQVDISKIK HVRRWGQWIW FIYDEGGGAK GWGGVSGKDA PKELLQMLEK   60
QGSEQKLISE ED                                                      72

SEQ ID NO: 243          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 243
ATVKFTYQGE EKQVDISKIK YVRRWGQYIW FGYGEGGGAR GYGHVSERDA PKELLQMLEK   60
QGSEQKLISE ED                                                      72

SEQ ID NO: 244          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 244
ATVKFTYRGE EKQVAISKIK YVRRWGQHIW FGYDKGGGAH GIGYVSERDA PKELLQMLDE   60
QGSEQKLISE ED                                                      72

SEQ ID NO: 245          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 245
ATVKFTYRGE EKRVDISKIK HVRRWGQWIW FIYDGGGGAK GWGGVSEKDA PKELLQMLEE   60
QGSEQKLISE ED                                                      72

SEQ ID NO: 246          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 246
ATVKFTYRGE EKQVDISKIK YVRRWGQYIW FGYDEGGGAR GYGYVSEKDA PEELLQMLEK   60
HGSEQKLISE ED                                                      72

SEQ ID NO: 247          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 247
ATVRFTYHGE EKQVDISKIK YVRRWGQWIW FIYDEGGGAN GKGSVSEKDA PKELLQMLEK   60
QGSEQKLISE ED                                                      72

SEQ ID NO: 248          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 248
```

```
ATVKFTYRGE EKQVDISKIK YVRRWGQYIW FGYDEGGGAR GHGYVSENDA PKELLQMLEK    60
QGSEQKLISE ED                                                       72

SEQ ID NO: 249          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 249
ATVEFTYRGE EKQVDISKIK YVRRWGQYIW FGYDGGGGAR GYGYVSEKDA PKELLQMLEE    60
QGSEQKLISE ED                                                       72

SEQ ID NO: 250          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 250
ATVKFTYRGE EKQVGISKIK YVRRWGQYIW FGYDEGGGAR GYGYVSEKDA PKELLQMLDK    60
QGSEQKLISE ED                                                       72

SEQ ID NO: 251          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 251
ATVKFTYRGE EKQVDISKIK HVRRWGQWIW FIYDGGGGAK GWGGVSEKDA PKELLQMLEK    60
QGSEQKLISE ED                                                       72

SEQ ID NO: 252          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 252
ATVKFTYRGE EKQVDISKIK HVRRWGQWIW FIYDEGGGAK GWGGVSEKDA PKELLQMLEK    60
QGSEQKLISE ED                                                       72

SEQ ID NO: 253          moltype = AA   length = 60
FEATURE                 Location/Qualifiers
REGION                  1..60
                        note = Synthetic Polypeptide
source                  1..60
                        mol_type = protein
                        organism = synthetic construct
SEQUENCE: 253
AVVRFTYRGE EKQVDISKIK YVRRWGQYIW FGYDEGGGAR GYGYVSEKDA PKELLRMLEK    60

SEQ ID NO: 254          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 254
ATVKFTYQGE EKRVDISKIK YVRRWGQYIW FGYDGGGGAR GYGHVSEKDA PRELLQMLEK    60
RGSEQKLISE ED                                                       72

SEQ ID NO: 255          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 255
ATVKFTYQGE EKQVDISKIK YVWRWGQWIW FHYDEGGGAR GYGYVSEKDA PKELLQMLGK    60
RGSEQKLISE ED                                                       72
```

| | | |
|---|---|---|
| SEQ ID NO: 256 | moltype = AA   length = 72 | |
| FEATURE | Location/Qualifiers | |
| REGION | 1..72 | |
| | note = Synthetic Polypeptide | |
| source | 1..72 | |
| | mol_type = protein | |
| | organism = synthetic construct | |

SEQUENCE: 256
ATVKFTYQGE EKQVDISKIK YVRRWGQYIW FGYDGGGGAR GYGHVSEKDA PKELLQMLGG   60
RGSEQKLISE ED                                                      72

| | | |
|---|---|---|
| SEQ ID NO: 257 | moltype = AA   length = 72 | |
| FEATURE | Location/Qualifiers | |
| REGION | 1..72 | |
| | note = Synthetic Polypeptide | |
| source | 1..72 | |
| | mol_type = protein | |
| | organism = synthetic construct | |

SEQUENCE: 257
ATVKFTYRGE EKQVDISKIK YVRRWGQYIW FGYDGGGGAR GYGHVSEKDA PKELLQMLEE   60
QGSEQKLISE ED                                                      72

| | | |
|---|---|---|
| SEQ ID NO: 258 | moltype = AA   length = 72 | |
| FEATURE | Location/Qualifiers | |
| REGION | 1..72 | |
| | note = Synthetic Polypeptide | |
| source | 1..72 | |
| | mol_type = protein | |
| | organism = synthetic construct | |

SEQUENCE: 258
ATVRFTYQGE EKQVDISKTK HVRRWGQWIW FIYDEAGGAH GRGRVSEKDA PKELLQMLEK   60
QGSEQKLISE ED                                                      72

| | | |
|---|---|---|
| SEQ ID NO: 259 | moltype = AA   length = 72 | |
| FEATURE | Location/Qualifiers | |
| REGION | 1..72 | |
| | note = Synthetic Polypeptide | |
| source | 1..72 | |
| | mol_type = protein | |
| | organism = synthetic construct | |

SEQUENCE: 259
ATVKFTYRGE EKQVDISKIK YVRRWGQYIW FGYDEGGGAR GYGYVSETDA PEKLLQMLEK   60
QGSEQKLISE ED                                                      72

| | | |
|---|---|---|
| SEQ ID NO: 260 | moltype = AA   length = 72 | |
| FEATURE | Location/Qualifiers | |
| REGION | 1..72 | |
| | note = Synthetic Polypeptide | |
| source | 1..72 | |
| | mol_type = protein | |
| | organism = synthetic construct | |

SEQUENCE: 260
ATVKFTYRGE EKQVDISKIK HVRRWGQWIW FIYDGGGGTK GWGGVSEKDA PKELLQMLEK   60
QGSEQKLISE ED                                                      72

| | | |
|---|---|---|
| SEQ ID NO: 261 | moltype = AA   length = 72 | |
| FEATURE | Location/Qualifiers | |
| REGION | 1..72 | |
| | note = Synthetic Polypeptide | |
| source | 1..72 | |
| | mol_type = protein | |
| | organism = synthetic construct | |

SEQUENCE: 261
ATVKFTYQGE EKQVDISKIK HVRRWGRWIW FIYDEGGGAK GWGGVSGRDA PKELLQMLEK   60
QGSEQKLISE ED                                                      72

| | | |
|---|---|---|
| SEQ ID NO: 262 | moltype = AA   length = 72 | |
| FEATURE | Location/Qualifiers | |
| REGION | 1..72 | |
| | note = Synthetic Polypeptide | |
| source | 1..72 | |
| | mol_type = protein | |
| | organism = synthetic construct | |

SEQUENCE: 262
ATVKFTYQGE EKQVGISRIK YVRRGQYIW FGYDKGGGAR GYGYVSEKDA PKELLQMLEK    60
QGSEQKLISE ED                                                      72

| | | |
|---|---|---|
| SEQ ID NO: 263 | moltype = AA   length = 72 | |
| FEATURE | Location/Qualifiers | |

```
REGION                  1..72
                        note = Synthetic Polypeptide
source                  1..72
                        mol_type = protein
                        organism = synthetic construct
SEQUENCE: 263
ATVRFTYQGE EKQVDISKIK HVRRWGQWIW FIYDEGGGAK GRGGVSEKDA PKELLQMLEK    60
QGSEQKLISE ED                                                        72

SEQ ID NO: 264          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 264
ATVKFTYRGE EKQVDISKIK YVRRWGQYIW FGYDEGGGAR GYGYVSEKDA PKGLLQMLEK    60
RGSEQKLISE ED                                                        72

SEQ ID NO: 265          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 265
ATVKFTYQGE EKQVDISKIK YVRRWGQRIS FIYDEGGGAR GYGRVSEKDA PKELLQLLEK    60
QGSEQKLISE ED                                                        72

SEQ ID NO: 266          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 266
ATVKFTYRGE EEQVDISKIK YVWRWGQWIW LRYDEGGGAH GIGYVSRKDA PKELLQMLEK    60
QGSEQKLISE ED                                                        72

SEQ ID NO: 267          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 267
ATVRFTYQGE ERRVDISKIK YVRRWGQHIW FGYDEGGGAR GYGYVNEKGA PRELLRMLEK    60
RGSEQKLISE ED                                                        72

SEQ ID NO: 268          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 268
ATVKFTYQGE EKQVDISKIK HVRRWGRWIW FIYDEGGGAK GRGGVSEKDA PKELLQMLEK    60
QGSEQKLISE ED                                                        72

SEQ ID NO: 269          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 269
ATVKFTYQGE EKQVDISEIK YVRRRGQYIW FGYDEGGGAR GYGYVSGKDA PKELLQMLER    60
RGSEQKLISE ED                                                        72

SEQ ID NO: 270          moltype = AA  length = 72
FEATURE                 Location/Qualifiers
REGION                  1..72
                        note = Synthetic Polypeptide
```

```
                        source          1..72
                                        mol_type = protein
                                        organism = synthetic construct
SEQUENCE: 270
ATVKFTYQGK EGQVAISKIK YVRRWGQYIW FGYDEGGGAR GYGYVSEKDA PKELLQMLGK    60
QGSEQKLISE ED                                                        72

SEQ ID NO: 271          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 271
ATVRFTYQGE EKQVDISKIK YVRRWGQYIW FGYDGGGGAR GYGYVSKKDA PKELLQMLER    60
QGSEQKLISE ED                                                        72

SEQ ID NO: 272          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 272
ATVKFTYQGE EKQVDISKIK YVWRWGRWIW FRYDEGGGAH GIGHVSEKGA PKELLRMLEK    60
QGSEQKLISE ED                                                        72

SEQ ID NO: 273          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 273
ATVKFTYQGE EKQVDISKIK HVRRWGRYIW FGYDEGGGAR GYGYVSEKAA PKGLLQMLGK    60
QGSEQKLISE ED                                                        72

SEQ ID NO: 274          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 274
ATVKFTYRGE EKQVDISKIK YVRRWGQYIW FGYDEGGGAR GYGYVSGKDA PKELLQMLEK    60
QGSEQKLISE ED                                                        72

SEQ ID NO: 275          moltype = AA   length = 60
FEATURE                 Location/Qualifiers
REGION                  1..60
                        note = Synthetic Polypeptide
source                  1..60
                        mol_type = protein
                        organism = synthetic construct
SEQUENCE: 275
ATVRFTYQGE EKQVDISRIK IVYRWGQRIS FIYDKGGGAR GYGRVSEKDA PKELLQMLEK    60

SEQ ID NO: 276          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 276
ATVRFTYRGG EKQVDISKIK YVRRWGQYVW FGYDKGGGVR GYGYVSEKDA PRELLQMLEK    60
QGSEQKLISE ED                                                        72

SEQ ID NO: 277          moltype = AA   length = 69
FEATURE                 Location/Qualifiers
REGION                  1..69
                        note = Synthetic Polypeptide
source                  1..69
                        mol_type = protein
                        organism = synthetic construct
```

```
SEQUENCE: 277
ATVKFTYRGE EKQVDISRIR SVSRWGQAIV FRYDEGGGAK GKGSVSEKDA PKELLQMLGK    60
AGIRTKAYF                                                            69

SEQ ID NO: 278          moltype = AA   length = 69
FEATURE                 Location/Qualifiers
REGION                  1..69
                        note = Synthetic Polypeptide
source                  1..69
                        mol_type = protein
                        organism = synthetic construct
SEQUENCE: 278
ATVKFTYQGE EKQVGISKIK HVRRWGQWIW FIYDEGGGAK GRGSVSERDA PKELLQMLEK    60
AGIRTKAYF                                                            69

SEQ ID NO: 279          moltype = AA   length = 69
FEATURE                 Location/Qualifiers
REGION                  1..69
                        note = Synthetic Polypeptide
source                  1..69
                        mol_type = protein
                        organism = synthetic construct
SEQUENCE: 279
ATVKFTYQGE EKQVDISKIK YVRRWGQYIW FGYDEGGGAR GYGYVSEKDA PKGLLQMLEK    60
ARIRTKAYF                                                            69

SEQ ID NO: 280          moltype = AA   length = 69
FEATURE                 Location/Qualifiers
REGION                  1..69
                        note = Synthetic Polypeptide
source                  1..69
                        mol_type = protein
                        organism = synthetic construct
SEQUENCE: 280
ATVKFTYRGE EKRVDISKIK YVRRWGQYIW FGYDEGGGAR GYGYVSGRDA PRELLQMLEK    60
ARIRTKAYF                                                            69

SEQ ID NO: 281          moltype = AA   length = 69
FEATURE                 Location/Qualifiers
REGION                  1..69
                        note = Synthetic Polypeptide
source                  1..69
                        mol_type = protein
                        organism = synthetic construct
SEQUENCE: 281
ATVQFTYQGG EKQVDISKIK YVRRWGRYIW LGYDEGGGAR GHGYVSEKDA PKELLQMLEK    60
ARIRTKAYF                                                            69

SEQ ID NO: 282          moltype = AA   length = 69
FEATURE                 Location/Qualifiers
REGION                  1..69
                        note = Synthetic Polypeptide
source                  1..69
                        mol_type = protein
                        organism = synthetic construct
SEQUENCE: 282
ATVEFTYQGE EKQVDISKIK YVRRWGQYIW FGYDEGGGAR GYGYVSEKDA PKELLQILEK    60
ARIRTKAYF                                                            69

SEQ ID NO: 283          moltype = AA   length = 69
FEATURE                 Location/Qualifiers
REGION                  1..69
                        note = Synthetic Polypeptide
source                  1..69
                        mol_type = protein
                        organism = synthetic construct
SEQUENCE: 283
ATVKFTYQGE EKQVDISKIK YVRRWGQYLW FGYDGGGAR GYGYVSEKDA PKELLQMLER     60
ARIRTKAYF                                                            69

SEQ ID NO: 284          moltype = AA   length = 69
FEATURE                 Location/Qualifiers
REGION                  1..69
                        note = Synthetic Polypeptide
source                  1..69
                        mol_type = protein
                        organism = synthetic construct
SEQUENCE: 284
ATVKFTYQGE ERQVDISKVK HVRRWGQWVW FIYDEGGGAK GWGGVSEKDA PTELLQMLEK    60
```

```
ARIRTKAYF                                                             69

SEQ ID NO: 285          moltype = AA  length = 69
FEATURE                 Location/Qualifiers
REGION                  1..69
                        note = Synthetic Polypeptide
source                  1..69
                        mol_type = protein
                        organism = synthetic construct
SEQUENCE: 285
ATVKFTYQGE EKQVDISRIK SAFRWGQAII FRYDEGGGAK GKGSVSEKDA PKELLQMLEK      60
ARIRTKAYF                                                             69

SEQ ID NO: 286          moltype = AA  length = 69
FEATURE                 Location/Qualifiers
REGION                  1..69
                        note = Synthetic Polypeptide
source                  1..69
                        mol_type = protein
                        organism = synthetic construct
SEQUENCE: 286
ATVEFTYRGE EKQVDISKIK YVRRWGQYIW FGYDEGGGAR GYGYVSEKDA PKELLQMLEK      60
AGIRTKAYF                                                             69

SEQ ID NO: 287          moltype = AA  length = 69
FEATURE                 Location/Qualifiers
REGION                  1..69
                        note = Synthetic Polypeptide
source                  1..69
                        mol_type = protein
                        organism = synthetic construct
SEQUENCE: 287
ATVKFTYQGE EKQVDISKIK YARRWGQYIW FGYDEGGGAR GYGYVSEEDA PKELLQMLEK      60
ARIRTKAYF                                                             69

SEQ ID NO: 288          moltype = AA  length = 69
FEATURE                 Location/Qualifiers
REGION                  1..69
                        note = Synthetic Polypeptide
source                  1..69
                        mol_type = protein
                        organism = synthetic construct
SEQUENCE: 288
ATVKFTYRGE EKQVDISKIK SVSRWGQAII FRYDEGGGAK GKGSVSEKDA PKELLQMLEK      60
ARIRTKAYF                                                             69

SEQ ID NO: 289          moltype = AA  length = 69
FEATURE                 Location/Qualifiers
REGION                  1..69
                        note = Synthetic Polypeptide
source                  1..69
                        mol_type = protein
                        organism = synthetic construct
SEQUENCE: 289
ATVKFAYQGE ERQVDISKIE YVRRWGQYIW FGYDEGGGAR GYGYVSEKDA PKELLQMLEK      60
ARIRTKAYF                                                             69

SEQ ID NO: 290          moltype = AA  length = 69
FEATURE                 Location/Qualifiers
REGION                  1..69
                        note = Synthetic Polypeptide
source                  1..69
                        mol_type = protein
                        organism = synthetic construct
SEQUENCE: 290
ATVKFTYQGE EKQVDVSKIK HVRRWGQWIW FIYDEGGGAK GWGGVSEKDA PKELLQMLEK      60
ARIRTKAYF                                                             69

SEQ ID NO: 291          moltype = AA  length = 69
FEATURE                 Location/Qualifiers
REGION                  1..69
                        note = Synthetic Polypeptide
source                  1..69
                        mol_type = protein
                        organism = synthetic construct
SEQUENCE: 291
ATVKFTYQGE EKQVGIGKIK HVRRWGQYIW FGYDGGGGAR GYGYVSEKDA PKGLLQMLEK      60
ARIRTKAYF                                                             69
```

```
SEQ ID NO: 292           moltype = AA   length = 69
FEATURE                  Location/Qualifiers
REGION                   1..69
                         note = Synthetic Polypeptide
source                   1..69
                         mol_type = protein
                         organism = synthetic construct
SEQUENCE: 292
ATVKFTYQGE EKQVDISKIK YVWRWGQWIW FRYDEGGGAK GKGSVSEKDA PRELLQMLEK    60
AGIRTKAYF                                                            69

SEQ ID NO: 293           moltype = AA   length = 69
FEATURE                  Location/Qualifiers
REGION                   1..69
                         note = Synthetic Polypeptide
source                   1..69
                         mol_type = protein
                         organism = synthetic construct
SEQUENCE: 293
ATVKFTYRGE EKQVDISKIK YVRRWGQYIW FGYDGGGGAR GYGHVSEKDA PKELLQMLEE    60
ARIRTKAYF                                                            69

SEQ ID NO: 294           moltype = AA   length = 69
FEATURE                  Location/Qualifiers
REGION                   1..69
                         note = Synthetic Polypeptide
source                   1..69
                         mol_type = protein
                         organism = synthetic construct
SEQUENCE: 294
ATVKFTYQGE EKQVDIGKIK YVRRWGQYIW FGYDEGGGAR GYGYVSEEDA PKELLQMLEK    60
ARIRTKAYF                                                            69

SEQ ID NO: 295           moltype = AA   length = 69
FEATURE                  Location/Qualifiers
REGION                   1..69
                         note = Synthetic Polypeptide
source                   1..69
                         mol_type = protein
                         organism = synthetic construct
SEQUENCE: 295
ATVKFTYQGE EKQVDISKIK SVHRVGQWIK FWYDEGGGAY GRGYVSERDA PRELLQMLEE    60
ARIRTKAYF                                                            69

SEQ ID NO: 296           moltype = AA   length = 69
FEATURE                  Location/Qualifiers
REGION                   1..69
                         note = Synthetic Polypeptide
source                   1..69
                         mol_type = protein
                         organism = synthetic construct
SEQUENCE: 296
ATVKFTYQGE EEQVAISKIK HVRRWGQWIW FRYDEGGGAH GIGYVSEKDA PKELLQMLEK    60
ARIRTKAYF                                                            69

SEQ ID NO: 297           moltype = AA   length = 69
FEATURE                  Location/Qualifiers
REGION                   1..69
                         note = Synthetic Polypeptide
source                   1..69
                         mol_type = protein
                         organism = synthetic construct
SEQUENCE: 297
ATVKFTYQGE EKQVDISKIK YVWRWGQWIW FRYDEGGGAH GIGYMSEKDA PRELLQMLGK    60
ARIRTKAYF                                                            69

SEQ ID NO: 298           moltype = AA   length = 69
FEATURE                  Location/Qualifiers
REGION                   1..69
                         note = Synthetic Polypeptide
source                   1..69
                         mol_type = protein
                         organism = synthetic construct
SEQUENCE: 298
ATVKFTYQGE EKQVEVSKIK YVRRWGQYIW FSYDEGGGAR GYGYVSERDA PRELLQMLEK    60
ARIRTKAYF                                                            69

SEQ ID NO: 299           moltype = AA   length = 69
FEATURE                  Location/Qualifiers
```

```
                        REGION          1..69
                                        note = Synthetic Polypeptide
                        source          1..69
                                        mol_type = protein
                                        organism = synthetic construct
SEQUENCE: 299
ATVKFTYRGE EKQVDISKIK SVSRWGQAII FRYDGGGGAR GKGSVSEKDA PKELLQMLEK      60
AGIRTKAYF                                                              69

SEQ ID NO: 300          moltype = AA    length = 69
FEATURE                 Location/Qualifiers
REGION                  1..69
                        note = Synthetic Polypeptide
source                  1..69
                        mol_type = protein
                        organism = synthetic construct
SEQUENCE: 300
ATVKFTYQGE EKQVDISKIK HVRRWGQWIW FIYDEGGGAK GWGGVSEKNA PKELLQMLEK      60
ARIRTKAYF                                                              69

SEQ ID NO: 301          moltype = AA    length = 69
FEATURE                 Location/Qualifiers
REGION                  1..69
                        note = Synthetic Polypeptide
source                  1..69
                        mol_type = protein
                        organism = synthetic construct
SEQUENCE: 301
ATVRFTYQGE EKQVDISKIK YVRRWGQYIW FGYDEGGGAR GYGYVSEKDT PKELLQLLEK      60
ARIRTKAYF                                                              69

SEQ ID NO: 302          moltype = AA    length = 69
FEATURE                 Location/Qualifiers
REGION                  1..69
                        note = Synthetic Polypeptide
source                  1..69
                        mol_type = protein
                        organism = synthetic construct
SEQUENCE: 302
ATVKFTYQGE EKQVDISKIK HVRRWGQWIW FIYDEGGGAK GKGSVSEKDA PKELLQMLEK      60
AGIRTKAYF                                                              69

SEQ ID NO: 303          moltype = AA    length = 69
FEATURE                 Location/Qualifiers
REGION                  1..69
                        note = Synthetic Polypeptide
source                  1..69
                        mol_type = protein
                        organism = synthetic construct
SEQUENCE: 303
ATVKFTYQGE EKQVDISKIK YVWRWGQAII FRYDEGGGAK GKGSVSEEDA PKELLQMLEK      60
ARIRTKAYF                                                              69

SEQ ID NO: 304          moltype = AA    length = 72
FEATURE                 Location/Qualifiers
REGION                  1..72
                        note = Synthetic Polypeptide
source                  1..72
                        mol_type = protein
                        organism = synthetic construct
SEQUENCE: 304
ATVKFTYRGE EKQVGISKIK YVRRWGQYIW FGYDEGGGAR GHGYVSEKDA PKELLQMLEK      60
QGSEQKLISE ED                                                          72

SEQ ID NO: 305          moltype = AA    length = 72
FEATURE                 Location/Qualifiers
REGION                  1..72
                        note = Synthetic Polypeptide
source                  1..72
                        mol_type = protein
                        organism = synthetic construct
SEQUENCE: 305
AAVKFTYQGE EKQVDIGRTK YVWRWGQWIW FRYDEGGGAR GYGCVGEKDA PRELLRVLEK      60
QGSEQKLISE ED                                                          72

SEQ ID NO: 306          moltype = AA    length = 72
FEATURE                 Location/Qualifiers
REGION                  1..72
                        note = Synthetic Polypeptide
```

```
source                   1..72
                         mol_type = protein
                         organism = synthetic construct
SEQUENCE: 306
ATVKFTYRGE EKQVDTSRIK YVWRWGQWIW FRYDEGGGAR GYGYVSEKDA PKELLQMLEK    60
QGSEQKLISE ED                                                        72

SEQ ID NO: 307           moltype = AA  length = 72
FEATURE                  Location/Qualifiers
REGION                   1..72
                         note = Synthetic Polypeptide
source                   1..72
                         mol_type = protein
                         organism = synthetic construct
SEQUENCE: 307
ATVRFTYQGE ERQVGISKIK YVRRRGQYIW FGYDEGGGVR GYGYVSEKGA PKELLRMLEK    60
RGSEQKLISE ED                                                        72

SEQ ID NO: 308           moltype = AA  length = 72
FEATURE                  Location/Qualifiers
REGION                   1..72
                         note = Synthetic Polypeptide
source                   1..72
                         mol_type = protein
                         organism = synthetic construct
SEQUENCE: 308
ATVKFTYQGE EKQVDISKIK HVRRWGQWIW FIYDEAGGAH GRGRVSERGA PKELLQMLEK    60
QGSEQKLISE ED                                                        72

SEQ ID NO: 309           moltype = AA  length = 72
FEATURE                  Location/Qualifiers
REGION                   1..72
                         note = Synthetic Polypeptide
source                   1..72
                         mol_type = protein
                         organism = synthetic construct
SEQUENCE: 309
ATVKFTYRGE EEQVGISRIK YVWRWGQWIW FRYDGGGGAR GYGHVSDKDA PKELLQMLEK    60
RGSEQKLISE ED                                                        72

SEQ ID NO: 310           moltype = AA  length = 72
FEATURE                  Location/Qualifiers
REGION                   1..72
                         note = Synthetic Polypeptide
source                   1..72
                         mol_type = protein
                         organism = synthetic construct
SEQUENCE: 310
ATVKFTYQGE EKQVDISRIK HVRRWGQWIW FIYDGAGGAH GRGRVSERGA PKELLQMLEK    60
QGSEQKLISE ED                                                        72

SEQ ID NO: 311           moltype = AA  length = 72
FEATURE                  Location/Qualifiers
REGION                   1..72
                         note = Synthetic Polypeptide
source                   1..72
                         mol_type = protein
                         organism = synthetic construct
SEQUENCE: 311
ATVKFTYQGE EKQVDISKVK YVRRRGQYIW FGYDEGDGAY GRGHVSEKGA PKELLQMLKK    60
QGSEQKLISE ED                                                        72

SEQ ID NO: 312           moltype = AA  length = 72
FEATURE                  Location/Qualifiers
REGION                   1..72
                         note = Synthetic Polypeptide
source                   1..72
                         mol_type = protein
                         organism = synthetic construct
SEQUENCE: 312
VTVKFTYQGE EKQVDISRIK HVRRWGQWIW FIYGKGGGAK GRGGVSEKDA PKELLQMLEK    60
QGSEQKLISE ED                                                        72

SEQ ID NO: 313           moltype = AA  length = 72
FEATURE                  Location/Qualifiers
REGION                   1..72
                         note = Synthetic Polypeptide
source                   1..72
                         mol_type = protein
```

```
                        organism = synthetic construct
SEQUENCE: 313
AAVKFTYRGE EKQVDISKIK YVRRWGQYIW FGYDKGGGAR GYGYVGEKGA PKELLQMLEK    60
QGSEQKLISE ED                                                       72

SEQ ID NO: 314          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 314
ATVKFTYRGE EKQVDISRIK YVRRWGQYIW FGYDEGGGAR GHGHVSEKEA PRELLQMLEK    60
QGSEQKLISE ED                                                       72

SEQ ID NO: 315          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 315
ATVKFTYQGE EKQVDISKIK HVRRWGQWIW FIYDEAGGAH GRGRVSERGA PRELLQMLEK    60
QGSEQKLISE ED                                                       72

SEQ ID NO: 316          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 316
ATVRFTYRGE ERQVGISKIK YVRRWGQYIW FGYDEGGGAR GYGYVSEKDA PKELLQMLDK    60
QGSEQKLISE ED                                                       72

SEQ ID NO: 317          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 317
ATVKFTYQGE EKQVGISRIK YVRRRGQYIW FGYDKGGGAR GHGYVGEKDA PKELLQMLGK    60
QGSEQKLISE ED                                                       72

SEQ ID NO: 318          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 318
ATVKFTYQGG EKQVDISKIK YVRRWGQHIW FGYDEGGGAR GYGYVSKKDA PKELLQMLEK    60
RGSEQKLISE ED                                                       72

SEQ ID NO: 319          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 319
ATVKFTYRGE EGQVDISKVK YVWRWGQWIW FRYDGGGGAH GIGHVSEKDT PKELLQMLEK    60
QGSEQKLISE ED                                                       72

SEQ ID NO: 320          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 320
```

```
ATVKFTYQGE EKQVDMSKIK HVRRWGQWIW FIYDEGGGAR GRGYVSEKGA PEELLQMLGK    60
QGSEQKLISE ED                                                       72

SEQ ID NO: 321          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 321
ATVKFTYQGR EKQVDISKIK HVRRRGQYIW FGYDKGGGAR GYGYVSEGDA PKELLQMLEK    60
QESEQKLISE ED                                                       72

SEQ ID NO: 322          moltype = AA  length = 69
FEATURE                 Location/Qualifiers
REGION                  1..69
                        note = Synthetic Polypeptide
source                  1..69
                        mol_type = protein
                        organism = synthetic construct
SEQUENCE: 322
ATVKFTYQGE EKQVGISKIR HVRRWGQWIW FIYDEGGGAK GRGSVSERDA PKELLQMLEK    60
ARIRTKAYF                                                           69

SEQ ID NO: 323          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 323
ATVKFTYQGG EKQVDISKIK HVRRWGQWVW FRYDEGGGAR GYGRVSEKGA PKELLQMLGK    60
QGSEQKLISE ED                                                       72

SEQ ID NO: 324          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 324
ATVKFTYHGE GKQVDISKIR YVRRWGRYIW FGYDEGGGAR GYGYVSEKGA PEELLQMLGK    60
QGSEQKLISE ED                                                       72

SEQ ID NO: 325          moltype = AA  length = 69
FEATURE                 Location/Qualifiers
REGION                  1..69
                        note = Synthetic Polypeptide
source                  1..69
                        mol_type = protein
                        organism = synthetic construct
SEQUENCE: 325
ATVKFTYRGE EKQVDISKIK HVRRWGQWIW FIYDEGGGAK GKGSVSEEDA PKELLQMLEK    60
VGIRTKAYF                                                           69

SEQ ID NO: 326          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 326
ATVKFTYRGG EKQVDISRVK YVWRRGQWIW FRYDGGGGAH GTGCVSEKNA PKELLQMLGR    60
QGSEQKLISE ED                                                       72

SEQ ID NO: 327          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 327
ATVKFTYQGE EKQVDISKIK HVRRWGQWIW FIYDKGGGAK GRGGVSDKDA PKELLQMLEK    60
QGSEQKLISE ED                                                       72
```

```
SEQ ID NO: 328          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 328
ATVRFTYRGE EKQVDISKIK HVRRWGQWIW FIYDEGGGAK GRGGVSKEDA PKELLRMLGK   60
QGSEQKLISE ED                                                      72

SEQ ID NO: 329          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 329
ATVKFTYHGE ERQVDISKIK HARRWGQWIW FIYDEGGGAK GRGGVSERNA PKELLQMLEG   60
RGSEQKLISE ED                                                      72

SEQ ID NO: 330          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 330
ATVRFTYQGE EKQVDISKIK YVRRRGQYIW FGYDEGGGAR GYGYVSGKGA PKELLQMLEE   60
HGSEQKLISE ED                                                      72

SEQ ID NO: 331          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 331
ATVKFTYRGE GKQVDISKIK HVRRWGQWIW FIYDEGGGAK GWGGVSEKGA PKALLQMLEK   60
QGSEQKLISE ED                                                      72

SEQ ID NO: 332          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 332
ATVEFTYRGE EKQVDISKIK HVRRWGQWIW FIYDEGGGAK GRGGVSERDA PKELLQLLEK   60
RGSEQKLISE ED                                                      72

SEQ ID NO: 333          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 333
ATVKFTYQGK EKQVDISKIK YVRRRGQYIW FGYDKSGGAR GYGYVSEKGA PKELLQMLEK   60
QGSEQKLISE ED                                                      72

SEQ ID NO: 334          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 334
ATVKFTYRGG EKQVDIGKIK YVRRWGQYVW FGYDEGGGAR GYGYVSEKDA PKELLQMLEK   60
RGSEQKLISE ED                                                      72

SEQ ID NO: 335          moltype = AA   length = 72
```

```
FEATURE                 Location/Qualifiers
REGION                  1..72
                        note = Synthetic Polypeptide
source                  1..72
                        mol_type = protein
                        organism = synthetic construct
SEQUENCE: 335
ATVKFTHRGE EKQVDASKIK YVRRWGRHIW FGYDEGGGAR GYGYVGEKDA PKELLQMLER   60
QGSEQKLISE ED                                                      72

SEQ ID NO: 336          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 336
ATVKFTYQGE EKQVDISKIK HVRRWGQWIW FTYDEGGGAK GRGGVSEKDA PKELLQMLEK   60
QGSEQKLISE ED                                                      72

SEQ ID NO: 337          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 337
TTVKFTYQGE EKQVDISKIK HVRRWGRWIW FTYDEGGGAK GRGGVSEKDA PKELLQMLEK   60
RGSEQKLISE ED                                                      72

SEQ ID NO: 338          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 338
TTVKFTYQGE EKQVDISKIK HVRRWGQWIW FTYDEGGGAK GRGGVSEKDA PKELLRMLEK   60
QGSEQKLISE ED                                                      72

SEQ ID NO: 339          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 339
ATVKFTYRGE EKQVAISKIK YVRRWGQHIW FGYDKGGGVR GYGYVGEKGA PRGLLQMLEK   60
QGSEQKLISE ED                                                      72

SEQ ID NO: 340          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 340
ATVRFTYQGE EKQVDINRIK HVRRWGQWIW FIYDEGGGAK GRGGVSGKDA PKELLQMLEK   60
QGSEQKLISE ED                                                      72

SEQ ID NO: 341          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 341
ATVKYTYRGE EKQVGISRIK SVHRIGQWIK FWYDEGSGAY GRGYVSEKDA PRELLQMLGK   60
RGSEQKLISE ED                                                      72

SEQ ID NO: 342          moltype = AA  length = 72
FEATURE                 Location/Qualifiers
REGION                  1..72
```

```
                        note = Synthetic Polypeptide
source                  1..72
                        mol_type = protein
                        organism = synthetic construct
SEQUENCE: 342
ATVKFTYQGE EKQVDISKIK HVRRWGQWIW FIYDKGGGAK GRGGVSEKDA PKELLQMLEK    60
QGSEQKLISE ED                                                       72

SEQ ID NO: 343          moltype = AA  length = 69
FEATURE                 Location/Qualifiers
REGION                  1..69
                        note = Synthetic Polypeptide
source                  1..69
                        mol_type = protein
                        organism = synthetic construct
SEQUENCE: 343
ATVKFTYQGE EKQVDISKIK YVRRWGQYIW FGYDAGGGVR GYGYVSEKDA PKGLLQMLEK    60
ARIRTKAYF                                                           69

SEQ ID NO: 344          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 344
ATVKFTYQGE EKQVNISKIK HVRRWGQWIW FVYDEGGGAK GRGGVSEKDA PKELLQMLEK    60
QGSEQKLISE ED                                                       72

SEQ ID NO: 345          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 345
ATVKFTYRGE EKQVDISEIR YVWRRGQWIW FRYDEGGGAH GIGHVSEKGA PKELLQTLER    60
QGSEQKLISE ED                                                       72

SEQ ID NO: 346          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 346
ATVKFTYRGE EKRVDISKIK HVRRWGQWIW FIYDEGGGAH GRGRVSEKDA PKELLQMLEK    60
QGSEQKLISE ED                                                       72

SEQ ID NO: 347          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 347
ATVKFTYQGG KKQMDISKLK YVRRWGRYIW FGYDEGGGAR GYGYVSGKDA PRELLQMLEK    60
QGSEQKLISE ED                                                       72

SEQ ID NO: 348          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 348
ATVKFTYRGE EKQVDISKIK YVRRWGQYVW FGYDEGGGAK GRGGVSKKDA PKELLQMLER    60
QGSEQKLISE ED                                                       72

SEQ ID NO: 349          moltype = AA  length = 72
FEATURE                 Location/Qualifiers
REGION                  1..72
                        note = Synthetic Polypeptide
source                  1..72
```

```
                        mol_type = protein
                        organism = synthetic construct
SEQUENCE: 349
ATVKFTYQGE EKQVDISKIK YVRRWGQYIW FGYDEGGGAR GRGYVSGKDA PKELLQMLEK    60
QGSEQKLISE ED                                                        72

SEQ ID NO: 350          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 350
ATVKFTYQGG EKQVGISRIK YVRRRGQYIW FGYDKGGGAR GYGYVSEKDA PKELLQMLEK    60
QGSEQKLISE ED                                                        72

SEQ ID NO: 351          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 351
ATVKFTYQGE EKQVDISKIK YVRRWGQYIW FGYDAGGGAR GYGYVSEKDA PKGLLQMLEK    60
RGSEQKLISE ED                                                        72

SEQ ID NO: 352          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 352
ATVKFTYQGE EKQVDISRIK YVRRWGQYIW FGYGEGGGAR GYGYVSEKDA PEGLLQMLGK    60
RGSEQKLISE ED                                                        72

SEQ ID NO: 353          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 353
AAVKFTYQGE ERQVDISKIK HVRRWGQWIW FIYDEGGGAK GRGGVSEKDA PKELLQMLER    60
QGSEQKLISE ED                                                        72

SEQ ID NO: 354          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 354
ATVKFTYRGE EKQADISKIK YVRRWGQYVW FGYDEGGGVR GYGYVSEKDA PKELLQMLEK    60
QGSEQKLISE ED                                                        72

SEQ ID NO: 355          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 355
ATVKFTYQGE EKQVDISKIK HVRRWGQWIW FVYDKGGGAK GRGGVSEKNA PKELLQMLER    60
QGSEQKLISE ED                                                        72

SEQ ID NO: 356          moltype = AA  length = 72
FEATURE                 Location/Qualifiers
REGION                  1..72
                        note = Synthetic Polypeptide
source                  1..72
                        mol_type = protein
                        organism = synthetic construct
```

```
SEQUENCE: 356
AIVKFTYHGE EKQVDISKIK YVRRWGQYIW FGYDEGGGAR GYGYVSERGA PKELLQMLEK    60
RGSEQKLISE ED                                                       72

SEQ ID NO: 357           moltype = AA   length = 72
FEATURE                  Location/Qualifiers
REGION                   1..72
                         note = Synthetic Polypeptide
source                   1..72
                         mol_type = protein
                         organism = synthetic construct
SEQUENCE: 357
ATVKFTYRGG EKQVDISKIK YVRRRGQYIW FGYDEGGGAR GYGYVSERDA PKELLQMLEK    60
QGSEQKLISE ED                                                       72

SEQ ID NO: 358           moltype = AA   length = 72
FEATURE                  Location/Qualifiers
REGION                   1..72
                         note = Synthetic Polypeptide
source                   1..72
                         mol_type = protein
                         organism = synthetic construct
SEQUENCE: 358
ATVKFTYQGE EKQVDISKIK HVRRWGQWIW FIYDKGGGAK GRGGVSEKNA PKELLQMLEK    60
QGSEQKLISE ED                                                       72

SEQ ID NO: 359           moltype = AA   length = 72
FEATURE                  Location/Qualifiers
REGION                   1..72
                         note = Synthetic Polypeptide
source                   1..72
                         mol_type = protein
                         organism = synthetic construct
SEQUENCE: 359
ATVEFTYQGE EKQVDISKIK HVRRWGQWIW FIYDEGGGAK GRGGVSERDA PKELLQLLEK    60
RGSEQKLISE ED                                                       72

SEQ ID NO: 360           moltype = AA   length = 72
FEATURE                  Location/Qualifiers
REGION                   1..72
                         note = Synthetic Polypeptide
source                   1..72
                         mol_type = protein
                         organism = synthetic construct
SEQUENCE: 360
ATVKFTYRGE GKQVDISKIK YVRRWGQYVW FGYDEGGGAR GYGYVSEKDA PKELLQMLEK    60
QGSEQKLISE ED                                                       72

SEQ ID NO: 361           moltype = AA   length = 72
FEATURE                  Location/Qualifiers
REGION                   1..72
                         note = Synthetic Polypeptide
source                   1..72
                         mol_type = protein
                         organism = synthetic construct
SEQUENCE: 361
ATVKFTYRGG EKQVDISRIK YVWRRGQWIW FRYDGGGGAH GTGCVSEKNA PKELLQMLGR    60
QGSEQKLISE ED                                                       72

SEQ ID NO: 362           moltype = AA   length = 72
FEATURE                  Location/Qualifiers
REGION                   1..72
                         note = Synthetic Polypeptide
source                   1..72
                         mol_type = protein
                         organism = synthetic construct
SEQUENCE: 362
ATVEFTYRGE EKQVDVSKIK YAWRWGRWIW FRYDEGGSAH GIGYVSEKDA PKELLQMLEK    60
QGSEQKLISE ED                                                       72

SEQ ID NO: 363           moltype = AA   length = 72
FEATURE                  Location/Qualifiers
REGION                   1..72
                         note = Synthetic Polypeptide
source                   1..72
                         mol_type = protein
                         organism = synthetic construct
SEQUENCE: 363
ATVKFTYQGE EKQVGVSRIT YVRRRGQYIW FGYDKGGGAR GYGYVSEKDA PKELLQMLEK    60
```

```
QGSEQKLISE ED                                                              72

SEQ ID NO: 364         moltype = AA  length = 72
FEATURE                Location/Qualifiers
REGION                 1..72
                       note = Synthetic Polypeptide
source                 1..72
                       mol_type = protein
                       organism = synthetic construct
SEQUENCE: 364
ATVKFTYRGE EKQVDISKIK YVRRWGQYIW FGYDGGGGAN GRGGVSERGA PKELLQMLGK           60
QGSEQKLISE ED                                                              72

SEQ ID NO: 365         moltype = AA  length = 72
FEATURE                Location/Qualifiers
REGION                 1..72
                       note = Synthetic Polypeptide
source                 1..72
                       mol_type = protein
                       organism = synthetic construct
SEQUENCE: 365
ATVEFTYQGE EKQVDIGKIK YVRRWGQYIW FGYDEGGGAR GYGYVSRKGA PKELLQMLEK           60
RGSEQKLISE ED                                                              72

SEQ ID NO: 366         moltype = AA  length = 72
FEATURE                Location/Qualifiers
REGION                 1..72
                       note = Synthetic Polypeptide
source                 1..72
                       mol_type = protein
                       organism = synthetic construct
SEQUENCE: 366
AIVRFTYRGE EKRVDISEIK YVRRWGQYIW FGYDKGGGAR GHGYVSEKDA PKELLQMLEE           60
QGSEQKLISE ED                                                              72

SEQ ID NO: 367         moltype = AA  length = 72
FEATURE                Location/Qualifiers
REGION                 1..72
                       note = Synthetic Polypeptide
source                 1..72
                       mol_type = protein
                       organism = synthetic construct
SEQUENCE: 367
ATVKFTYRGE EKQVDISKIK HARRWGQYIW FGYDEGGGAR GYGYVSEKDA PKELLRMLEK           60
RGSEQKLISE ED                                                              72

SEQ ID NO: 368         moltype = AA  length = 60
FEATURE                Location/Qualifiers
REGION                 1..60
                       note = Synthetic Polypeptide
source                 1..60
                       mol_type = protein
                       organism = synthetic construct
SEQUENCE: 368
ATVKFTYQGE EKQVDISRIK HVRRGGQYIW FGYDEGGGAR GYGYVSEKDA PKELLRMLEK           60

SEQ ID NO: 369         moltype = AA  length = 72
FEATURE                Location/Qualifiers
REGION                 1..72
                       note = Synthetic Polypeptide
source                 1..72
                       mol_type = protein
                       organism = synthetic construct
SEQUENCE: 369
ATVKFTYRGE EKQVDISKIK YVRRWGQYIW FGYDEGGGAR GHGRVSEKDA PRGLLQMLEK           60
QGSEQKLISE ED                                                              72

SEQ ID NO: 370         moltype = AA  length = 72
FEATURE                Location/Qualifiers
REGION                 1..72
                       note = Synthetic Polypeptide
source                 1..72
                       mol_type = protein
                       organism = synthetic construct
SEQUENCE: 370
AIVKFTHHGE EKQVDISKIK YVRRWGQYIW FGYDEGGGAR GYGYVSERDA PKELLQMLEK           60
RGSEQKLISE ED                                                              72

SEQ ID NO: 371         moltype = AA  length = 72
```

```
FEATURE                 Location/Qualifiers
REGION                  1..72
                        note = Synthetic Polypeptide
source                  1..72
                        mol_type = protein
                        organism = synthetic construct
SEQUENCE: 371
TTVKFTYQGE EKQVGISRIK YVRRRGQYIW FGYDKGGGAR GYGYVSGKDA PRELLQMLEK    60
QGSEQKLISE ED                                                       72

SEQ ID NO: 372          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 372
ATVRFTYHGE EKQVDISKIK YARRWGQYIW FGYDEGGGAR GYGHVSGEDA PKELLQMLEK    60
PGSEQKLISE ED                                                       72

SEQ ID NO: 373          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 373
ATVKFTYQGE EKQVDISKIK YVRRWGRYIW FGYDGGGGAR GYGHVSEKDA PKELLQMLGG    60
RGSEQKLISE ED                                                       72

SEQ ID NO: 374          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 374
ATVKFTYQGG EKQVDISKVR HVRRWGRWIW FGYDEGGGAH GRGRVSGKDA PKELLQMLEK    60
QGSEQKLISE ED                                                       72

SEQ ID NO: 375          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 375
ATVKFTYRGE EKQVDISKIK RVRRWGQWIW FIYDEAGGAH GRGRVSERGA PKELLQMLEK    60
QGSEQKLISE ED                                                       72

SEQ ID NO: 376          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 376
ATVEFTYQGE EKQVDISKIK HVRRRGQYIW FGYDKGGGAR GYGYVSEKDA PKELLQMLEK    60
QGSEQKLISE ED                                                       72

SEQ ID NO: 377          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 377
ATVKFTYRGE EKQVDISKIK HVRRWGQWIW FIYDEGGGAK GWGGVSEKDA PRGLLQMLER    60
QGSEQKLISE ED                                                       72

SEQ ID NO: 378          moltype = AA  length = 72
FEATURE                 Location/Qualifiers
REGION                  1..72
```

```
                        note = Synthetic Polypeptide
source                  1..72
                        mol_type = protein
                        organism = synthetic construct
SEQUENCE: 378
ATVKFTYQGE EKQVDISKIK YVRRWGQWIW FRYDGGGGAH GIGHVSEKDA PKELLQMLGK   60
QGSEQKLISE ED                                                      72

SEQ ID NO: 379          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 379
ATVKFTYHGE EKQVDISKIK YVRRWGQYIW FGYDEGGGAR GYGYVSGKGA PEELLQMLEK   60
QGSEQKLISE ED                                                      72

SEQ ID NO: 380          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 380
ATVKFTYQGE GKQVDISKIK HVRRWGQWIW FIYDEGGGAR GYGYVSGKDA PKKLLRMLEG   60
RGSEQKLISE ED                                                      72

SEQ ID NO: 381          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 381
AAVEFTYQGE EKQVDISKIK HVRRWGQWIW FIYDEAGGAH GRGRVSERGA PKELLQMLER   60
QGSEQKLISE ED                                                      72

SEQ ID NO: 382          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 382
ATVKFTYRGG EKQVDISKIK YVRRRGQYIW FGYDEGGGAR GYGYVSERDA PRELLQMLEK   60
QGSEQKLISE ED                                                      72

SEQ ID NO: 383          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 383
ATVKFTYRGE EKQVDISKIK YVRRRGQYIW FGYDEGGGAR GYGYVSEKDA PKELLQMLGK   60
QGSEQKLISE ED                                                      72

SEQ ID NO: 384          moltype = AA  length = 72
FEATURE                 Location/Qualifiers
REGION                  1..72
                        note = Synthetic Polypeptide
source                  1..72
                        mol_type = protein
                        organism = synthetic construct
SEQUENCE: 384
ATVKFTYRGE EKRVDTSKIK HVRRWGQWIW FTYDEGGGAK GRGGVSEKDA PKELLQMLEK   60
QGSEQKLISE ED                                                      72

SEQ ID NO: 385          moltype = AA  length = 72
FEATURE                 Location/Qualifiers
REGION                  1..72
                        note = Synthetic Polypeptide
source                  1..72
```

```
                        mol_type = protein
                        organism = synthetic construct
SEQUENCE: 385
ATVKFTYRGE EKQVDISKIK YVWRWGQWIW FRYDEGGGAH GIGHVSEKSA PKELLQTLGR    60
QGSEQKLISE ED                                                       72

SEQ ID NO: 386          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 386
ATVKSTYQGE EKQVDISKIK HVRRWGRWIW FIYDEGGGAK GWGGVSGRDA PKELLQMLEK    60
QGSEQKLISE ED                                                       72

SEQ ID NO: 387          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 387
AIVKFTYQGE ERQVDISKIK YVRRWGQYIW FGYDEGGGAH GRGRVSGKDA PKELLQMLEK    60
QGSEQKLISE ED                                                       72

SEQ ID NO: 388          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 388
ATVKFTYHGE ERQVDISKIK YVRRWGQYIW FGYGGGGAR GYGYVSEKDA PKELLQMLEK     60
QGSEQKLISE ED                                                       72

SEQ ID NO: 389          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 389
ATVKFTYQGE EKQVDISKIK YVRRWGQYIW FGYDGGGAR GRGYVSEKDA PKELLQMLEK     60
QGSEQKLISE ED                                                       72

SEQ ID NO: 390          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 390
VAVKFTYQGE EKRVDISKIK YVRRRGQYIW FGYGEGGGAR GYGYVSEKDA PKELLQMLAK    60
RGSEQKLISE ED                                                       72

SEQ ID NO: 391          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 391
ATVKFTYQGE EKQVDISKIK HVRRWGQWIW FIYDGGGGAK GRGGVSEKDA PKELLQMLEK    60
QGSEQKLISE ED                                                       72

SEQ ID NO: 392          moltype = AA   length = 72
FEATURE                 Location/Qualifiers
REGION                  1..72
                        note = Synthetic Polypeptide
source                  1..72
                        mol_type = protein
                        organism = synthetic construct
```

```
SEQUENCE: 392
ATVKFTYRGE EKQVDASRIK YVRRWGQYIW FGYDEGGGAR GYGYVSGRDA PKELLQMLEK    60
QGSEQKLISE ED                                                       72

SEQ ID NO: 393          moltype = AA   length = 72
FEATURE                 Location/Qualifiers
REGION                  1..72
                        note = Synthetic Polypeptide
source                  1..72
                        mol_type = protein
                        organism = synthetic construct
SEQUENCE: 393
ATVKFTYQGE EKQVDISKIR YARRRGQYIW FGYGEGGGAR GYGYVSDKDA PKELLRMLEK    60
QGSEQKLISE ED                                                       72

SEQ ID NO: 394          moltype = AA   length = 73
FEATURE                 Location/Qualifiers
REGION                  1..73
                        note = Synthetic Polypeptide
source                  1..73
                        mol_type = protein
                        organism = synthetic construct
SEQUENCE: 394
ATVKFTYRGE EKQVGISRIR SVHRIGQWIK FWYDEGSGAC GRGYVSEKGA PKELLQMLGK    60
RGSEQKLISE EDL                                                      73

SEQ ID NO: 395          moltype = AA   length = 73
FEATURE                 Location/Qualifiers
REGION                  1..73
                        note = Synthetic Polypeptide
source                  1..73
                        mol_type = protein
                        organism = synthetic construct
SEQUENCE: 395
ATVKFTYRGK EKRVGVSRIK SVRRIGQWIK FWYDEGSGAY GRGYVSEKDA PKELLQMLEK    60
RGSEQKLISE EDL                                                      73

SEQ ID NO: 396          moltype = AA   length = 73
FEATURE                 Location/Qualifiers
REGION                  1..73
                        note = Synthetic Polypeptide
source                  1..73
                        mol_type = protein
                        organism = synthetic construct
SEQUENCE: 396
ATVKFTYRGE EKQVGINRIK SVHRIGQWIK FWYDEGSGAY GRGYVSGKDA PKELLRMLEK    60
RGSEQKLISE EDL                                                      73

SEQ ID NO: 397          moltype = AA   length = 73
FEATURE                 Location/Qualifiers
REGION                  1..73
                        note = Synthetic Polypeptide
source                  1..73
                        mol_type = protein
                        organism = synthetic construct
SEQUENCE: 397
ATVKFTYQGE EKQVDISKIK IVYRWGQRIS FIYDEGGGAR GYGRVSEKDA PKELLQMLEK    60
QGSEQKLISE EDL                                                      73

SEQ ID NO: 398          moltype = AA   length = 73
FEATURE                 Location/Qualifiers
REGION                  1..73
                        note = Synthetic Polypeptide
source                  1..73
                        mol_type = protein
                        organism = synthetic construct
SEQUENCE: 398
ATVKFTYQGE EKQVDISKIK HVRRWGQWIW FIYDEGGGAK GWGGVSEKDA PKELLQMLEK    60
QGSEQKLISE EDL                                                      73

SEQ ID NO: 399          moltype = AA   length = 73
FEATURE                 Location/Qualifiers
REGION                  1..73
                        note = Synthetic Polypeptide
source                  1..73
                        mol_type = protein
                        organism = synthetic construct
SEQUENCE: 399
ATVKFTYQGE EKQVDISKIK YVRRWGQYIW FGYDEGGGAR GYGYVSEKDA PKELLQMLEK    60
```

```
QGSEQKLISE EDL                                                         73

SEQ ID NO: 400           moltype = AA   length = 73
FEATURE                  Location/Qualifiers
REGION                   1..73
                         note = Synthetic Polypeptide
source                   1..73
                         mol_type = protein
                         organism = synthetic construct
SEQUENCE: 400
ATVKFTYQGE EKQVDISKIK RVYRYGQWIW FRYDEGGGAY GGGWVSEKDA PKELLQMLEK      60
QGSEQKLISE EDL                                                         73

SEQ ID NO: 401           moltype = AA   length = 69
FEATURE                  Location/Qualifiers
REGION                   1..69
                         note = Synthetic Polypeptide
source                   1..69
                         mol_type = protein
                         organism = synthetic construct
SEQUENCE: 401
ATVKFTYQGE EKQVDISKIK SVSRWGQAII FRYDEGGGAK GKGSVSEKDA PKELLQMLEK       60
ARIRTKAYF                                                              69

SEQ ID NO: 402           moltype = AA   length = 61
FEATURE                  Location/Qualifiers
REGION                   1..61
                         note = Synthetic Polypeptide
source                   1..61
                         mol_type = protein
                         organism = synthetic construct
SEQUENCE: 402
ATVKFTYRGE EKQVGISRIK SVRRIGQWIK FWYDEGSGAY GRGYVSEKDA PKELLQMLEK       60
R                                                                      61

SEQ ID NO: 403           moltype = AA   length = 61
FEATURE                  Location/Qualifiers
REGION                   1..61
                         note = Synthetic Polypeptide
source                   1..61
                         mol_type = protein
                         organism = synthetic construct
SEQUENCE: 403
ATVKFTYRGE EKQVGISRIK SVRRIGQWIK FWYDEGSGAY GRGYVSGKDA PKELLQMLEK       60
R                                                                      61

SEQ ID NO: 404           moltype = AA   length = 61
FEATURE                  Location/Qualifiers
REGION                   1..61
                         note = Synthetic Polypeptide
source                   1..61
                         mol_type = protein
                         organism = synthetic construct
SEQUENCE: 404
ATVKFTYRGG EKQVGISRIK SVRRIGQWIK FWYDEGSGAY GRGYVSEKDA PKELLQMLEK       60
R                                                                      61

SEQ ID NO: 405           moltype = AA   length = 61
FEATURE                  Location/Qualifiers
REGION                   1..61
                         note = Synthetic Polypeptide
source                   1..61
                         mol_type = protein
                         organism = synthetic construct
SEQUENCE: 405
ATVKFTYRGE EKQVGISRIK SVHRIGRWIK FWYDEGSGAY GRGYVSEKDA PKELLQMLEK       60
R                                                                      61

SEQ ID NO: 406           moltype = AA   length = 61
FEATURE                  Location/Qualifiers
REGION                   1..61
                         note = Synthetic Polypeptide
source                   1..61
                         mol_type = protein
                         organism = synthetic construct
SEQUENCE: 406
ATVKFTYRGE EKQVGISRIK SVHRIGQWIK FWYDEGSGAY GRGYVSKKDA PKELLQMLEK       60
R                                                                      61
```

| SEQ ID NO: 407 | moltype = AA length = 7 |
| --- | --- |
| FEATURE | Location/Qualifiers |
| REGION | 1..7 |
| | note = Synthetic Polypeptide |
| source | 1..7 |
| | mol_type = protein |
| | organism = synthetic construct |
| SEQUENCE: 407 | |
| KKVWRVG | 7 |

| SEQ ID NO: 408 | moltype = AA length = 7 |
| --- | --- |
| FEATURE | Location/Qualifiers |
| REGION | 1..7 |
| | note = Synthetic Polypeptide |
| source | 1..7 |
| | mol_type = protein |
| | organism = synthetic construct |
| SEQUENCE: 408 | |
| QMISFTY | 7 |

| SEQ ID NO: 409 | moltype = AA length = 7 |
| --- | --- |
| FEATURE | Location/Qualifiers |
| REGION | 1..7 |
| | note = Synthetic Polypeptide |
| source | 1..7 |
| | mol_type = protein |
| | organism = synthetic construct |
| SEQUENCE: 409 | |
| ATGRGAV | 7 |

| SEQ ID NO: 410 | moltype = AA length = 10 |
| --- | --- |
| FEATURE | Location/Qualifiers |
| REGION | 1..10 |
| | note = Synthetic Polypeptide |
| source | 1..10 |
| | mol_type = protein |
| | organism = synthetic construct |
| SEQUENCE: 410 | |
| QVGVSRVKSV | 10 |

| SEQ ID NO: 411 | moltype = AA length = 10 |
| --- | --- |
| FEATURE | Location/Qualifiers |
| REGION | 1..10 |
| | note = Synthetic Polypeptide |
| source | 1..10 |
| | mol_type = protein |
| | organism = synthetic construct |
| SEQUENCE: 411 | |
| QVDISKIKKV | 10 |

| SEQ ID NO: 412 | moltype = AA length = 7 |
| --- | --- |
| FEATURE | Location/Qualifiers |
| REGION | 1..7 |
| | note = Synthetic Polypeptide |
| VARIANT | 2 |
| | note = X can be any naturally occurring amino acid |
| VARIANT | 2..6 |
| | note = Xs cannot simultaneously be KWV, sequentially |
| VARIANT | 4 |
| | note = X can be any naturally occurring amino acid |
| VARIANT | 6 |
| | note = X can be any naturally occurring amino acid |
| source | 1..7 |
| | mol_type = protein |
| | organism = synthetic construct |
| SEQUENCE: 412 | |
| KXVXRXG | 7 |

| SEQ ID NO: 413 | moltype = AA length = 7 |
| --- | --- |
| FEATURE | Location/Qualifiers |
| REGION | 1..7 |
| | note = Synthetic Polypeptide |
| VARIANT | 2 |
| | note = X can be any naturally occurring amino acid |
| VARIANT | 2..6 |
| | note = Xs cannot simultaneously be MST, sequentially |
| VARIANT | 4 |
| | note = X can be any naturally occurring amino acid |
| VARIANT | 6 |

```
                              -continued note = X can be any naturally occurring amino acid
source              1..7
                    mol_type = protein
                    organism = synthetic construct
SEQUENCE: 413
QXIXFXY                                                               7

SEQ ID NO: 414      moltype = AA  length = 7
FEATURE             Location/Qualifiers
REGION              1..7
                    note = Synthetic Polypeptide
VARIANT             2
                    note = X can be any naturally occurring amino acid
VARIANT             2..6
                    note = Xs cannot simultaneously be TRA, sequentially
VARIANT             4
                    note = X can be any naturally occurring amino acid
VARIANT             6
                    note = X can be any naturally occurring amino acid
source              1..7
                    mol_type = protein
                    organism = synthetic construct
SEQUENCE: 414
AXGXGXV                                                               7

SEQ ID NO: 415      moltype = AA  length = 59
FEATURE             Location/Qualifiers
REGION              1..59
                    note = Synthetic Polypeptide
source              1..59
                    mol_type = protein
                    organism = synthetic construct
SEQUENCE: 415
ATVKFTYQGE EKQVDISKIK SVHRVGQWIK FWYDGGGGAY GRGYVSEKDA PKELLQMLE     59

SEQ ID NO: 416      moltype = AA  length = 61
FEATURE             Location/Qualifiers
REGION              1..61
                    note = Synthetic Polypeptide
source              1..61
                    mol_type = protein
                    organism = synthetic construct
SEQUENCE: 416
ATVKFTYRGE EKQVDISKIK YVRRWGQYIW FGYDEGGGAR GYGYVSETDA PELLLQMLEK    60
Q                                                                    61

SEQ ID NO: 417      moltype = AA  length = 61
FEATURE             Location/Qualifiers
REGION              1..61
                    note = Synthetic Polypeptide
source              1..61
                    mol_type = protein
                    organism = synthetic construct
SEQUENCE: 417
ATVKFTYRGE GKQVGISRIK SVRRIGQWIK FWYDEGSGAY GRGYVSGKDA PKELLQMLEK    60
R                                                                    61

SEQ ID NO: 418      moltype = AA  length = 61
FEATURE             Location/Qualifiers
REGION              1..61
                    note = Synthetic Polypeptide
source              1..61
                    mol_type = protein
                    organism = synthetic construct
SEQUENCE: 418
ATVKFTYRGE EKQVGISRIK SVRRIGRWIK LWYDEGSGAY GRGYVSGKDA PKELLQMLEK    60
R                                                                    61
```

What is claimed is:

1. A method of producing a glycan-binding protein, comprising:
    providing a protein scaffold, wherein the protein scaffold has a maximum dimension of greater than or equal to 5 Angstroms and less than or equal to 100 Angstroms, no more than 200 amino acid residues, and a binding face area of less than or equal to 6 square nanometers (nm$^2$), wherein the binding face has a largest dimension that is smaller than 30 Angstroms;
    generating one or more variants of the protein scaffold;
    determining binding and/or binding selectivity of the one or more variants to a monosaccharide or disaccharide-binding determinant;
    selecting a variant exhibiting increased binding and/or binding selectivity to the monosaccharide or disaccharide-binding determinant from the one or more variants; and
    repeating the generating, determining and selecting steps, using the variant exhibiting increased binding and/or binding selectivity to the monosaccharide or disaccharide-binding determinant in each repeat.

2. A method of producing a glycan-binding protein, comprising:
    providing a protein scaffold, wherein the protein scaffold has no more than 200 amino acid residues, a melting temperature of greater than or equal to 50° C., and a binding face having a largest dimension that is smaller than 30 Angstroms;
    generating one or more variants of the protein scaffold;
    determining binding and/or binding selectivity of the one or more variants to a monosaccharide or disaccharide-binding determinant;
    selecting a variant exhibiting increased binding and/or binding selectivity to the monosaccharide or disaccharide-binding determinant from the one or more variants; and
    repeating the generating, determining and selecting steps, using the variant exhibiting increased binding and/or binding selectivity to the monosaccharide or disaccharide-binding determinant in each repeat.

3. A method of producing a glycan-binding protein, comprising:
    providing a protein scaffold, wherein the protein scaffold has no more than 200 amino acid residues, has a maximum dimension of greater than or equal to 5 Angstroms and less than or equal to 100 Angstroms, and is devoid of disulfides;
    generating one or more variants of the protein scaffold;
    determining binding and/or binding selectivity of the one or more variants to a monosaccharide or disaccharide-binding determinant;
    selecting a variant exhibiting increased binding and/or binding selectivity to the monosaccharide or disaccharide-binding determinant from the one or more variants; and
    repeating the generating, determining and selecting steps, using the variant exhibiting increased binding and/or binding selectivity to the monosaccharide or disaccharide-binding determinant in each repeat.

4. The method of claim 2, wherein the protein scaffold has a melting temperature of greater than or equal to 60° C.

5. The method of claim 2, wherein the protein scaffold has a melting temperature of greater than or equal to 70° C.

6. The method of claim 2, wherein the protein scaffold is devoid of disulfides and comprises no more than 4 cysteines.

7. The method of claim 2, wherein the protein scaffold has a binding face area of less than or equal to 6 square nanometers (nm$^2$).

8. The method of claim 2, wherein the protein scaffold has a binding face area of at least 4 square nanometers (nm$^2$).

9. The method of claim 2, wherein the protein scaffold has a binding face area of at least 5 square nanometers (nm$^2$).

10. The method of claim 2, wherein the repeating step is repeated at least 5 times.

11. The method of claim 2, wherein generating one or more variants of the protein scaffold comprises generating one or more variants of the protein scaffold that have, on average, greater than or equal to 1 amino acid mutation.

12. The method of claim 2, further comprising producing a variant exhibiting a $K_D$ of less than 10$^{-5}$ M to the monosaccharide or disaccharide-binding determinant.

13. The method of claim 2, wherein the protein scaffold is compatible with yeast surface display.

14. The method of claim 2, wherein the protein scaffold is synthesized and/or expressed in *E. coli*.

15. The method of claim 2, wherein the protein scaffold is bioconjugated to a fluorophore, purification tag, biocompatible resin, and/or 2-dimensional (2D) array.

16. The method of claim 2, wherein the protein scaffold has greater than or equal to 50 amino acid residues.

17. The method of claim 2, wherein the protein scaffold has greater than or equal to 75 amino acid residues.

18. The method of claim 17, wherein the protein scaffold has a melting temperature of greater than or equal to 60° C. and less than or equal to 90° C.

19. The method of claim 18, wherein the protein scaffold is devoid of disulfides; is compatible with yeast surface display; is synthesized and/or expressed in *E. coli*; and is bioconjugated to a fluorophore, purification tag, biocompatible resin, and/or 2-dimensional (2D) array.

20. The method of claim 19, wherein the protein scaffold has a binding face area of at least 5 square nanometers (nm$^2$) and less than or equal to 6 square nanometers (nm$^2$).

* * * * *